United States Patent
Hackett et al.

(10) Patent No.: US 7,148,203 B2
(45) Date of Patent: *Dec. 12, 2006

(54) NUCLEIC ACID TRANSFER VECTOR FOR THE INTRODUCTION OF NUCLEIC ACID INTO THE DNA OF A CELL

(75) Inventors: Perry B. Hackett, Shoreview, MN (US); Zoltan Ivics, Berlin (DE); Zsuzsanna Izsvak, Berlin (DE)

(73) Assignee: Regents of the University of Minnesota, Minneapolis, MN (US)

(*) Notice: Subject to any disclaimer, the term of this patent is extended or adjusted under 35 U.S.C. 154(b) by 638 days.

This patent is subject to a terminal disclaimer.

(21) Appl. No.: 10/263,159

(22) Filed: Oct. 2, 2002

(65) Prior Publication Data

US 2003/0124668 A1    Jul. 3, 2003

Related U.S. Application Data

(63) Continuation of application No. 09/142,593, filed as application No. PCT/US98/04687 on Mar. 11, 1998, now Pat. No. 6,489,458.

(60) Provisional application No. 60/065,303, filed on Nov. 13, 1997, provisional application No. 60/053,868, filed on Jul. 28, 1997, provisional application No. 60/040,664, filed on Mar. 11, 1997.

(51) Int. Cl.
A61K 31/70   (2006.01)
C12N 5/00    (2006.01)
C07H 21/02   (2006.01)
C07H 21/04   (2006.01)

(52) U.S. Cl. .................. 514/44; 536/23.1; 536/23.4; 536/23.5; 536/24.1; 435/325

(58) Field of Classification Search ............... None
See application file for complete search history.

(56) References Cited

U.S. PATENT DOCUMENTS

| | | | |
|---|---|---|---|
| 4,631,259 A | 12/1986 | Clewell et al. | |
| 5,464,758 A | 11/1995 | Gossen et al. | |
| 5,595,889 A | 1/1997 | Richaud et al. | |
| 5,677,170 A | 10/1997 | Devine et al. | |
| 5,719,055 A | 2/1998 | Cooper | |
| 5,814,618 A | 9/1998 | Bujard et al. | |
| 5,879,933 A | 3/1999 | Hodgson | |
| 5,928,888 A | 7/1999 | Whitney | |
| 5,948,681 A | 9/1999 | Scanlin et al. | |
| 6,013,240 A | 1/2000 | Behr | |
| 6,051,430 A | 4/2000 | Plasterk et al. | |
| 6,225,121 B1 | 5/2001 | Savakis et al. | |
| 6,489,458 B1 | 12/2002 | Hackett et al. | |
| 6,613,752 B1* | 9/2003 | Kay et al. ............ 514/44 | |
| 2002/0016975 A1 | 2/2002 | Hackett et al. | |
| 2002/0103152 A1 | 8/2002 | Kay et al. | |
| 2005/0003542 A1 | 1/2005 | Kay et al. | |

FOREIGN PATENT DOCUMENTS

| | | |
|---|---|---|
| EP | 0 485 701 A1 | 5/1992 |
| EP | 0 756 007 A2 | 1/1997 |
| WO | WO 88/01646 | 3/1988 |
| WO | WO 93/04701 | 3/1993 |
| WO | WO 93/25239 | 12/1993 |
| WO | WO 95/01095 | 1/1995 |
| WO | WO 96/01313 | 1/1996 |
| WO | WO 96/40892 | 12/1996 |
| WO | WO 97/15679 | 5/1997 |
| WO | WO 97/29202 | 8/1997 |
| WO | WO 98/24479 | 6/1998 |
| WO | WO 98/40510 | 9/1998 |
| WO | WO 98/56903 | 12/1998 |
| WO | WO 99/25817 | 5/1999 |
| WO | WO 99/59546 | 11/1999 |
| WO | WO 00/30687 | 6/2000 |
| WO | WO 00/68399 | 11/2000 |
| WO | WO 01/30965 A2 | 5/2001 |
| WO | WO 02/13602 A1 | 6/2001 |
| WO | WO 01/81565 A2 | 11/2001 |
| WO | WO 01/89579 A2 | 11/2001 |
| WO | WO 01/91802 A1 | 12/2001 |
| WO | WO 01/89579 A3 | 8/2002 |

OTHER PUBLICATIONS

Adey et al., "Molecular resurrection of an extinct ancestral promoter for mouse L1," *Proc. Natl. Acad. Sci. USA*, 91, 1569-1573 (1994).

Allende et al., "Insertional mutagenesis in zebrafish identifies two novel genes, pescadillo and dead eye, essential for embryonic development," *Genes Dev.*, 10, 3141-3155 (1996).

Amsterdam et al., "The *Aequorea victoria* green fluorescent protein can be used as a reporter in live zebrafish embryos," *Dev Biol.*, 171(1):123-9 (1995).

(Continued)

*Primary Examiner*—Joseph Woitach
(74) *Attorney, Agent, or Firm*—Mueting, Raasch & Gebhardt, P.A.

(57) ABSTRACT

This invention relates to a system for introducing nucleic acid into the DNA of a cell. The system includes the use of a member of the SB family of transposases (SB) or nucleic acid encoding the transposase and a nucleic acid fragment that includes a nucleic acid sequence with flanking inverted repeats. The transposase recognizes at least a portion of an inverted repeats and incorporates the nucleic acid sequence into the DNA. Methods for use of this system are discussed.

37 Claims, 13 Drawing Sheets

OTHER PUBLICATIONS

Anderson et al., "Gene expression in rainbow trout (Oncorhynchus mykiss) following intramuscular injection of DNA," *Mol. Mar. Biol. Biotech.*, 5, 105-113 (1996).

Ausubel, *Current Protocols in Molecular Biology*, Contents: Vols. 1,2, and 3, Tables of Contents (1994).

BD Biosciences Clontech Company, "Bidirectional Tet Expression Vectors, Simultaneously control expression of two genes with one tet-responsive element," [online] Palo Alto, CA [retrieved on Apr. 25, 2000]. Retrieved from the Internet: <http://www.clontech.com/archive/OCT96UPD/pBIVectors.html>; 3 pages.

BD Biosciences Clontech Company, "Tet Expression Systems & Cell Lines, Mammalian cell cultures systems for tightly regulated, high-level gene expression," [online] Palo Alto, CA [retrieved on May 30, 2000]. Retrieved from the Internet: <http://www.clontech.com/archive/JUL96UPD/Tet.html>, 6 pages.

BD Biosciences Clontech Company, "Tet System Vectors & Primers, Complete your Tet Systems tool kit with individual regulator and selection plasmids," [online] Palo Alto, CA [retrieved on Apr. 23, 2000]. Retrieved from the Internet: <http://www.clontech.com/archive/OCT96UPD/TetVectors.html>, 3 pages.

Ballinger et al., "Targeted gene mutations in Drosophila," *Proc. Natl. Acad. Sci. USA*, 86, 9402-9406 (1989).

Bandyopadhyay et al., "Enhanced gene transfer into HuH-7 cells and primary rat hepatocytes using targeted liposomes and polyethylenimine," *Biotechniques.* 25(2):282-92 (Aug. 1998).

Bandyopadhyay et al., "Nucleotide exchange in genomic DNA of rat hepatocytes using RNA/DNA oligonucleotides. Targeted delivery of liposomes and polyethyleneimine to the asialoglycoprotein receptor," *J Biol Chem.*, 274(15):10163-72 (1999).

Bayer et al., "A transgene containing *lacZ* is expressed in primary sensor neurons in zebrafish," *The Company of Biologists Limited*, 115:421-426 (1992).

Becker et al., "Chapter 8: Use of Recombinant Adenovirus for Metabolic Engineering of Mammalian Cells," Methods in Cell Biology, vol. 43: Protein Expression in Animal Cells, Roth, ed., Academic Press, New York, Title page, publication page, table of contents and pp. 161-189 (1994).

Beckwith, "lac: The Genetic System," The Operon, second edition, Miller et al., eds., Cold Spring Harbor Laboratory Press, New York, Title page, publication page, table of contents, and pp. 11-30 (1980).

Bellen et al., "P-element-mediated enhancer detection: a versatile method to study development in Drosophila," *Genes Dev.*, 3, 1288-1300 (1989).

Bellon et al., "Aerosol Administration of a Recombinant Adenovirus Expressing CFTR to Cystic Fibrosis Patients: A Phase I Clinical Trial," *Human Gene Ther.*, 8(1):15-25 (1997).

Bingham et al., "Cloning of DNA Sequences from the white Locus of D. melanogaster by a Novel and General Method," *Cell*, 25, 693-704 (1981).

Blazar et al., "*In utero* transfer of adult bone marrow cells into recipients with severe combined immunodeficiency disorder yields lymphoid progeny with T- and B-cell functional capabilities," *Blood*, 86(11):4353-66 (1995).

Bonaldo et al., "Efficient Gene Trap Screening for Novel Developmental Genes Using IRESβgeo Vector and *in Vitro* Preselection," *Experimental Cell Research*, 244, 125-136 (1998).

Borman et al., "Comparison of picornaviral IRES-driven internal initiation of translation in cultured cells of different origins," *Nucleic Acids Res.*, 25, 925-932 (1997).

Borman et al., "Picornavirus internal ribosome entry segments: comparison of translation efficiency and the requirements for optimal internal initiation of translation *in vitro*," *Nucleic Acids Res.*, 23, 3656-3663 (1995).

Bosma et al., "Bilirubin UDP-glucuronosyltransferase 1 is the Only Relevant Bilirubin Glucuronidating Isoform in Man," *J. Biol. Chem.*, 269, 17960-17964 (1994).

Boussif et al., "A versatile vector for gene and oligonucleotide transfer into cells in culture and *in vivo*: polyethylenimine," *Proc. Natl. Acad. Sci. USA*, 92(16):7297-301 (1995).

Bradley et al., "Formation of germ-line chimaeras from embryo-derived teratocarcinoma cell lines," *Nature*, 309, 255-256 (1984).

Bragonzi et al., "Comparison between cationic polymers and lipids in mediating systemic gene delivery to the lungs," *Gene Ther.*, 6, 1995-2004 (1999).

Burcin et al., "Adenovirus-mediated regulable target gene expression *in vivo*," *Proc. Nat'l. Acad. Sci. USA*, 96:355-360 (Jan. 19, 1999).

Caldovic et al., "Development of position-independent expression vectors and their transfer into transgenic fish," *Molecular Marine Biology and Biotechnology*, 4, 51-61 (1995).

Carey, "On the Trail of the Jumping Genes," *Business Week*, p. 89 (Jun. 29, 1998).

Choi et al., "Lactose-Poly(ethylene Glycol)-Grafted Poly-L-Lysine as Hepatoma Cell-Targeted Gene Carrier," *Bioconjugate Chem.*, 9:708-718 (1998).

Chowdhury et al., "Isolation of Multiple Normal and Functionally Defective Forms of Uridine Diphosphate-Glucuronosyltransferase from Inbred Gunn Rats," *J. Clin. Invest.*, 79, 327-334 (1987).

Chowdhury et al., "Gunn rat: a model for inherited deficiency of bilirubin glucuronidation," *Adv. Vet. Sci. Comp. Med.*, 37:149-73 (1993).

Clark et al., "Development of Dicistronic Vectors for Analysis of Transgene Expression in Zebrafish," Abstract presented at the 1998 meeting on "Zebrafish Development and Genetics," Cold Spring Harbor Laboratory, Cold Spring Harbor, NY (Apr. 29-May 3, 1998).

Clarke et al., "pPV: a novel IRES-containing vector to facilitate plasmid immunization and antibody response characterization," *Immunotech.*, 3(2):145-153 (1997).

Collas et al., "The nuclear localization sequence of the SV40 Tantigen promotes transgene uptake and expression in zebrafish embryo nuclei," *Transgenic Res.*, 5, 451-458 (1996).

Colloms et al., "DNA binding activities of the Caenorhabditis elegans Tc3 transposase," *Nucl. Acids Res.*, 22, 5548-5554 (1994).

Cooley et al., "Insertional Mutagenesis of the Drosophila Genome with Single P Elements," *Science*, 239, 1121-1128 (1988).

Cormack et al., "FACS-optimized mutants of the green flourescent protein (GFP)," *Gene*, 173, 33-38 (1996).

Craig, "Target Site Selection in Transposition," *Annu. Rev. Biochem.*, 66, 437-474 (1997).

Crameri et al., "Improved green fluorescent protein by molecular evolution using DNA shuffling," *Nat. Biotechnology*, 1996;14(3):315-319.

Curcio et al., "Regulation of retrotransposition in *Saccharomyces cerevisiae*," *Mol. Microbiol.*, 5(8):1823-1829 (1991).

Cusick, "Jumpy Gene Brought Back to Life," *ScienceNOW*, 1 page (Nov. 19, 1997).

Dalton et al., "Separation of Recombinant Human Protein C from Transgenic Animal Milk Using Immobilized Metal Affinity Chromatography," *Adv. Exp. Med. Biol.*, 411, 419-428 (1997).

Dawson et al., "Sleeping beauty awakes," *Nature Biotechnology*, 16, 20-21 (1998).

Devon et al., "Splinkerettes—improved vectorettes for greater efficiency in PCR walking," *Nucl. Acids. Res.*, 23, 1644-1645 (1995).

Diebold et al., "Mannose Polyethylenimine Conjugates for Targeted DNA Delivery into Dendritic Cells," *The Journal of Biological Chemistry*, 274(27):19087-19094 (1999).

Doak et al., "A proposed superfamily of transposase genes: Transposon-like elements in ciliated protozoa and a common 'D35E' motif," *Proc. Natl. Acad. Sci. USA*, 91, 942-946 (1994).

Dubois et al., "Colorimetric Method for Determination of Sugars and related substances," *Anal. Chem.* 28(3), 350-6 (1956).

Dupuy et al., "Adapting the *Sleeping Beauty* Transposon for Insertional Mutagenesis in the Mouse," Abstract presented at the 1998 meeting on "Mouse Molecular Genetics," Cold Spring Harbor Laboratory, Cold Spring Harbor, NY (Sep. 2-Sep. 6, 1998).

Ebert et al., "A Moloney MLV-Rate Somatotropin Fusion Gene Produces Biologically Active Somatotropin in a Transgenic Pig," *Mol. Endo.*, 2(3):277-283 (1988).

Eck et al., "Gene-Based Therapy," *Goodman & Gilman's The Pharmacological Basis of Therapeutics*, Chapter 5, pp. 77-101 (1996).

Economy Polymers and Chemicals, "Economy Products—Polyethyleneimine," product literature [online]; Houston, TX; [retrieved on May 10, 2001]; Retrieved from the Internet: URL:<http://www.economypolymers.com/polethyl.htm>; 2 pages.

Erbacher et al., "Transfection and physical properties of various saccharide, poly(ethylene glycol), and antibody-derivatized polyethylenimines (PEI)," *J. Gene Med.*, 1(3):210-22 (1999).

Essner et al., "Expression of Zebrafish *connexin43.4* in the Notochord and Tail Bud of Wild-Type and Mutant *no tail* Embryos," *Developmental Biology*, 177:449-462 (1996).

Essner et al., "The zebrafish thyroid hormone recptor α1 is expressed during early embryogenesis and can function in transcriptional repression," *Differentiation*, 62:107-117 (1997).

Evans et al., "Gene trapping and functional genomics," *TIG*, 13, 370-374 (1997).

Fadool et al., "Transposition of the *mariner* element from *Drosophila mauritiana* in zebrafish," *Proc. Nat'l. Acad. Sci. USA*, 95(9):5182-5186 (Apr. 1998).

Fahrenkrug et al., "Dicistronic Gene Expression in Developing Zebrafish," *Mar. Biotechnol.*, 1:552-561 (1999).

Ferry et al., "Liver-Directed Gene Transfer Vectors," *Human Gene Ther.*, 9(14):1975-1981 ((Sep. 20, 1998).

Fieck et al., "Modifications of the *E. coli* Lac repressor for expression in eukaryotic cells: effects of nuclear signal sequences on protein activity and nuclear accumulation," *Nuc. Acids Res.*, 20(7):1785-1791 (1992).

Finkelstein et al., "The use of bi-cistronic transfer vectors for the baculovirus expression system," *J. Biotechnol.*, 75(1):33-44 (Sep. 24, 1999).

Fire et al., "A modular set of *lacZ* fusion vectors for studying gene expression in *Caenorhabditis elegans*," *Gene*, 93(2):189-198 (1990).

Fletcher et al., "Mariner Transposon Mediated Stable Integration of Adenoviral Sequences for Use as Gene Therapy Vector System," Abstract 608, Fortieth Annual Meeting, American Society of Hematology, Miami Beach, Dec. 4-8, *Blood*, 92(10 Suppl. 1, Part 1 of 2):151a (Nov. 15, 1998).

Ghattas et al., "The Encephalomyocarditis Virus Internal Ribosome Entry Site Allows Efficient Coexpression of Two Genes from a Recombinant Provirus in Cultured Cells and in Embryos," *Mol. Cell. Biol.*, 11, 5848-5859 (1991).

Gibbs et al., "Inheritance of P element and reporter gene sequences in zebrafish," *Mol. Mar. Biol. Biotech.*, 3, 317-326 (1994).

Gierl et al., "TnpA product encoded by the transposable element En-1 of Zea mays is a DNA binding protein," *EMBO J.*, 4045-4053 (1988).

Gluzman et al., "Helper-free Adenovirus Type-5 Vectors," *Eukaryotic Viral Vectors*, Gluzman, ed., Cold Spring Harbor Laboratory Press, New York, title page, publication page, and pp. 187-192 (1982).

Gonzales et al., "Transposon mutagenesis of Haemophilus paragallinarum with Tn916," *Vet. Microbiol.*, 48, 283-291 (1996).

Goodier et al., "Tc1 Transposon-like Sequences are Widely Distributed in Salmonids," *J. Mol. Biol.*, 241, 26-34 (1994).

Gossen et al., "Tight control of gene expression in mammalian cells by *tetracycline-responsive promoters*," *Proc. Nat'l. Acad. Sci. USA*, 89(12):5547-5551 (1992).

Gossen et al., "Transcriptional Activation by Tetracyclines in Mammalian Cells," *Science*, 268:1766-1769 (1995).

Gray, "The direct coupling of oligosaccharides to proteins and derivatized gels," *Arch. Biochem. Biophys.*, 163(1):426-8 (1974).

Gueiros-Filho et al., "Trans-kingdom Transposition of the *Drosophila* Element *mariner* Within the Protozoan *Leishmania*," *Science*, 276:1716-1719 (1997).

Guo et al., "Receptor-targeted gene delivery via folate-conjugated polytheylenimine," *AAPS pharmsci electronic resource*, 1(4):E19 (1999).

Gurtu et al., "IRES bicistronic expression vectors for efficient creation of stable mammalian cell lines," *Biochem. and Biophys. Res. Comm.*, 229(1):295-298 (1996).

Hackett et al., "Construction of a Transposon System Active in Human Cells," *Keystone Symposia on Molecular & Cellular Biology*, Abstract and Poster (Jan. 20, 1998).

Hackett et al., "Development of Genetic Tools for Transgenic Animals," in: Murray et al., *Transgenic Animals in Agriculture*, (CABI Publishing, New York, 1999), Chap. 2, pp. 19-35 (Presentation from a conference held in California in Aug. 1997).

Hackett et al., "Development of Genetic Tools for Transgenic Fish," Abstract, Seminars in Singapore, Jul. 29-30, 1997 & UC Davis Biotechnology Program, Granlibakken Conference Center, Aug. 24-27, 1997.

Hackett et al., "Sleeping Beauty Transposon For Gene Therapy," Grant Abstract, Grant No. 2P01HD032652-060006 [online]. National Institute of Child Health and Human Development, National Institutes of Health, project dates Jan. 10, 1995-Dec. 31, 2002 [retrieved on Jun. 19, 2001]. Retrieved from the Internet: URL: http://commons.cit.nih.gov/crisp3/crisp_lib.getdoc?textkey=6325542&p_grant_num=2P01HD032652-060006&p_query=&ticket=16646&p_audit_session_id=381420&p_keywords=, 2 pages.

Hackett, "The molecular biology of transgenic fish," in *Biochemistry and Molecular Biology of Fishes*, vol. 2, Hochachka et al., eds., Elsevier Science Publisher B.V., Amsterdam, Chapter 9, pp. 207-240 (1993).

Hackett et al., "Zebrafish as a model system for biomedical research," Grant Abstract, Grant No. 2R01RR06625-05A1 [online]. National Center for Research Resources, National Institutes of Health, project dates Aug. 1, 1991-Aug. 31, 2000 [retrieved on Apr. 11, 2001]. Retrieved from the Internet: URL: http://commons.cit.nih.gov/crisp_historical/crisp_lib.getdoc?textkey=2397786&p_grant_num=2R01RR06625-05A1&p_query=&ticket=73379&p_audit_session_id=425461&p_keywords=, 2 pages.

Hackett et al., "Zebrafish as a Model System For Biomedical Research," Grant Abstract, Grant No. 5R01RR006625-06 [online]. National Center for Research Resources, National Institutes of Health, project dates Aug. 1, 1991-Aug. 31, 2000 [retrieved on Jun. 19, 2001]. Retrieved from the Internet: URL: http://commons.cit.nih.gov/crisp3/crisp_lib.getdoc?textkey=2772010&p_grant_num=5R01RR006625-06&p_query=&ticket=16646&p_audit_session_id=381420&p_keywords=, 2 pages.

Hallet et al., "Transposition and site-specific recombination: adapting DNA cut-and-paste mechanisms to a variety of genetic rearrangements," *FEMS Microbiology Reviews*, 21, 157-178 (1997).

Hammer et al., "Genetic Engineering of Mammalian Embryos," *J. Anim. Sci.*, 63, 269-278 (1986).

Handler et al., "A Functional Analysis of the P-Element Gene-Transfer Vector in Insects," *Arch. Insect Biochem. Physiol.*, 22, 373-384 (1993).

Hardy et al., "Construction of Adenovirus Vectors through Cre-*lox* Recombination," *J. Virol.*, 71(3):1842-1849 (1997).

Harlow et al., eds., *Antibodies: A Laboratory Manual*, Cold Spring Harbor Laboratory Press, Cold Spring Harbor, New York, NY ; copyright page and table of contents: 9 pages (1988).

Hartl, Daniel, L., "*Mariner* Sails into *Leishmania*," *Science*, 276, 1659-1660 (Jun. 13, 1997).

Hartl et al., "What restricts the activity of mariner-like transposable elements," *Trends Genet.*, 13, 197-201 (1997).

Hellen et al., "Translation of Encephalomyocarditis Virus RNA by Internal Ribosomal Entry," *Curr. Top. Microbiol. Immunol.*, 203:31-63 (1995).

Hirt, "Selective Extraction of Polyoma DNA from Infected Mouse Cell Cultures," *J. Mol. Biol.*, 26(2):365-369 (1967).

Horie et al., "Efficient Chromosomal Transposition of Tc1/Mariner-like Transposon Sleeping Beauty in Mice," *PNAS*, 98(16):9191-9196 (2001).

Hu et al., "The Inducible lac Operon-Repressor System Is Functional in Mammalian Cells," *Cell*, 48(4):555-566 (1987).

Ivics et al., "Development of Tc1-like transposable elements as genetic tools for Zebrafish (*Danio rerio*)," Abstract presented at "Second Biennial Meeting on Zebrafish Development and Genetics", Cold Spring Harbor Laboratory, Cold Spring Harbor, NY (Apr. 24-28, 1996).

Ivics et al., "Genetic Applications of Transposons and Other Repetitive Elements in Zebrafish," *Meth. Cell Biol.*, 60, 99-131 (1999).

Ivics et al., "Identification of functional domains and evolution of Tc1-like transposable elements," *Proc. Natl. Acad. Sci. USA*, 93, 5008-5013 (1996).

Ivics et al., "Molecular Reconstruction of Sleeping Beauty, a Tc1-like Transposon from Fish, and Its Transposition in Human Cells," *Cell*, 91, 501-510 (1997).

Ivics et al., "Repeated Sequence Elements in Zebrafish and Their Use in Molecular Genetic Studies," *The Zebrafish Science Monitor*, 3, 1-4 (1995).

Izsvak et al., Characterization of a Tc1-like transposable element in zebrafish (Danio rerio), *Mol. Gen. Genet.*, 247, 312-322 (1995).

Izsvak et al., "Involvement of a bifunctional, paired-like DNA-binding domain and a transpositional enhancer in Sleeping Beauty transposition," *J. Biol. Chem.*, 277(37):34581-34588 (2002).

Izsvak et al., "Nucleic acid sequence alignment and a predicted consensus sequence of the salmonid subfamily of Tc1-like transposable elements isolated from eight fish species," [online]. [retrieved Jun. 5, 2001]. Retrieved from the Internet: <URL:ftp://ftp.ebi.ac.uk/pub/databases/embl/align/ds30090.dat.>; 10 pages.

Izsvak et al., "Repetitive elements and their genetic applications in zebrafish," *Biochem. Cell Biol.*, 75, 507-523 (1997).

Izsvak et al., "Sleeping Beauty, a wide host-range transposon vector for genetic transformation in vertebrates," *J. Mol. Biol.*, 302, 93-102 (2000).

Izsvak et al., "Two-Stage Ligation-Mediated PCR Enhances the Detection of Integrated Transgenic DNA," *BioTechniques*, 15, 814,816, and 817 (1993).

Jang et al., "Cap independent translation of encephalomyocarditis virus RNA: structural elements of the internal ribosomal entry site and involvement of a cellular 57-kD RNA-binding protein," *Genes Dev.*, 4, 1560-1572 (1990).

Jermann et al., "Reconstructing the evolutionary history of the artiodactyl ribonuclease superfamily," *Nature*, 374, 57-59 (1995).

Kaiser et al., "Eukaryotic transposable elements as tools to study gene structure and function," in *Mobile Genetic Elements*, Sherratt, David, J., ed., IRL Press at Oxford University Press, Oxford/New York/Tokyo, pp. 69-100 (1995).

Kaminski et al., "Translation of encephalomyocarditis virus RNA: parameters influencing the selection of the internal initiation site," *EMBO J*, 13, 1673-1681 (1994).

Kaufman et al., "Improved vectors for stable expression of foreign genes in mammalian cells by use of the untranslated leader sequence from EMC virus," *Nucleic Acids Res.*, 19(16):4485-4490 (1991).

Kidwell, "Horizontal transfer," *Curr. Opin. Genet. Dev.*, 2, 868-873 (1992).

Kircheis et al., "Coupling of cell-binding ligands to polyethylenimine for targeted gene delivery," *Gene Ther.*, 4(5):409-18 (1997).

Klotz et al., "Macromolecule-small molecule interactions. Strong binding and cooperativity in a model synthetic polymer," *Biochemistry*, 8(12):4752-6 (1969).

Koga et al., "Transposable element in fish," *Nature*, 383, 30 (1996).

Korswagen et al., "Transposon Tc1-derived, sequence-tagged sites in Caenorhabditis elegans as markers for gene mapping," *Proc. Natl. Acad. Sci. USA*, 93, 14680-14685 (1996).

Koster et al., "Comparison of Monocistronic and Bicistronic Constructs for Neutrophin Transgene and Reporter Gene Expression in Fish Cells," *Mol. Mar. Biol. Biotech.*, 5(1):1-8 (1996).

Kren et al., "Alterations in mRNA stability during rat liver regeneration," *Am. J. Physiol.*, 270(5 Pt 1):G763-77 (May 1996).

Kren et al., "Correction of the UDP-glucuronosyltransferase gene defect in the Gunn rat model of Crigler-Najjar Syndrome type I with a chimeric oligonucleotide," *Proc. Natl. Acad. Sci. USA*. 96(18):10349-54 (1999).

Kutty et al., "Purification and Characterization of Biliverdin Reductase from Rat Liver," *J. Biol. Chem.*, 256, 3956-3962 (1981).

Lam et al., "Active transposition in zebrafish," *Proc. Natl. Acad. Sci. USA*, 93, 10870-10875 (1996).

Lam et al., "Discovery of Amphibian Tc1-like Transposon Families," *J. Mol. Biol.*, 257, 359-366 (1996).

Lampe et al., "A purified mariner transposase is sufficient to mediate transposition in vitro," *EMBO J.*, 15, 5470-5479 (1996).

Larregina et al., "FasL induces Fas/Apo1-mediated apoptosis in human embryonic kidney 293 cells routinely used to generate E1-deleted adenoviral vectors," *Gene Ther.*, 5(4):563-568 (Apr. 1998).

Lee et al., "Tn 10 insertional mutagenesis in Pasteurella multocida," *Vet. Microbiol.*, 50, 143-148 (1996).

Lewin, *Genes VI*, "Eukaryotic mRNAs have a methylated cap at the 5' end," Oxford University Press, pp. 171-172 (1997).

Lewin, *Genes VI*, "Nuclear splicing proceeds through a lariat," Oxford University Press, pp. 891-893 (1997).

Li et al., "Inversion and transposition of Tc1 transposon of *C. elegans* in mammalian cells," *Somat. Cell Mol. Genet.*, 24(6):363-369 (Nov. 1998).

Linehan-Stieers et al., "Uniform distribution and long-term expression of GFP in liver mediated by the Sleeping Beauty transposon system," abstract presented at Fourth Annual Meeting of the American Society of Gene Therapy, Seattle, Washington, May 30-Jun. 3, 2001 (1 page).

Liu et al., "Development of Expression Vectors for Transgenic Fish," *BioTechnol.*, 8, 1268-1272 (1990).

Liu et al., "Isolation and characterization of β-actin gene of carp (*Cyprinus carpio*)," *DNA Sequence-J. DNA Sequencing and Mapping*, 1, 125-136 (1990).

Lohe et al., "Horizontal Transmission, Vertical Inactivation, and Stochastic Loss of Mariner-like Transposable Elements," *Mol. Biol. Evol.*, 12, 62-72 (1995).

Lohe et al., "Mutations in the mariner transposase: The D, D(35)E consensus sequence is nonfunctional," *Proc. Natl. Acad. Sci. USA*, 94, 1293-1297 (1997).

Lönngren et al., "Aldonate coupling, a simple procedure for the preparation of carbohydrate-protein conjugates for studies of carbohydrate-binding proteins," *Arch. Biochem. Biophys.*, 175(2):661-9 (1976).

Loukeris et al., "Gene Transfer into the Medfly, Ceratitis capitata, with a Drosophila hydei Transposable Element," *Science*, 270, 2002-2005 (1995).

Lubon et al., "Blood Proteins from Transgenic Animal Bioreactors," *Transfusion Med. Rev.*, 10, 131-143 (1996).

Luo et al., "Chromosomal transposition of a Tc1/mariner-like element in mouse embryonic stem cells," *Proc. Natl. Acad. Sci. USA*, 95, 10769-10773 (1998).

Markkula et al., "Transgenic animals and gonadotrophins," *Rev. Reprod.*, 1, 97-106 (1996).

Marshall, "Gene Therapy on Trial," *Science*, 288, 951-957 (2000).

McGrory et al., "A Simple Technique for the Rescue of Early Region I Mutations into Infectious Human Adenovirus Type 5," *Virol.*, 163(2):614-617 (1988).

Meng et al., "Promoter analysis in living zebrafish embryos identifies a cis-acting motif required for neuronal expression of GATA-2," *Proc. Natl. Acad. Sci. USA.*, 94(12):6267-72 (1997).

Merwin et al., "CD5-mediated specific delivery of DNA to T lymphocytes: compartmentalization augmented by adenovirus," *Journal of Immunological Methods*, 186:257-266 (1995).

Michael, "Mutagenesis by Incorporation of a Phosphorylated Oligo During PCR Amplification," *BioTechniques*, 16, 410-412 (1994).

Moav et al. "Regulation of expression of transgenes in developing fish," *Transgenic Research*, 2:153-161 (1993).

Moerman et al., "Chapter 22: Mobile Elements in *Caenorhabditis elegans* and Other Nemotodes," *Mobile DNA*, Berg et al., eds., American Society for Microbiology, Title page, publication page, table of contents, and pp. 537-555 (1989).

Mohn et al., "Transposon-Mediated Transgenesis allows stable expression following germ-line transmission," Abstract presented at the 1988 meeting on Zebrafish Development & Genetics, Cold Spring Harbor Laboratory, Cold Spring Harbor, NY (Apr. 29-May 3, 1998).

Monsigny et al., "Colorimetric determination of neutral sugars by a resorcinol sulfuric acid micromethod," *Anal. Biochem.*, 175(2):525-30 (1988).

Moore et al., "Carbohydrate Characterization I. The Oxidation of Aldoses by Hypoiodite in Methanol; II. The Identification of Seven Aldo-Monosaccharides as Benzimidazole Derivatives," *J. Biol. Chem.* 133, 293-311 (1940).

Morgan et al., "Transposon tools for recombinant DNA manipulation: Characterization of transcriptional regulators from yeast, Xenopus, and mouse," *Proc. Natl. Acad. Sci. USA*, 93, 2801-2806 (1996).

Morral et al., "Administration of helper-dependent adenoviral vectors and sequential delivery of different vector serotype for long-term liver-directed gene transfer in baboons," *Proc. Nat'l. Acad. Sci. USA*, 96(22):12816-12821 (Oct. 26, 1999).

Mountford et al., "Internal ribosome entry sites and dicistronic RNAs in mammalian transgenesis," *Trends Genet.*, 11:179-184 (1995).

Mullins et al., "Perspectives Series: Molecular Medicine in Genetically Engineered Animals—Transgenesis in the Rate and Larger Mammals," *J. Clin. Inv.*, 97(7):1557-1560 (1996).

National Center for Biotechnology Information, National Library of Medicine, National Institutes of Health, GenBank Locus No. SMOTC1LT, Accession No. L12206, salmo salar (clone TC-TSS1) Tc1-like interspersed repetitive element encoding TcA-like transposase pseudogene) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids= 2 . . . , 2 pages.

National Center for Biotechnology Information, National Library of Medicine, National Institutes of Health, GenBank Locus No. SMOTC1LTA, Accession No. L12207, salmo salar (clone TC-TSS2) Tc1-like interspersed repetitive element and a transposase pseudogene) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids=2 . . . , 2 pages.

National Center for Biotechnology Information, National Library of Medicine, National Institutes of Health, GenBank Locus No. EMCPOLYP, Accession No. M81861, encephalomyocarditis virus polyprotein, complete cds.) [online]. Bethesda, MD [retrieved on Apr. 14, 2003]. Retrieved from Internet URL:<http://www.ncbi.nlm.nih.gov/entrez/query.fcgi?cmd=Retrieve&db=nucleotide&list_uids=2 . . . , 2 pages.

National Institutes of Health, "BLAST 2 Sequences," [online] Bethesda, MD [retrieved Apr. 9, 2002]. Retrieved from the Internet: <http://www.ncbi.nlm.nih.gov/gorf/b12.html>; 1 page.

National Institutes of Health, "BLAST 2 Sequences," [online] Bethesda, MD [retrieved Sep. 15, 2000]. Retrieved from the Internet: <http://www.ncbi.nlm.nih.gov/gorf/b12.html>; 1 page.

Okabe et al., "'Green Mice' as a Source of Ubiquitous Green Cells," *FEBS Letters*, 407, 313-319 (1997).

Oosumi et al., "Mariner transposons in humans," *Nature*, 378, 873 (1995).

Osborne et al., "Movers and shakers: maize transposons as tools for analyzing other plant genomes," *Curr. Opin. Cell Biol.*, 7, 406-413 (1995).

Padgett et al., "Splicing of Messenger RNA Precursors," *Ann. Rev. Biochem. J.*, 55, 1119-1150 (1988).

Pan et al., "The Binding Site of the Ic1R Repressor Protein Overlaps the Promoter of aceBAK," *Journal of Bacteriology*, Jul. 1996;178(13):3982-3982.

Parks et al., "A helper-dependent adenovirus vector system: Removal of helper virus by Cre-mediated excision of the viral packaging signal," *Proc. Nat'l. Acad. Sci. USA*, 93:13565-13570 (1996).

Pelletier et al., "Internal initiation of translation of eukaryotic mRNA derived from poliovirus RNA," *Nature*, 334, 320-325 (1988).

Perucho et al., "Genetic and Physical Linkage of Exogenous Sequences in Transformed Cells," *Cell*, 22, 309-317 (1980).

Petrov et al., "Diverse transposable elements are mobilized in hybrid dysgenesis in *Drosophila virilis*," *Proc. Natl. Acad. Sci. USA*, 92(17):8050-8054 (1995).

Plasterk, "Molecular Mechanisms of Transposition and Its Control," *Cell*, 74, 781-786 (1993).

Plasterk, "Reverse Genetics: From Gene Sequence to Mutant Worm," *Meth. Cell. Biol.*, 8, Academic Press, Inc., Chapter 3, 59-80 (1995).

Plasterk, "The Tc1/mariner Transposon Family," *Curr. Top. Microbiol. Immunol.*, 204, 125-143 (1996).

Plasterk et al., "Resident aliens the Tc1/mariner superfamily of transposable elements," *Trends in Genetics*, 15, 326-332 (1999).

Radice et al., "Widespread occurrence of the Tc1 transposon family: Tc1-like transposons from teleost fish," *Mol. Gen. Genet.*, 244, 606-612 (1994).

Raz et al., "Transposition of the nematode *Caenorhabditis elegans* Tc3 element in the zebrafish *Danio rerio*," *Current Biology*, 8, 82-83, 85, 87-88 (Dec. 12, 1997).

Rio et al., "Evidence for Drosophila P Element Transposase Activity in Mammalian Cells and Yeast," *J. Mol. Biol.*, 200, 411-415 (1988).

Ryter et al., "Heme oxygenase activity. Current Methods and Applications," *Methods Mol. Biol.*, 99, 369-91 (2000).

Sambrook et al., *Molecular Cloning: A Laboratory Manual*, Cold Spring Harbor Laboratory Press, table of contents and title page (1989).

Sarkar et al., "The 'Megaprimer' Method of Site-Directed Mutagenesis," *BioTechniques*, 8, 404-407 (1990).

Schneider, "BIOPHEX Highlights Gene Therapy Progress," *Gen. Eng. News*, 22(20), 4 pgs., (Nov. 15, 2002).

Schouten et al., "Transposon Tc1 of the nematode *Caenorhabditis elegans* jumps in human cells," *Nucleic Acids Research*, 26(12):3013-3017 (1998).

Sherratt, *Mobile Genetic Elements*, IRL Press, Oxford, Title Page and Table of Contents (1995).

Smit et al., "Tiggers and other DNA transposon fossils in the human genome," *Proc. Natl. Acad. Sci. USA*, 93, 1443-1448 (1996).

Snyder et al., "An improved 2,4,6-trinitrobenzenesulfonic acid method for the determination of amines," *Anal. Biochem.*, 064(1):284-8 (1975).

Spradling et al., "Gene disruptions using P transposable elements: An integral component of the Drosophila genome project," *Proc. Natl. Acad. Sci. USA*, 92, 10824-10830 (1995).

Stein et al., Eds., IUPAC-IUB Commission on Biochemical Nomenclature A One-Letter Notation for Amino Acid Sequences[1-3] Tentative Rules, *Journal of Biological Chemistry*, Jul. 10, 1968; 243(13):3557-3559.

Stewart, "Active ancestral molecules," *Nature*, 374, 12-13 (1995).

Suh et al., "Ionization of poly(ethylenimine) and poly(allylamine) at various pH's," *Bioorg. Chem.*, 22(3):318-327 (1994).

Szekely et al., "P element mediated germ line transformation of *Drosophila melonogaster* with the Tc1 transposable DNA element from *Caenorhabditis elegans*." *Genome*, 37(3):356-366 (1994).

Tatusova et al., "BLAST 2 Sequences, a new tool for comparing protein and nucleotide sequences," *FEMS Microbiol. Lett.*, 174(2):247-250 (May 15, 1999).

Trembley et al., "Differential regulation of cyclin B1 RNA and protein expression during hepatocyte growth *in vivo*," *Cell Growth Differ.*, 7(7):903-16 (1996).

Urabe et al., "A novel dicistronic AAV vector using a short IRES segment derived from hepatitis C virus genome," *Gene: An International Journal on Genes and Genomes*, 200(1-2):157-162 (1997).

van Luenen et al., "Mobilization of quiet, endogenous Tc3 transposons of *Caenorhabditis elegans* by forced expression of Tc3 transposase," *EMBO J.*, 12, 2513-2520 (1993).

van Luenen et al., "Target site choice of the related transposable elements Tc1 and Tc3 of *Caenorhabditis elegans*," *Nucleic Acids Research*, 22, 262-269 (1994).

van Luenen et al., "The Mechanism of Transposition of Tc3 in *C. elegans*," *Cell*, 79, 293-301 (1994).

Verma et al., "Gene Therapy—Promises, Problems, and Prospects," *Nature*, 389, 239-242 (1997).

von Melchner et al., "Identification of Cellular Promoters by Using a Retrovirus Promoter Trap," *J. Virol.*, 63, 3227-3233 (1989).

Vos et al., "Characterization of the *Caenorhabditis elegans* Tc1 transposase in vivo and in vitro," *Genes. Dev.*, 7, 1244-1253 (1993).

Vos et al., "Tc1 transposase of *Caenorhabditis elegans* is an endonuclease with a bipartite DNA binding domain," *EMBO J.*, 13, 6125-6132 (1994).

Vos et al., "Transposase is the only nematode protein required for in vitro transposition of Tc1," *Genes. Dev.*, 10, 755-761 (1996).

Wall et al., "Transgenic Dairy Cattle: Genetic Engineering on a Large Scale," *J. Dairy Sci.*, 80, 2213-2224 (1997).

Warren et al., "'Physiological genomics': Mutant screens in zebrafish," *Am J Physiol.* 275(1 Pt 2):H1-7 (1998).

Weber et al., "An SV40 'Enhancer Trap' Incorporates Exogenous Enhancers or Generates Enhancers from Its Own Sequences," *Cell*, 36, 983-992 (1984).

Weber et al., "Macrolide-based Transgene Control in Mammalian Cells and Mice," *Nature Biotechnology*, 20, 901-907 (2002).

Webster, "One-Step, Two-Step Regulation of Therapeutic Genes," *The Scientist*, available on line at http://www.the-scientist.com/yr1999/apr/opin_990426.html (Apr. 26, 1999).

Weinberg, Eric, S., "Zebrafish genetics: Harnessing horizontal gene transfer," *Current Biology*, 8, R244-R247 (1998).

Weng et al., "HO-1 expression in type II pneumocytes after transpulmonary gene delivery," *Am. J. Physiol. Lung Cell. Mol. Physiol.*, 278, L1273-L1279 (2000).

Westerfield, *The Zebrafish Book*, University of Oregon Press, Eugene, OR (1995), Title Page & Table of Contents only; text is available at zfish.uoregon.edu/zf_info/zfbook/zfbk.html.

Yant et al., "The development of new recombinant adenoviral vectors capable of stable integration into mammalian genomes," Abstract 922, p. 232a, 2nd Annual Meeting of the American Society of Gene Therapy, Jun. 9-13, 1999; in Washington, DC.

Yant et al., "Somatic integration and long-term transgene expression in normal and haemophilic mice using a DNA transposon system," *Nat. Genet.*, 25(1):35-41 (May 2000).

Yant et al., "Transposition from a gutless adeno-transposon vector stabilizes transgene expression in vivo," *Nature Biotechnology*, 20(10), 999-1005 (2002).

Ye et al., "Regulated Delivery of Therapeutic Proteins After in Vivo Somatic Cell Gene Transfer," *Science*, 283:88-91 (Jan. 1, 1999).

Yoon et al., "Targeted gene correction of episomal DNA in mammalian cells mediated by a chimeric RNA•DNA oligonucleotide." *Proc. Natl. Acad. Sci. USA.*, 93(5):2071-6 (1996).

Young et al., "Production of Biopharmaceutical Proteins in the Milk of Transgenic Dairy Animals," *Bio Pharm*, 10, 34-38 (1997).

Youngman et al., "Rte-1, a retrotransposon-like element in *Caenorhabditis elegans*," *FEBS Letter*, 380, 1-7 (1996).

Zambrowicz et al., "Disruption and sequence identification of 2,000 genes in mouse embryonic stem cells," *Nature*, 392, 608-611 (1998).

Zhang et al., "The Himar1 mariner transposase cloned in a recombinant adenovirus vector is functional in mammalian cells," *Nuc. Acids Res.*, 26(16):3687-3693 (Aug. 15, 1998).

Aldaz et al., "The Interwoven Architecture of the Mu Transposase Couples DNA Synapsis to Catalysis," *Cell*, 1996;85:257-269.

Baker et al., "Division of Labor among Monomers within the Mu Transposase Tetramer," *Cell*, 1993;74:723-733.

Birkenmeier et al., "Murine Mucopolysaccharidosis Type VII. Characterization of a Mouse with β-Glucuronidase Deficiency," *J. Clin. Invest.*, 1989;83(3):1258-1266.

Critchlow et al., "DNA end-joining: from yeast to man," *Trends Biochem. Sci.*, 1998;23:394-398.

Davis,"Polyethylenimine," *Water Soluble Resins*, Technical Service and Development, the Dow Chemical Company, Midland, MI, 216-226.

Fermentas, "ExGen™ 500 in vivo Transfection Reagent," [online]; retrieved on Apr. 4, 2002, retrieved from the Internet:<URL:http://www.fermentas.com/profiles/reagents/pexgen500(20x).htm>;4 pgs.

Fischer et al., "*Cis* requirements for transposition of Tc1-like transposons in *C. elegans*," *Mol. Gen. Genet.*, 1999;262:268-274.

Garrick et al., "Repeat-induced gene silencing in mammals," *Nature Genetics*, 1998;18:56-59.

Hackett, Perry B., "Zebrafish as a Model System for Biomedical Research," Grant Abstract, Grant No. 5R01RR006625-07 [online]. National Center for Research Sources, [retrieved on Jan. 20, 2004]. Retrieved from the Internet:<URL:http//crisp.cit.nih.gov/crisp/CRISP_LIB.getdoc?textkey=6056703&p_grant_num=5R01RR006625-07&p_. . . >; 2 pgs.

Hackett, Perry B., "Sleeping Beauty Transposon for Gene Therapy," Grant Abstract, Grant No. 5P01HD032652-070006 [online]. National Institute of Child Health and Human Development, [retrieved on Oct. 29, 2003]. Retrieved from the Internet:<URL:http//crisp.cit.nih.gov/crisp/CRISP_LIB.getdoc?textkey=6442591&p_grant_num=5P01 . . . >; 2 pgs.

Hackett et al., "Activity of the Sleeping Beauty System in Mammalian Cells," Keystone Meeting on Molecular and Cellular Biology of Gene Therapy, UT, Abstract, Jan. 14-20, 1999, 1 pg.

Henikoff, "Conspiracy of silence among repeated transgenes," *BioEssays*, 1998;20(7):532-535.

Ivics et al., "Molecular Reconstitution of an Active Tc1-like Transposable Element in Salmonid Fish," Keystone Symp. on Transposition and Site-Specific Recombination, Santa Fe, NM, Abstract, Mar. 1-8, 1997, 1 pg.

Ivics et al., "Molecular Reconstitution of an Active Tc1-like Transposable Element in Salmonid Fish," 4th Intl. Biotechnology Conf., Sorrento, Italy, Abstract, Sep. 22-29, 1997, 1 pg.

Ivics et al., "Molecular Archeology and the Development of Sleeping Beauty: a Novel Transposon for Gene Delivery in Vertebrates," Cold Spring Harbor Meeting on Zebrafish Genetics and Development, CSH Laboratory, NY, Abstract, Apr. 29-May 3, 1998, 1 pg.

Izsvak et al., "Characterization of a Tc1-like Repetitive Element in Zebrafish," Cold Spring Harbor Meeting, Abstract, Apr. 27-May 1, 1994:2 pgs.

Izsvak et al., "Composite Retroposons and Inverted Repeat Elements for Phylogenetic Analyses and Genetic Mapping in Zebrafish (*Danio rerio*)," Keystone Symp. on Transposition and Site-Specific Recombination, Santa Fe, NM, Abstract, Mar. 1-8, 1997, 1 pg.

Izsvak et al., "Composite Retroposons and Inverted Repeat Elements for Phylogenetic Analyses and Genetic Mapping in Fish," 4th Intl. Biotechnology Conf., Sorrento, Italy, Abstract, Sep. 22-29, 1997, 1 pg.

Izsvak et al., "Evolution and Genetic Applications of Retroposons and Inverted Repeat Transposable Elements in Zebrafish," Cold Spring Harbor Meeting on Zebrafish Genetics and Development, CSH Laboratory, NY, Abstract, Apr. 29-May 3, 1998, 1 pg.

Kawakami et al., "Identification of the *Tol2* transposase of the medaka fish *Oryzias latipes* that catalyzes excision of a nonautonomous *Tol2* element in zebrafish *Danio rerio*," *Gene*, 1999;240:239-244.

Ketting et al., "Target choice determinants of the Tc1 transposon of *Caenorhabditis elegans*," *Nucl. Acids Res.*, 1997;25(20):4041-4047.

Lampe et al., "Factors Affecting Transposition of the *Himar1 mariner* Transposon *in Vitro*," *Genetics*, 1998;149:179-187.

Liu et al., "Functional Analysis of Elements Affecting Expression of the β-Actin Gene of Carp," *Mol. Cell Biol.*, 1990;10(7):3432-3440.

Liu et al., "Hydrodynamics-based transfection in animals by systemic administration of plasmid DNA," *Gene Ther.*, 1999;6:1258-1266.

Mohn et al., "Transposon-Mediated Transgenesis Allows Stable Expression Following Germ-Line Transmission" Cold Spring Harbor Meeting on Zebrafish Genetics and Development, CSH Laboratory, NY, Abstract, Apr. 29-May 3, 1998, 1 pg.

National Center for Biotechnology Information, National Library of Medicine, National Institutes of Health, GenBank Locus AAD03792, Accession No. U89799.1, "Tc1-like transposase [Anopheles gambiae]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=40 . . . , 2 pages.

National Center for Biotechnology Information, National Library of Medicine, National Institutes of Health, GenBank Locus AAD03793, Accession No. U89800.1, "Tc1-like transposase [Anopheles gambiae]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=40 . . . , 2 pages.

National Library of Medicine, National Institutes of Health, GenBank Locus AAD03794, Accession No. U89803.1, "Tc1-like transposase [Anopheles gambiae]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=40 . . . , 2 pages.

National Center for Biotechnology Information, National Library of Medicine, National Institutes of Health, GenBank Locus CAA82359, Accession No. Z29098.1, "transposase (putative) [Drosophila hydei]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=43 . . . , 2 pages.

National Center for Biotechnology Information, National Library of Medicine, National Institutes of Health, GenBank Locus S26856, Accession No. S26856, "transposase—fruit fly (Drosophila hydei) transposon Minos," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=28 . . . , 2 pages.

National Center for Biotechnology Information, National Library of Medicine, National Institutes of Health, GenBank Locus CAB51371, Accession No. AJ249084.1, "transposase [Pleuronectes platessa]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=55 . . . , 2 pages.

National Center for Biotechnology Information, National Library of Medicine, National Institutes of Health, GenBank Locus CAB51372, Accession No. AJ249085.1, "transposase [Pleuronectes platessa]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=55 . . . , 2 pages.

National Center for Biotechnology Information, National Library of Medicine, National Institutes of Health, GenBank Locus CAC28060, Accession No. AJ303069.1, "putative transposase [Pleuronectes platessa]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=12 . . . , 2 pages.

National Center for Biotechnology Information, National Library of Medicine, National Institutes of Health, GenBank Locus AAB02109, Accession No. L76231.1, "transposase [Anopheles albimanus]," [online]. Bethesda, MD [retrieved on Oct. 22, 2003]. Retrieved from the Internet:<URL:<http://www.ncbi.nlm.nih.gov/entrez/query.fcgi?cmd=Retrieve&db=protein&list_uids=11 . . . , 1 pg.

National Center for Biotechnology Information, National Library of Medicine, National Institutes of Health, GenBank Locus S33560, Accession No. S33560, "hypothetical protein—fruit fly (Drosophila melanogaster) transposon-like element Bari-1," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=63 . . . , 2 pages.

National Center for Biotechnology Information, National Library of Medicine, National Institutes of Health, GenBank Locus B46189, Accession No. B46189, "orf within vasotocin gene (Tes1 element)—Pacific hagfish," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=42 . . . , 1 page.

National Center for Biotechnology Information, National Library of Medicine, National Institutes of Health, GenBank Locus CAB63420, Accession No. Z99288.1, "Hypothetical protein ZK262.5 [*Caenorhabditis elegans*]," [online]. Bethesda, MD [retrieved on Oct. 22, 2003]. Retrieved from the Internet:<URL: <http://www.ncbi.nlm.nih.gov/entrez/query.fcgi?cmd=Retrieve&db=protein&list_uids=65 . . . , 2 pages.

Savilahti et al., "Mu Transpositional Recombination: Donor DNA Cleavage and Strand Transfer in *trans* by the Mu Transposase," *Cell*, 1996;85:271-280.

Schleif, "DNA Looping," *Science*, 1988;240:127-128.

Shapiro, "Natural genetic engineering in evolution," *Genetica*, 1992;86:99-111.

Balciunas et al., "Enhancer trapping in zebrafish using the *Sleeping Beauty* transposon," *BMC Genomics*, Sep. 3, 2004;5:62:1-15.

Baus et al., "Hyperactive Transposase Mutants of the *Sleeping Beauty* Transposon," *Mol. Ther.*, Dec. 2005; 12(6):1148-1156. [Epub Sep. 8, 2005].

Belur et al., "Long-term Expression in Mouse Lung After Non-viral Sleeping Beauty-mediated Gene Transfer," *Mol. Therapy*;3:S60, Amer. Soc. Gene Therapy, Seattle, WA, Abstract, May 30-Jun. 3, 2001, 1 pg.

Belur et al., "Sleeping Beauty: A Non-viral Vector System Mediating Long Term Gene Expression in Mouse Lung and Liver," *Mol. Therapy*;5:S323, Amer. Soc. Gene Therapy, Abstract, 2002, 1 pg.

Belur et al., "Hyperoxia-induced Lung Injury: Treatment with a Heme Oxygenase-1 Transgene Mediated by the Sleeping Beauty Transposon System," Amer. Soc. Gene Therapy, Washington D.C., Abstract, Jun. 6-10, 2003, 1 pg.

Belur et al., "Gene Insertion and Long-Term Expression in Lung Mediated by the *Sleeping Beauty* Transposon System," *Mol. Therapy*, Sep. 2003;8(3):501-507.

Bestor, "Transposons Reanimated in Mice," *Cell*,:322-325. [Epub DOI:10.1016/j.cell. Jul. 24, 2005].

Bettinger et al., "Size Reduction of Galactosylated PEI/DNA Complexes Improves Lectin-Mediated Gene Transfer into Hepatocytes," *Bioconjugate Chem.*, 1999; 10:558-561.

Carlson et al., "Germline Transposon Mutagenesis of Mouse Using the Sleeping Beauty Transposon System," Mouse Molecular Genetics Meeting, New York, NY, Abstract, Aug. 2002, 1 pg.

Carlson et al., "Transposon Mutagenesis of the Mouse Germline," *Genetics*, Sep. 2003;165: 243-256.

Carlson et al., "Somatic integration of an oncogene-harboring *Sleeping Beauty* transposon models liver tumor development in the mouse," *PNAS*, Nov. 22, 2005; 102(47): 17059-17064. [Epub Nov. 14, 2005].

Carlson et al., "Insertional Mutagenesis in Mice: New Perspectives and Tools," *Nat. Rev. Genet.*, Jul. 2005; 6(7):568-580.

Chen et al., "Gene 'Knockdown' Approaches Using Unconventional Antisense Oligonucleotides," *Fish Development and Genetics, The Zebrafish and Medaka Models*, Hackensack, NJ, 2004, vol. 2, Chap.13:454-475.

Clark et al., "Sleeping Beauty Goes Fishing: Insertional Mutagenesis Screens Using Transposons," Cold Spring Harbor Meeting on Zebrafish Genetics and Development, CSH Laboratory, NY, Abstract, Apr. 26-30, 2000, 1 pg.

Clark et al., "Sleeping Beauty Transposons for Gene Discovery and Analysis," International Zebrafish Meeting, Madison, WI, Abstract, Jun. 12-16, 2002, 1 pg.

Clark et al., "Transposon Vectors for Gene-Trap Insertional Mutagenesis in Vertebrates," *Genesis*, 2004;39:225-233.

Collier et al., "Cancer gene discovery in solid tumours using transposon-based somatic mutagenesis in the mouse," *Nature*, Jul. 14, 2005; 436(7048):272-276.

Collier et al., "Hopping around the Tumor Genome: Transposons for Cancer Gene Discovery," *Cancer Res.*, Nov. 1, 2005; 65(21):9607-9610.

Collier et al., "Transforming science: cancer gene identification," *Curr. Opin. Genet. Dev.*, Feb. 2006; 16(1):23-29. [Epub Dec. 1, 2005].

Converse et al., "Sleeping Beauty-mediated Transposition I Cultured Human Lung and Liver Cells and Murine Hematopoietic Cells," *Mol. Therapy;*3:S64, Amer. Soc. Gene Therapy, Seattle, WA, Abstract, May 30-Jun. 3, 2001, 1 pg.

Converse et al., "Counterselection and Co-Delivery of Transposon and Transposase Functions for *Sleeeping Beauty*-Mediated Transposition in Cultured Mammalian Cells," *Biosci. Rep.*, Dec. 2004; 24(6):577-594.

Cui et al., "Structure-Function Analysis of the Inverted Terminal Repeats of the Sleeping Beauty Transposon," *J. Mol. Biol.*, 2002; 318:1221-1235.

Cui et al., "RecA-mediated, Targeted Mutagenesis in Zebrafish," *Mar. Biotechnol.*, 2003; 5:174-184.

Davidson et al., "Sleeping Beauty: An Efficient Method for Gene Delivery in Zebrafish," International Zebrafish Meeting, Madison, WI, Abstract, Jun. 12-16, 2002, 1 pg.

Davidson et al., "Efficient gene delivery and gene expression in zebrafish using the *Sleeping Beauty* transposon," *Dev. Biol.*, 2003;263:191-202.

Ding et al., "Efficient Transposition of the *piggyBac* (PB) Transposon in Mammalian Cells and Mice," *Cell*, Aug. 12, 2005; 122:473-483. [Epub DOI 10.1016/j.cell. Jul. 13, 2005].

Dupuy et al., "Transposition and Gene Disruption in the Male Germline of the Mouse," *Genesis*, 2001;30:82-88. [received Apr. 27, 2001; accepted May 16, 2001; online pub'l Jun. 13, 2001; journal pub'l Jun. 2001].

Dupuy et al., "Mammalian germ-line transgenesis by transposition," *Proc. Natl. Acad. Sci. USA*, 2002;99(7):4495-4499.

Dupuy et al., "Mammalian mutagenesis using a highly mobile somatic *Sleeping Beauty* transposon system," *Nature*, Jul. 14, 2005; 436(7048):221-226.

Ehrhardt et al., "A Direct Comparison of Two Nonviral Gene Therapy Vectors for Somatic Integration: *In Vivo* Evaluation of the Bacteriophage Integrase Øc31 and the *Sleeping Beauty* Transposase," *Mol. Ther.*, May, 2005; 11(5):695-706.

Eisenstein, "Wake-up call for *Sleeping Beauty*," *Nat. Methods*, Sep. 2005; 2(9):637.

Ekker, Stephen C., "Insertional Mutagenesis in Zebrafish by SB Transposons," Grant Abstract, Grant No. 5R01DA014546-04 [online]. National Institute on Drug Abuse, project dates May 1, 2001-Mar. 31, 2006 [retrieved on Feb. 13, 2006]. Retrieved from the Internet: URL:http://crisp.cit.nih.gov/CRISP_LIB. getdoc?textkey=6736301&p_grant_num=5R01D . . . 2 pgs.

Ekker, Stephen C., "Insertional Mutagenesis in Zebrafish by SB Transposons," Grant Abstract, Grant No. 5R01DA014546-05 [online]. National Institute on Drug Abuse, project dates May 1, 2001-Mar. 31, 2006 [retrieved on Feb. 13, 2006]. Retrieved from the Internet: URL: http://crisp.cit.nih.gov/CRISP_LIB. getdoc?textkey=6881460&p_grant_num=5R01D . . . 2 pgs.

Ekker et al., "The Sleeping Beauty Transposon System in Zebrafish—its Activity in the 21st Century," Cold Spring Harbor Meeting on Zebrafish Genetics and Development, CSH Laboratory, NY, Abstract, Apr. 26-30, 2000, 1 pg.

Essner, Jeffrey J., "Angiogenesis Targets for Therapeutic Development," Grant Abstract, Grant No. 1R43CA108117-01 [online]. National Cancer Institute, project dates Jun. 4, 2004-Nov. 30, 2004 [retrieved on Feb. 13, 2006]. Retrieved from the Internet: URL: http://crisp.cit.nih.gov/CRISP_LIB.getdoc?textkey=6790744 &p_grant_num=1R43C . . . 2 pgs.

Essner et al. "Awakening gene therapy with Sleeping Beauty transposons," *Curr. Opin. Pharmacol.*, 2005; 5:513-519.

Geurts et al., "Gene Transfer into Genomes of Human Cells by the *Sleeping Beauty* Transposon System," *Mol. Therapy*, Jul. 2003; 8(1):108-117.

Grabher et al., "Transposon-mediated enhancer trapping in medaka," *Gene*, 2003;322:57-66.

Grabher et al., "Efficient activation of gene expression using a heat-shock inducible Gal4/Vp16-UAS system in medaka," *BMC Biotechnol.*, Oct. 26, 2004; 4(26):1-6.

Hackett, "Development of Genetic Tools for Genomic Analyses and Transgenesis in Fish,"Biotechnology-Aquaculture Interface, USDA meeting, http://nps.ars.usda.gov/static/ arsoibiotecws2001/contributions/Hackettrev.htm, Shepardstown, WV, Abstract, Mar. 5-7, 2001, 5 pgs.

Hackett, "From Tissue Culture to Whole Animals: Development of Genetic Tools for Genomic Analyses and Transgenesis in Fish," Generation of new Marine cell lines and transgenic fish meeting, Mount Desert Island Biological Laboratory, Bar Harbor, ME, Abstract, May 4-6, 2001, 2 pgs.

Hackett, "The R's of the Life Sciences: from Repair Replication in Bacteria to Ribosomal RNA and Retroviruses in Animals to Recombination in Zebrafish," Workshop on DNA repair and related DNA transactions, Fallen Leaf Lake, CA, Abstract, Oct. 4-7, 2001, 1 pg.

Hackett, "The Sleeping Beauty Transposon System for Non-viral Gene Delivery into Animal Cells for Long-term Expression," Biophex 2002, Santa Clara, CA, Abstract, Sep. 22-23, 2002, 1 pg.

Hackett, "The Sleeping Beauty Transposon System for Non-viral Gene Delivery into Animal Cells for Long-term Expression," Biophex 2002, San Diego, CA, Abstract, Dec. 9-10, 2002, 8 pgs.

Hackett, Perry B., "Sleeping Beauty-Mediated Gene Therapy for Hemophilia," Grant Abstract, Grant No. 2R44HL072539-02A1 [online]. National Heart, Lung and Blood Institute, project dates Feb. 1, 2003-Dec. 31, 2006 [retrieved on Feb. 13, 2006]. Retrieved from the Internet: URL:http://crisp.cit.nih.gov/CRISP_LIB. getdoc?textkey=6883402&p_grant_num=2R44H . . . 2 pgs.

Hackett, Perry, B., "Transposon-Mediated Gene Therapy for Fanconi Anemia," Grant Abstract, Grant No. 1R43HL076908-01 [online]. National Heart, Lung and Blood Institute, project dates Apr. 1, 2004-Mar. 31, 2005 [retrieved on Feb. 13, 2006]. Retrieved from the Internet: URL:http://crisp.cit.nih.gov/CRISP_LIB. getdoc?textkey=6787819&p_grant_num=1R43H . . . 2 pgs.

Hackett et al., "Activity of the Sleeping Beauty Transposon System in Zebrafish and Other Vertebrate Cells," NIH Workshop on Genomic and Genetic Tools for the Zebrafish, NIH, Abstract, May 10-11, 1999, 1 pg.

Hackett et al., "Activity of the Sleeping Beauty Transposon System in Zebrafish and Mammalian Cells," Cold Spring Harbor Varmus Meeting, CSH Laboratory, NY, Abstract, Dec. 17-20, 1999, 1 pg.

Hackett et al., "New Genetic Engineering Methods and Goals for Improvement of Fish and Their Interactions with the Environment," World Aquaculture Symposium, Nice, France, Abstract, May 2-7, 2000, 1 pg.

Hackett et al., "Sleeping Beauty: A DNA-Based Transposon System for Gene Delivery and Gene Discovery in Vertebrates," Amer. Soc. Gene Therapy, Denver, CO, Abstract, May 31-Jun. 4, 2000, 1 pg.

Hackett et al., "Sleeping Beauty: A Transposon System for Gene Delivery in Vertebrates," Frontiers in Nephrology Symposium—Gene Therapy, Boulder Creek, CO, Abstract, Jun. 5-6, 2000, 1 pg.

Hackett et al., "New Genetic Engineering Methods for Improvement of Fish," International Marine Biotechnology Conference, Townsville, Australia, Abstract, Sep. 29-Oct. 5, 2000, 1 pg.

Hackett et al., "Applications of the Sleeping Beauty Transposon System in Fish," 3rd IUBS Symposium on Molecular Aspects of Fish Genomes and Development, Singapore, Abstract, Feb. 19-21, 2001, 1 pg.

Hackett et al., "Development of a Transposon System for Gene Delivery and Gene-tagging in Vertebrates," International Symposium for Innovative Technologies, Minneapolis, MN, Abstract, May 2000, 1 pg.

Hackett et al., "Applications of the Sleeping Beauty Transposon System in Animals,", *Dev. Grow. Diff.;43*S27, 14th Intl. Congress of Developmental Biology, Kyoto, Japan, Abstract, Jul. 8-12, 2001, 1 pg.

Hackett et al., "Structural and Functional Studies with the Sleeping Beauty Transposon System Vertebrate," UC Davis Transgenic Animal Research Conference III, Tahoe City, CA, Abstract, Sep. 9-12, 2001, 2 pgs.

Hackett et al., "Structure/Function Studies with the Sleeping Beauty Transposon System," 24th Annual Meeting of the Molecular Biology Society of Japan, Yokohama, Japan, Abstract, Dec. 10, 2001, 1 pg.

Hackett et al., "Development of the Sleeping Beauty Transposon System for Non-viral Gene Therapy. Angiogenesis in Cancer and Other Diseases from Genes to Function to Therapy," Keystone Symposium, Banff, Canada, Abstract, Feb. 8-13, 2002, 1 pg.

Hackett et al., "Structural and functional studies with the *Sleeping Beauty* transposon system in vertebrate," *Transgenic Research*, Abstracts of the 3rd UC Davis Transgenic Animal Research Conference, 2002;11:73-94.

Hackett et al., "Application of New Genetic Tools for Understanding Gene Function in Fish," Workshop on Fish Genetics and Development, Wuhan, China, Abstract, Jun. 1-5, 2003, 1 pg.

Hackett et al., "Applications of Transposable Elements in Fish for Transgenesis and Functional Genomics," *Fish Development and Genetics, The Zebrafish and Medaka Models*, Hackensack, NJ, 2004, vol. 2, Chap.16:532-580.

Hackett et al., "*Sleeping Beauty* Transposon-Mediated Gene Therapy for Prolonged Expression," *Adv. Genet.*, 2005; 54:189-232.

He et al., "Insulin expression in livers of diabetic mice mediated by hydrodynamics- based administration," *World J. Gastroenterol.*, 2004;10:567-572.

Heggestad et al., "Transposon-based RNAi delivery system for generating knockdown cell lines," *Biochem. Biophys. Res. Comm.*, 2004;316:643-650.

Hermanson et al., "*Sleeping Beauty* Transposon for Efficient *Gene Delivery*," *Methods in Cell Biology*, 2004, San Diego, CA, vol. 77:349-362.

Horie et al., "Characterization of *Sleeping Beauty* Transposition and Its Application to Genetic Screening in Mice," *Mol. Cell. Biol.*, Dec. 2003;23(24): 9189-9207.

Huang et al., "Stable gene transfer and expression in human primary T cells by the *Sleeping Beauty* transposon system," *Blood*, Jan. 15, 2006; 107(2):483-491. [Epub Sep. 27, 2005, DOI 10.1182/Blood-2005-05-2133].

Ivics et al., "Transposable Elements for Transgenesis and Insertional Mutagenesis in Vertebrates: a Contemporary Review of Experimental Strategies," *Methods Mol. Biol., Mobile Genetic Elements*, Totowa, NJ, 2004, vol. 260:255-276.

Ivics et al., "The *Sleeping Beauty* Transposable Element: Evolution, Regulation and Genetic Applications," *Curr. Issues Mol. Biol.*, 2004;6:43-55.

Ivics et al., "A whole lotta jumpin goin' on: new transposon tools for vertebrate functional genomics," *Trends Genet.*, Jan. 2005; 21(1):8-11.

Izsvák et al., "Short Inverted-Repeat Transposable Elements in Teleost Fish and Implications for a Mechanism of Their Amplification" *J. Mol. Evol.*, 1999;48:13-21.

Izsvák et al., "Healing the Wounds Inflicted by *Sleeping Beauty* Transposition by Double-Strand Break Repair in Mammalian Somatic Cells," *Mol. Cell*, Jan. 30, 2004;13:279-290.

Izsvák et al., "*Sleeping Beauty* Transposition: Biology and Applications for Molecular Therapy," *Mol. Ther.*, Feb. 2004;9(2):147-156.

Izsvák et al., "*Sleeping Beauty* hits them all: transposon-mediated saturation mutagenesis in the mouse germline," *Nat. Methods*, Oct. 2005; 2(10):735-737.

Karsi et al., "Effects of Insert Size on Transposition Efficiency of the *Sleeping Beauty* Transposon in Mouse Cells," *Mar. Biotechnol.*, 2001;3:241-245.

Kaufman et al., "Remobilization of Sleeping Beauty Transposons in Zebrafish," Cold Spring Harbor Meeting on Zebrafish Genetics and Development, CSH Laboratory, NY, Abstract, Apr. 26-30, 2000, 1 pg.

Kawakami et al., "Excision of the *Tol2* transposable element of the medaka fish, *Oryzias latipes*, in zebrafish, *Danio rerio*," *Gene*, 1998;225:17-22.

Kawakami et al., "A Transposon-Mediated Gene Trap Approach Identifies Developmentally Regulated Genes in Zebrafish," *Dev. Cell*, Jul. 2004; 7:133-144.

Kawakami, "Transposon Tools and Methods in Zebrafish," *Dev. Dyn.*, 2005; 234:244-254.

Keng et al., "Region-specific saturation germline mutagenesis in mice using the *Sleeping Beauty* transposon system," *Nat. Methods*, Oct. 2005; 2(10):763-769.

Kren et al., "In Utero Delivery and Long-term Expression of GFP in Liver Mediated by the Sleeping Beauty Transposon System," *Mol. Therapy;3*:S138, Amer. Soc. Gene Therapy, Seattle, WA, Abstract, May 30-Jun. 3, 2001, 1 pg.

Kren et al., "Gene Therapy as an Alternative to Liver Transplantation," *Liver Transpl.*, Dec. 2002;8(12):1089-1108.

Kren et al., "Hepatocyte-targeted delivery of *Sleeping Beauty* mediates efficient gene transfer *in vivo*," *Gene Ther. Mol. Biol.*, Nov. 2003;7:229-238.

Largaespada, "Generating and manipulating transgenic animals using transposable elements," *Reprod. Biol. Endocrinol.*, Nov. 7, 2003; 1(80):1-10.

Larson et al., "Expression of *VE-cadherin* in Zebrafish Embryos: A New Tool to Evaluate Vascular Development," *Dev. Dyn.*, 2004; 231:204-213.

Liu et al., "In Vivo Transposition Assay of Sleeping Beauty Transposon in Zebrafish," Cold Spring Harbor Meeting on Zebrafish Genetics and Development, CSH Laboratory, NY, Abstract, Apr. 26-30, 2000, 1 pg.

Liu et al., "Improved Sleeping Beauty Transposon System for Use in Gene Therapy," *Mol. Therapy;5*:S333, Amer. Soc. Gene Therapy, Boston, MA, Abstract, Jun. 5-9, 2002, 1 pg.

Liu et al., "Improvements in the Sleeping Beauty Transposon System for Use in Gene Transfer," International Zebrafish Meeting, Madison, WI, Abstract, Jun. 12-16, 2002, 1 pg.

Liu et al., "Endothelial Targeting of the *Sleeping Beauty* Transposon within Lung," *Mol. Ther.*, Jul. 2004;10(1):97-105.

Liu et al., "Excision of *Sleeping Beauty* transposons: parameters and applications to gene therapy," *J. Gene Med.*, 2004;6:574-583.

Liu et al., "Target-site Preferences of *Sleeping Beauty* Transposons," *J. Mol. Biol.*, 2005; 346:161-173.

Masuda et al., "Transposon-independent increase of transcription by the Sleeping Beauty transposase," *Biochem. Biophys. Res. Comm.*, 2004;317:796-800.

Mikkelsen et al., "Helper-Independent *Sleeping Beauty* Transposon-Transposase Vectors for Efficient Nonviral Gene Delivery and Persistent Gene Expression *in Vivo*," *Mol. Therapy*, Oct. 2003;8(4):654-665.

Miskey et al., "The *Frog Prince:* a reconstructed transposon from *Rana pipiens* with high transpositional activity in vertebrate cells," *Nucl. Acids Res.*, 2003;31(23):6873-6881.

Miskey et al., "DNA transposons in vertebrate functional genomics," *Cell Mol. Life Sci.*, 2005; 62:629-641.

Montini et al., "*In Vivo* Correction of Murine Tyrosinemia Type I by DNA-Mediated Transposition," *Mol. Therapy*, Dec. 2002;6(6):759-769.

"Mouse Transposon Insertion Database" [online]. University of Minnesota, Database Access [retrieved on Dec. 20, 2004]. Retrieved from the Internet:<URL:http://mouse.ccgb.umn.edu/ transposon/>; 1 pg.

Ohlfest et al., "Integration and Long-Term Expression in Xenografted Human Glioblastoma Cells Using a Plasmid-Based Transposon System," *Mol. Therapy*, Aug. 2004;10(2):260-268.

Ohlfest et al., "Phenotypic correction and long-term expression of factor VIII in hemophilic mice by immunotolerization and nonviral gene transfer using the *Sleeping Beauty* transposon system," *Blood*, Apr. 1, 2005; 105(7):2691-2698.

Ohlfest et al., "Combinatorial Antiangiogenic Gene Therapy by Nonviral Gene Transfer Using the *Sleeping Beauty* Transposon Causes Tumor Regression and Improves Survival in Mice Bearing Intracranial Human Glioblastoma," *Mol. Ther.*, Nov. 2005; 12(5):778-788. [Epub doi:10.1016/j.ymthe.2005.07.689, Sep. 16, 2005].

Ortiz-Urda et al., "Sustainable correction of junctional epidermolysis bullosa via transposon-mediated nonviral gene transfer," *Gene Therapy*, 2003;10:1099-1104.

Park et al., "DNA methylation of Sleeping Beauty with Transposition into the mouse genome," *Genes to Cells*, 2005; 10:763-776.

Richardson et al., "Strategies for Hepatic Gene Correction," *J. Drug Target*, 2002;10(2): 133-141.

Roberg-Perez et al., "MTID: a database of *Sleeping Beauty* transposon insertions in mice," *Nucl. Acids Res.*, 2003;31(1):78-81.

Rumpold et al., "RNAi-mediated knockdown of P-glycoprotein using a transposon-based vector system durably restores imatinib sensitivity in imatinib-resistant CML cell lines," *Exp. Hematol.*, 2005; 33:767-775.

Score et al., "*Sleeping Beauty*-Mediated Transposition and Long-Term Expression *in Vivo:* Use of the LoxP/Cre Recombinase System to Distinguish Transposition-Specific Expression," *Mol. Ther.* [Epub doi:10.1016/ j.ymthe.2005.10.015].

Starr et al., "Cancer Gene Discovery Using the Sleeping Beauty Transposon," *Cell Cycle*, 4(12):e1-e5. [Epub Dec. 2005].

Tada et al., "Long-Term Reduction of Serum Bilirubin Levels in Gunn Rats by Retroviral Gene Transfer In Vivo," *Liver Transpl. Surg.*, Jan. 1998; 4(1):78-88.

Tolar et al., "Real-Time *In Vivo* Imaging of Stem Cells Following Transgenesis by Transposition," *Mol. Ther.*, Jul. 2005; 12(1):42-48.

Vigdal et al., "Common Physical Properties of DNA Affecting Target Site Selection of *Sleeping Beauty* and other Tc1/*mariner* Transposable Elements," *J. Mol. Biol.*, 2002;323(3):441-452.

Wacnik et al., "Tumor-induced mechanical hyperalgesia involves CGRP receptors and altered innervation and vascularization of DsRed2 fluorescent hindpaw tumors," *Pain*, 2005; 115(1-2):95-106.

Wadman et al., "Fishing for Answers with Transposons," *Mar. Biotechnol.*, May-Jun. 2005; 7:135-141.

Weiser et al., "Sleeping Beauty awakens," *Nature*, Jul. 14, 2005; 436(7048): 184-186.

Whitley, Chester B., "Gene Therapy for Metabolic Disorders," Grant Abstract, Grant No. 2P01HD032652-09A1 [online]. National Institute of Child Health and Human Development, project dates Jan. 1, 1997-Dec. 31, 2008 [retrieved on Feb. 13, 2006]. Retrieved from the Internet: URL:http://crisp.cit.nih.gov/CRISP_LIB.getdoc?textkey =6708516 &p_grant_num=2P01H . . . 2 pgs.

Wilber et al., "RNA as a Source of Transposase for *Sleeping Beauty*-Mediated Gene Insertion and Expression in Somatic Cells and Tissues," *Mol. Ther.*, Dec. 12, 2005, [Epub ahead of print; doi:10.1016/j.ymthe.2005.10.015]:1-6.

Wilber et al., "Dynamic Gene Expression After Systemic Delivery of Plasmid DNA as Determined by *In Vivo* Bioluminescence Imaging," *Hum. Gene Ther.*, Nov. 2005; 16:1325-1332. [Epub Sep. 26, 2005].

Wilson et al., "Functional zinc finger/*sleeping beauty* transposase chimeras exhibit attenuated overproduction inhibition," *FEBS Lett.*, Nov. 7, 2005; 579(27):6205-6209. [Epub Oct. 17, 2005].

Wu et al., "Integration target site selection for retroviruses and transposable elements," *Cell Mol. Life Sci.*, 2004; 61:2588-2596.

Yant et al., "Nonhomologous-End-Joining Factors Regulate DNA Repair Fidelity during *Sleeping Beauty* Element Transposition in Mammalian Cells," *Mol. Cell. Biol.*, Dec. 2003;23(23):8505-8518.

Yant et al., "Mutational Analysis of the N-Terminal DNA-Binding Domain of Sleeping Beauty Transposase: Critical Residues for DNA Binding and Hyperactivity in Mammalian Cells," *Mol. Cell Biol.*, Oct. 2004;24(20):9239-9247.

Yant et al., "High-Resolution Genome-Wide Mapping of Transposon Integration in Mammals," *Mol. Cell. Biol.*, Mar. 2005; 25(6):2085-2094.

York, "Sleeping beauty offers new method to find cancer genes," *Lancet Oncol.*, Aug. 2005; 6(8):545.

Yusa et al., "Enhancement of *Sleeping Beauty* Transposition by CpG Methylation: Possible Role of Heterochromatin Formation," *Mol. Cell Biol.*, May 2004;24(9):4004-4018.

Zanta et al., "*In Vitro* Gene Delivery to Hepatocytes with Galactosylated Polyethylenimine," *Bioconjugate Chem.*, 1997; 8:839-844.

Zayed et al., "The DNA-bending protein HMGB1 is a cellular cofactor of *Sleeping Beauty* transposition," *Nucl. Acids Res.*, 2003;31(9):2313-2322.

Zayed et al., "Development of Hyperactive *Sleeping Beauty* Transposon Vectors by Mutational Analysis," *Mol. Ther.*, Feb. 2004; 9(2):292-304.

\* cited by examiner

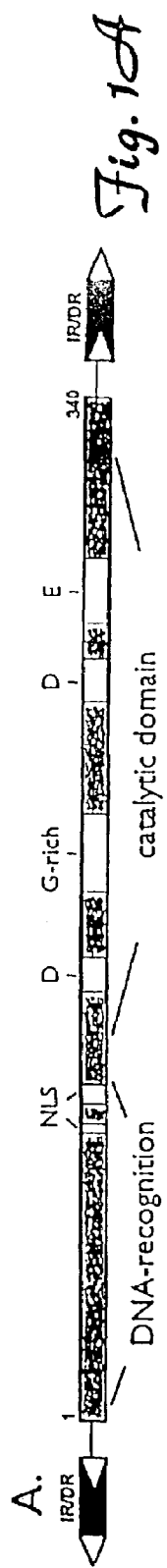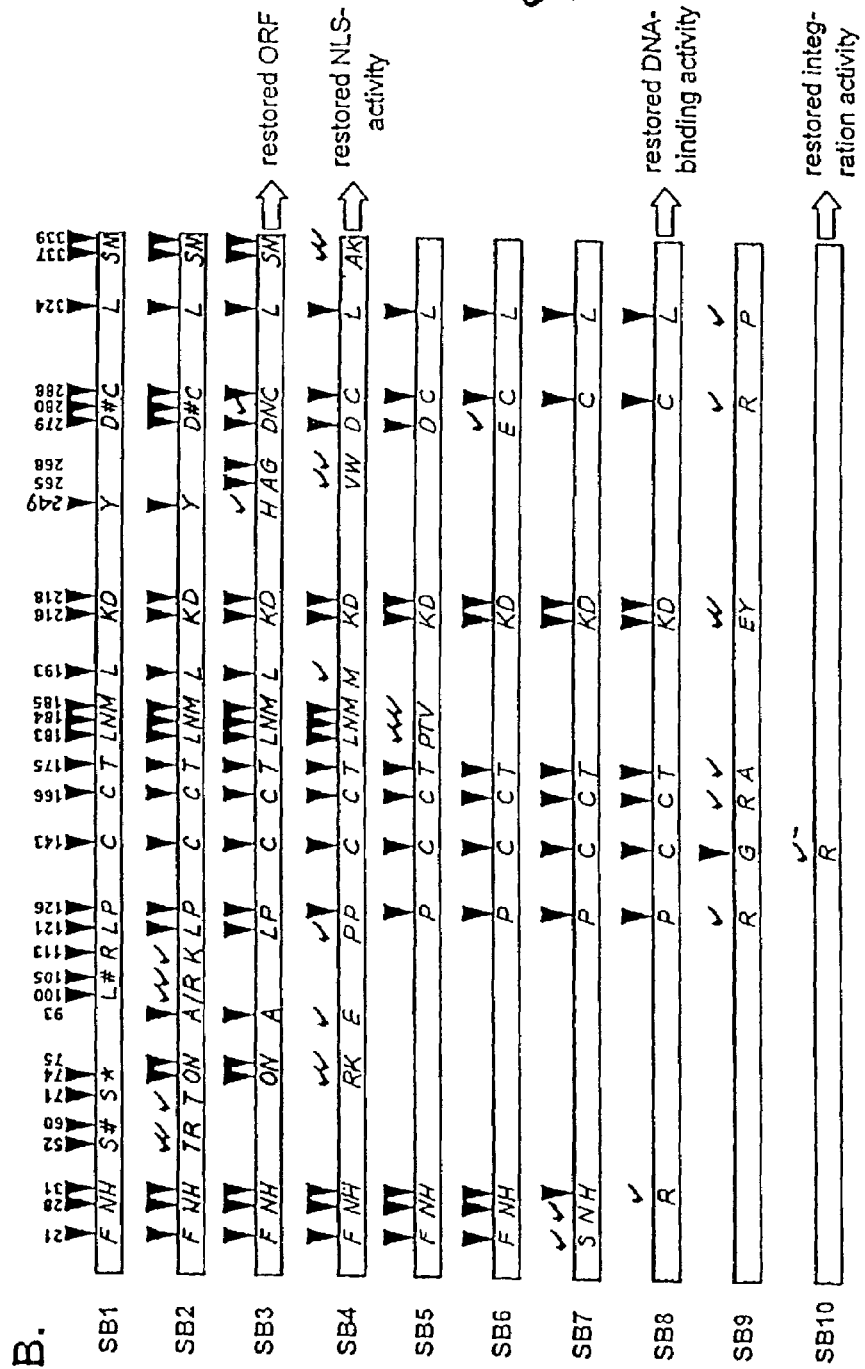
Fig. 1A
Fig. 1B (SEQ ID NO:3)

```
   1  ATGGGAAAA TCAAAAGAAA TCAGCCAAGA CCTCAGAAAA
      TACCCTTTT AGTTTTCTTT AGTCGGTTCT GGAGTCTTTT

51  AAAATTGTAG ACCTCCACAA GTCTGGTTCA TCCTTGGGAG CAATTTCCAA
      TTTTAACATC TGGAGGTGTT CAGACCAAGT AGGAACCCTC GTTAAAGGTT

101  ACGCCTGAAA GTACCACGTT CATCTGTACA AACAATAGTA CGCAAGTATA
      TGCGGACTTT CATGGTGCAA GTAGACATGT TTGTTATCAT GCGTTCATAT

151  AACACCATGG GACCACGCAG CCGTCATACC GCTCAGGAAG GAGACGCGTT
      TTGTGGTACC CTGGTGCGTC GGCAGTATGG CGAGTCCTTC CTCTGCGCAA

201  CTGTCTCCTA GAGATGAACG TACTTTGGTG CGAAAAGTGC AAATCAATCC
      GACAGAGGAT CTCTACTTGC ATGAAACCAC GCTTTTCACG TTTAGTTAGG

251  CAGAACAACA GCAAAGGACC TTGTGAAGAT GCTGGAGGAA ACAGGTACAA
      GTCTTGTTGT CGTTTCCTGG AACACTTCTA CGACCTCCTT TGTCCATGTT

301  AAGTATCTAT ATCCACAGTA AAACGAGTCC TATATCGACA TAACCTGAAA
      TTCATAGATA TAGGTGTCAT TTTGCTCAGG ATATAGCTGT ATTGGACTTT

351  GGCCGCTCAG CAAGGAAGAA GCCACTGCTC CAAAACCGAC ATAAGAAAGC
      CCGGCGAGTC GTTCCTTCTT CGGTGACGAG GTTTTGGCTG TATTCTTTCG

401  CAGACTACGG TTTGCAACTG CACATGGGGA CAAAGATCGT ACTTTTTGGA
      GTCTGATGCC AAACGTTGAC GTGTACCCCT GTTTCTAGCA TGAAAAACCT

451  GAAATGTCCT CTGGTCTGAT GAAACAAAAA TAGAACTGTT TGGCCATAAT
      CTTTACAGGA GACCAGACTA CTTTGTTTTT ATCTTGACAA ACCGGTATTA

501  GACCATCGTT ATGTTTGGAG GAAGAAGGGG GAGGCTTGCA AGCCGAAGAA
      CTGGTAGCAA TACAAACCTC CTTCTTCCCC CTCCGAACGT TCGGCTTCTT

551  CACCATCCCA ACCGTGAAGC ACGGGGGTGG CAGCATCATG TTGTGGGGGT
      GTGGTAGGGT TGGCACTTCG TGCCCCCACC GTCGTAGTAC AACACCCCCA

601  GCTTTGCTGC AGGAGGGACT GGTGCACTTC ACAAAATAGA TGGCATCATG
      CGAAACGACG TCCTCCCTGA CCACGTGAAG TGTTTTATCT ACCGTAGTAC

651  AGGAAGGAAA ATTATGTGGA TATATTGAAG CAACATCTCA AGACATCAGT
      TCCTTCCTTT TAATACACCT ATATAACTTC GTTGTAGAGT TCTGTAGTCA

701  CAGGAAGTTA AAGCTTGGTC GCAAATGGGT CTTCCAAATG GACAATGACC
      GTCCTTCAAT TTCGAACCAG CGTTTACCCA GAAGGTTTAC CTGTTACTGG

751  CCAAGCATAC TTCCAAAGTT GTGGCAAAAT GGCTTAAGGA CAACAAAGTC
      GGTTCGTATG AAGGTTTCAA CACCGTTTTA CCGAATTCCT GTTGTTTCAG

801  AAGGTATTGG AGTGGCCATC ACAAAGCCCT GACCTCAATC CTATAGAAAA
      TTCCATAACC TCACCGGTAG TGTTTCGGGA CTGGAGTTAG GATATCTTTT

851  TTTGTGGGCA GAACTGAAAA AGCGTGTGCG AGCAAGGAGG CCTACAAACC
      AAACACCCGT CTTGACTTTT TCGCACACGC TCGTTCCTCC GGATGTTTGG

901  TGACTCAGTT ACACCAGCTC TGTCAGGAGG AATGGGCCAA AATTCACCCA
      ACTGAGTCAA TGTGGTCGAG ACAGTCCTCC TTACCCGGTT TTAAGTGGGT

951  ACTTATTGTG GGAAGCTTGT GGAAGGCTAC CCGAAACGTT TGACCCAAGT
      TGAATAACAC CCTTCGAACA CCTTCCGATG GGCTTTGCAA ACTGGGTTCA

1001  TAAACAATTT AAAGGCAATG CTACCAAATA CTAG.
      ATTTGTTAAA TTTCCGTTAC GATGGTTTAT GATC
```

Fig. 2A

Paired-like domain with Leucine-zipper

```
  1  MGKSKEISQD LRKKIVDLHK SGSSLGAISK RLKVPRSSVQ TIVRKYKHHG
 51  TTQPSYRSGR RVLSPRDER  TLVRKVQINP RTTAKDLVKM LEETGTKVSI
        NLS
101  STVKRVLYRH NLKGRSARKK PLLQNRHKKA RLRFATAHGD KDRTFWRNVL
151  WSDETKIELF GHNDHRYVWR KKGEACKPKN TIPTVKHGGG SEMLWGCFAA
                                         Glycine-rich box
201  GGTGALHKID GIMRKENYVD ILKQHLKTSV RKLKLGRKWV FQMDNDPKHT
251  SKVVAKWLKD NKVKVLEWPS QSPDLNPIEN LWAELKKRVR ARRPTNLTQL
301  HQLCQEEWAK IHPTYCGKLV EGYPKRLTQV KQFKGNATKY * (SEQ ID NO:1)
                                            DD(34)E box
```

*Fig. 2B*

Fig. 4A
Fig. 4B
```
ccagtgggtcagaagtttacatacactaag (SEQ ID NO:39)
|||| ||| |||||||||||| |||
cttgaaagtc..aagtttacatacaataag (SEQ ID NO:40)
```
```
gttgaagtcggaagtttacatacacttagg (SEQ ID NO:37) -salmonid-
|||| ||| ||||||||||| ||| ||||
gtttaaccagaagtttacacacactgtat (SEQ ID NO:38) -zebrafish-
```
Fig. 4C
```
External  tacagttgaagtcggaagtttacatacacttagg (SEQ ID NO:41)
          |||| ||| |||||||||||| |||
Internal  tccagtgg..gtcagaagtttacatacacactagt (SEQ ID NO:42)
```
C.

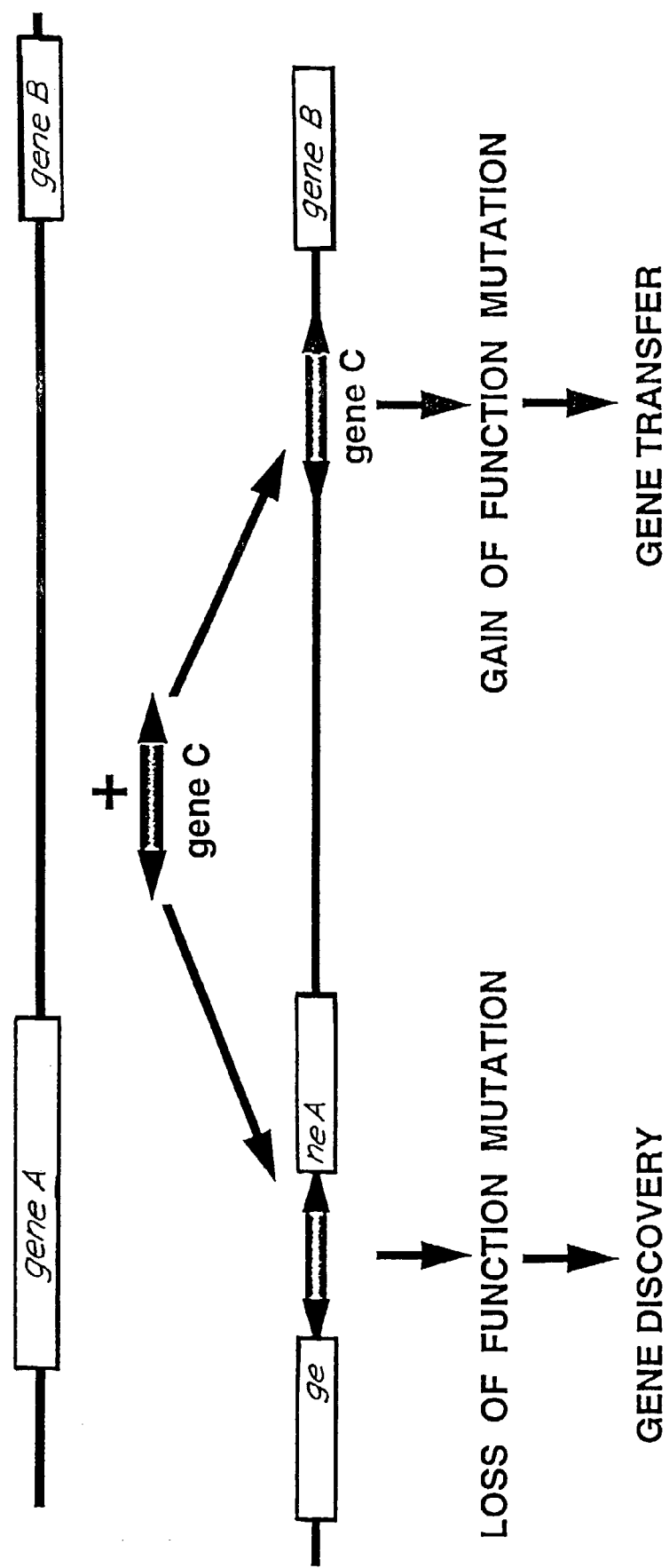

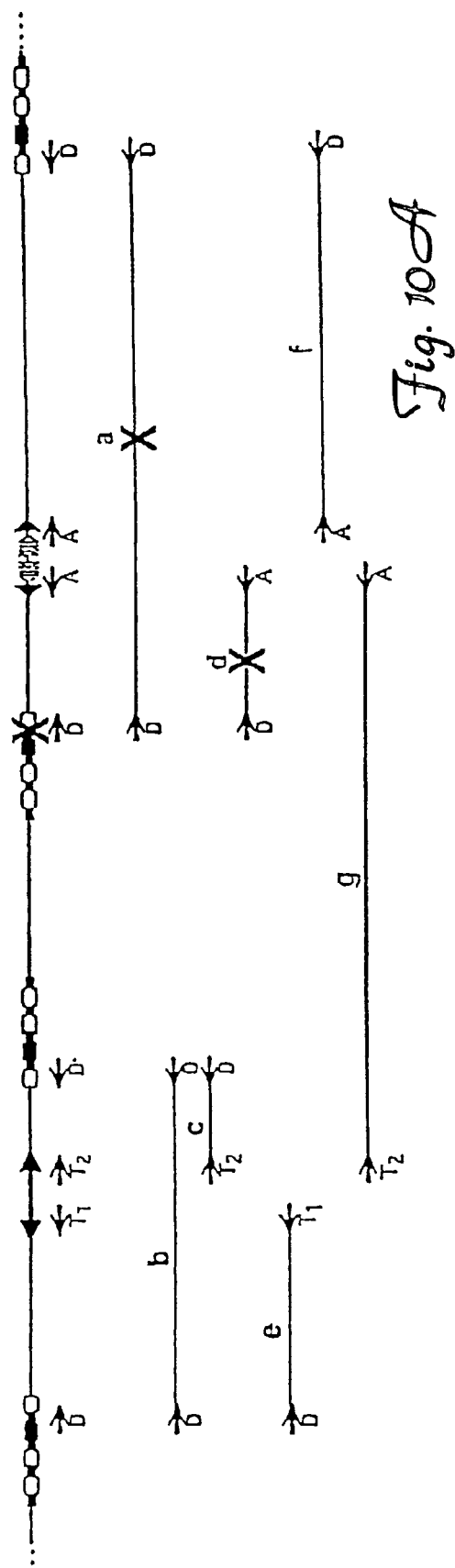
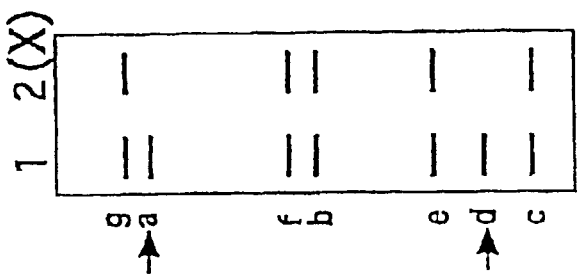
Fig. 10A
Fig. 10B
Generate sequence-tagged sites (STS) by isolation of fragments a and d and place them on a genetic map.

NUCLEIC ACID TRANSFER VECTOR FOR THE INTRODUCTION OF NUCLEIC ACID INTO THE DNA OF A CELL

This is a continuation of application Ser. No. 09/142,593, filed Sep. 10, 1998 (now U.S. Pat. No. 6,489,458), which is the National Stage of International Application No. PCT/US98/04687, filed Mar. 11, 1998, which claims the benefit of U.S. Provisional Application No. 60/040,664, filed Mar. 11, 1997, U.S. Provisional Application No. 60/053,868, filed Jul. 28, 1997, and U.S. Provisional Application No. 60/065,303, filed Nov. 13, 1997, all of which are incorporated herein by reference.

STATEMENT REGARDING GOVERNMENT RIGHTS

This invention was made with government support from the United States Department of Agriculture, USDA Grant No. 92-37205-7842; National Institutes of Health, NIH Grant No. R01-RR0625; and SeaGrant No. USDOC/NA46RG O101-04. The government may have certain rights in this invention.

FIELD OF THE INVENTION

This invention relates to methods for gene expression, mapping genes, mutagenesis, methods for introducing DNA into a host chromosome and to transposons and transposases.

Transposons or transposable elements include a short piece of nucleic acid bounded by repeat sequences. Active transposons encode enzymes that facilitate the insertion of the nucleic acid into DNA sequences.

In vertebrates, the discovery of DNA-transposons, mobile elements that move via a DNA intermediate, is relatively recent (Radice, A. D., et al., 1994. *Mol. Gen. Genet.* 244, 606–612). Since then, inactive, highly mutated members of the Tc1/mariner as well as the hAT (hobo/Ac/Tam) superfamilies of eukaryotic transposons have been isolated from different fish species, *Xenopus* and human genomes (Oosumi et al., 1995. *Nature* 378, 873; Ivics et al. 1995. *Mol. Gen. Genet.* 247, 312–322; Koga et al., 1996. *Nature* 383, 30; Lam et al., 1996. *J. Mol. Biol.* 257, 359–366 and Lam, W. L., et al. *Proc. Natl. Acad. Sci. USA* 93, 10870–10875).

These transposable elements transpose through a cut-and-paste mechanism; the element-encoded transposase catalyzes the excision of the transposon from its original location and promotes its reintegration elsewhere in the genome (Plasterk, 1996 *Curr. Top. Microbiol. Immunol.* 204, 125–143). Autonomous members of a transposon family can express an active transposase, the trans-acting factor for transposition, and thus are capable of transposing on their own. Nonautonomous elements have mutated transposase genes but may retain cis-acting DNA sequences. These cis-acting DNA sequences are also referred to as inverted terminal repeats. Some inverted repeat sequences include one or more direct repeat sequences. These sequences usually are embedded in the terminal inverted repeats (IRs) of the elements, which are required for mobilization in the presence of a complementary transposase from another element.

Not a single autonomous element has been isolated from vertebrates; all transposon-like sequences are defective, apparently as a result of a process called "vertical inactivation" (Lohe et al., 1995 *Mol. Biol. Evol.* 12, 62–72). According to one phylogenetic model (Hartl et al., 1997 *Trends Genet.* 13, 197–201), the ratio of nonautonomous to autonomous elements in eukaryotic genomes increases as a result of the trans-complementary nature of transposition. This process leads to a state where the ultimate disappearance of active, transposase-producing copies in a genome is inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 supra and Kidwell, 1992. *Curr. Opin. Genet. Dev.* 2, 868–873).

The natural process of horizontal gene transfer can be mimicked under laboratory conditions. In plants, transposable elements of the Ac/Ds and Spm families have been routinely introduced into heterologous species (Osborne and Baker, 1995 *Curr. Opin. Cell Biol.* 7, 406–413). In animals, however, a major obstacle to the transfer of an active transposon system from one species to another has been that of species-specificity of transposition due to the requirement for factors produced by the natural host. For this reason, attempts have been unsuccessful to use the P element transposon of *Drosophila melanogaster* for genetic transformation of non-drosophilid insects, zebrafish and mammalian cells (Gibbs et al., 1994 *Mol. Mar. Biol. Biotech.* 3, 317–326; Handler et al., 1993. *Arch. Insect Biochem. Physiol.* 22, 373–384; and R10 et al., 1988 J. Mol. Biol. 200, 411–415). In contrast to P elements, members of the Tc1/mariner superfamily of transposable elements may not be as demanding for species-specific factors for their transposition. These elements are widespread in nature, ranging from single-cellular organisms to humans (Plasterk, 1996, supra). In addition, recombinant Tc1 and mariner transposases expressed in *E. coli* are sufficient to catalyze transposition in vitro (Vos et al, 1996 *Genes. Dev.* 10, 755–761 and Lampe et al., 1996. *EMBO J.* 15, 5470–5479 and PCT International Publication No. WO 97/29202 to Plasterk et al.). Furthermore, gene vectors based on Minos, a Tc1-like element (TcE) endogenous to *Drosophila hydei*, were successfully used for germline transformation of the fly *Ceratitis capitata* (Loukeris et al., 1995 *Science* 270, 2002–2005).

Molecular phylogenetic analyses have shown that the majority of the fish TcEs can be classified into three major types: zebrafish-, salmonid- and *Xenopus* TXr-type elements, of which the salmonid subfamily is probably the youngest and thus most recently active (Ivics et al., 1996, *Proc. Natl. Acad. Sci. USA* 93, 5008–5013). In addition, examination of the phylogeny of salmonid TcEs and that of their host species provides important clues about the ability of this particular subfamily of elements to invade and establish permanent residences in naive genomes through horizontal transfer, even over relatively large evolutionary distances.

TcEs from teleost fish (Goodier and Davidson, 1994 *J. Mol. Biol.* 241, 26–34 and Izsvak et al., 1995. *Mol. Gen. Genet.* 247, 312–322), including Tdr1 in zebrafish (Izsvak et al., 1995, supra) and other closely related TcEs from nine additional fish species (Ivics et al., 1996. *Proc. Natl. Acad. Sci. USA* 93, 5008–5013) are by far the best characterized of a vertebrates. Fish elements, and other TcEs in general, are typified by a single gene encoding a transposase enzyme flanked by inverted repeat sequences. Unfortunately, all the fish elements isolated so far are inactive due to one or more mutations in the transposase genes.

Methods for introducing DNA into a cell are known. These include, but are not limited to, DNA condensing reagents such as calcium phosphate, polyethylene glycol, and the like), lipid-containing reagents, such as liposomes, multi-lamellar vesicles, and the like, and virus-mediated strategies. These methods all have their limitations. For example, there are size constraints associated with DNA condensing reagents and virus-mediated strategies. Further, the amount of nucleic acid that can be introduced into a cell is limited in virus strategies. Not all methods facilitate integration of the delivered nucleic acid into cellular nucleic acid and while DNA condensing methods and lipid-containing reagents are relatively easy to prepare, the incorporation of nucleic acid into viral vectors can be labor intensive. Moreover, virus-mediated strategies can be cell-type or tissue-type specific and the use of virus-mediated strategies can create immunologic problems when used in vivo.

There remains a need for new methods for introducing DNA into a cell, particularly methods that promote the efficient integration of nucleic acid fragments of varying sizes into the nucleic acid of a cell, particularly the integration of DNA into the genome of a cell.

SUMMARY OF THE INVENTION

We have developed a DNA-based transposon system for genome manipulation in vertebrates. Members of the Tc1/mariner superfamily of transposons are prevalent components of the genomes of teleost fish as well as a variety of other vertebrates. However, all the elements isolated from nature appear to be transpositionally inactive. Molecular phylogenetic data were used to identify a family of synthetic, salmonid-type Tc1-like transposases (SB) with their recognition sites that facilitate transposition. A consensus sequence of a putative transposase gene was first derived from inactive elements of the salmonid subfamily of elements from eight species of fish and then engineered by eliminating the mutations that rendered these elements inactive. A transposase was created in which functional domains were identified and tested for biochemical functions individually as well as in the context of a full-length transposase. The transposase binds to two binding-sites within the inverted repeats of salmonid elements, and appears to be substrate-specific, which could prevent cross-mobilization between closely related subfamilies of fish elements. SB transposases significantly enhance chromosomal integration of engineered transposons not only in fish, but also in mouse and in human cells. The requirements for specific motifs in the transposase plus specific sequences in the target transposon, along with activity in fish and mammalian cells alike, establishes SB transposase as the first active DNA-transposon system for germline transformation and insertional mutagenesis in vertebrates. In one aspect of this invention, the invention relates to a nucleic acid fragment comprising: a nucleic acid sequence positioned between at least two inverted repeats wherein the inverted repeats can bind to a SB protein and wherein the nucleic acid fragment is capable of integrating into DNA in a cell. In one embodiment nucleic acid fragment is part of a plasmid and preferably the nucleic acid sequence comprises at least a portion of an open reading frame and also preferably at least one expression control region of a gene. In one embodiment, the expression control region is selected from the group consisting of a promoter, an enhancer or a silencer. Preferably the nucleic acid sequence comprises a promoter operably linked to at least a portion of an open reading frame.

In one embodiment the cell is obtained from an animal such as an invertebrate or a vertebrate. Preferred invertebrates include crustacean or a mollusk including, but not limited to a shrimp, a scallop, a lobster, a clam or an oyster. Preferred vertebrate embodiments include fish, birds, and mammal such as those selected from the group consisting of mice, ungulates, sheep, swine, and humans. The DNA of the cell can be the cell genome or extrachromosomal DNA, including an episome or a plasmid.

In one embodiment of this aspect of the invention, at least one of the inverted repeats comprises SEQ ID NO:4 or SEQ ID NO: 5 and preferably the amino acid sequence of the SB protein has at least an 80% amino acid identity to SEQ ID NO: 1. Also preferably, at least one of the inverted repeats comprises at least one direct repeat, wherein the at least one direct repeat sequence comprises SEQ ID NO: 6, SEQ ID NO: 7, SEQ ID NO: 8 or SEQ ID NO:9. A preferred direct repeat is SEQ ID NO:10. Also preferably the nucleic acid fragment includes a direct repeat that has at least an 80% nucleic acid sequence identity to SEQ ID NO: 10.

In another aspect of this invention, the invention relates to a gene transfer system to introduce DNA into the DNA of a cell comprising: a nucleic acid fragment comprising a nucleic acid sequence positioned between at least two inverted repeats wherein the inverted repeats can bind to an SB protein and wherein the nucleic acid fragment is capable of integrating into DNA of a cell; and a transposase or nucleic acid encoding a transposase, wherein the transposase is an SB protein with an amino acid sequence sharing at least an 80% identity to SEQ ID NO:1. In one embodiment, the SB protein comprises SEQ ID NO:1. Alternatively, the SB protein is encoded by DNA that can hybridize to SEQ ID NO:3 under stringent hybridization conditions. In one embodiment, the transposase is provided to the cell as a protein and in another the transposase is provided to the cell as nucleic acid. In one embodiment the nucleic acid is RNA and in another the nucleic acid is DNA. In yet another embodiment, the nucleic acid encoding the transposase is integrated into the genome of the cell. The nucleic acid fragment can be part of a plasmid or a recombinant viral vector. Preferably, the nucleic acid sequence comprises at least a portion of an open reading frame and also preferably, the nucleic acid sequence comprises at least a regulatory region of a gene. In one embodiment the regulatory region is a transcriptional regulatory region and the regulatory region is selected from the group consisting of a promoter, an enhancer, a silencer, a locus-control region, and a border element. In another embodiment, the nucleic acid sequence comprises a promoter operably linked to at least a portion of an open reading frame.

The cells used in this aspect of the invention can be obtained from a variety of sources including bacteria, fungi, plants and animals. In one embodiment, the cells are obtained from an animal; either a vertebrate or an invertebrate. Preferred invertebrate cells include crustaceans or a mollusks. Preferred vertebrates include fish, birds, and mammal such as rodents, ungulates, sheep, swine and humans.

The DNA of the cell receiving the nucleic acid fragment can be a part of the cell genome or extrachromosomal DNA. Preferably, the inverted repeats of the gene transfer system comprise SEQ ID NO:4 or SEQ ID NO:5. Also preferably the amino acid sequence of the SB protein has at least a 80% identity to SEQ ID NO:1 and preferably at least one of the inverted repeats comprises at least one direct repeat and wherein the at least one direct repeat sequence comprises SEQ ID NO:6, SEQ ID NO: 7, SEQ ID NO:8 or SEQ ID NO:9. In one embodiment, the direct repeat has a consensus sequence of SEQ ID NO: 10. In a particularly preferred embodiment, the nucleic acid sequence is part of a library of recombinant sequences and the nucleic acid sequence is introduced into the cell using a method selected from the group consisting of: particle bombardment, electroporation, microinjection, combining the nucleic acid fragment with lipid-containing vesicles or DNA condensing reagents, and incorporating the nucleic acid fragment into a viral vector and contacting the viral vector with the cell.

In another aspect of this invention, the invention relates to nucleic acid encoding an SB protein, wherein the nucleic acid encodes a protein comprising SEQ ID NO:1 or a protein comprising an amino acid sequence with at least 80% identity to SEQ ID NO:1. The nucleic acid encoding the SB protein can be incorporated into a nucleic acid vector, such as a gene expression vector either as a viral vector or as a plasmid. The nucleic acid can be circular or linear. This invention also relates to cells expressing the SB protein.

In one embodiment the cells containing the SB protein cell are obtained from an animal, either a vertebrate or an invertebrate. Preferred vertebrates include fish, birds and mammals. The cells can be obtained from a variety of tissues including pluripotent and totipotent cells such as an oocyte, one or more cells of an embryo, or an egg. In one embodiment, the cell is part of a tissue or organ. In one embodiment, the nucleic acid encoding the SB protein is integrated in the genome of a cell.

The invention also relates to SB protein comprising the amino acid sequence of SEQ ID NO:1.

In addition, the invention relates to a method for producing a transgenic animal comprising the steps of: introducing a nucleic acid fragment and a transposase into a pluripotent or totipotent cell wherein the nucleic acid fragment comprises a nucleic acid sequence positioned between at least two inverted repeats, wherein the inverted repeats can bind to a SB protein and wherein the nucleic acid fragment is capable of integrating into DNA in a cell and wherein the transposase is an SB protein having an amino acid sequence identity of least 80% to SEQ ID NO:1; and growing the cell into an animal. Preferred pluripotent or totipotent cells include an oocyte, a cell of an embryo, an egg and a stem cell. In one embodiment, the introducing step comprises a method selected from the group consisting of: microinjection; combining the nucleic acid fragment with cationic lipid vesicles or DNA condensing reagents; and incorporating the nucleic acid fragment into a viral vector and contacting the viral vector with the cell as well as particle bombardment and electroporation. In another preferred embodiment the viral vector is selected from the group consisting of a retroviral vector, an adenovirus vector, a herpesvirus or an adeno-associated viral vector. Preferred animals used in this method include a mouse, a fish, an ungulate, a bird, or a sheep.

In yet another aspect of this invention, the invention relates to a method for introducing nucleic acid into DNA in a cell comprising the step of: introducing a nucleic acid fragment comprising a nucleic acid sequence positioned between at least two inverted repeats into a cell wherein the inverted repeats can bind to an SB protein and wherein the nucleic acid fragment is capable of integrating into DNA in a cell in the presence of an SB protein. In a preferred embodiment, the method further comprises introducing an SB protein into the cell. In one embodiment, the SB protein has an amino acid sequence comprising at least a 80% identity to SEQ ID NO:1. The SB protein can be introduced into the cell as protein or as nucleic acid, including RNA or DNA. The cell receiving the nucleic acid fragment can already include nucleic acid encoding an SB protein and already express the protein. In a one embodiment, the SB protein is integrated into the cell genome. The SB protein can be stably expressed in the cell or transiently expressed and nucleic acid encoding the SB protein can be under the control of an inducible promoter or under the control of a constitutive promoter. In one aspect of this method, the introducing step comprises a method for introducing nucleic acid into a cell selected from the group consisting of: microinjection; combining the nucleic acid fragment with cationic lipid vesicles or DNA condensing reagents; and incorporating the nucleic acid fragment into a viral vector and contacting the viral vector with the cell. Preferred viral vectors are selected from the group consisting of a retroviral vector, an adenovirus vector or an adeno-associated viral vector. In another aspect of this method, the method includes the step of introducing an SB protein or RNA encoding an SB protein into the cell. The cells used for this method can be pluripotent or a totipotent cell and this invention also relates to transgenic animals produced by this method. Where transgenic animals are produced, the nucleic acid sequence preferably encodes a protein and preferably a protein to be collected from the transgenic animal or a marker protein. The invention also relates to those cells of the transgenic animal expressing the protein encoded by the nucleic acid sequence.

The invention also relates to a SB protein. In one embodiment the protein has the following characteristics: an ability to catalyze the integration of nucleic acid into DNA of a cell; capable of binding to the inverted repeat sequence of SEQ ID NOS 4 or 5; and 80% amino acid sequence identity to SEQ ID NO:1. In another embodiment, the protein has the following characteristics: transposase activity; a molecular weight range of about 35 kD to about 40 kD on about a 10% SDS-polyacrylamide gel; and an NLS sequence, a DNA binding domain and a catalytic domain and wherein the protein has at least about five-fold improvement in the rate for introducing a nucleic acid fragment into the nucleic acid of a cell as compared to the level obtained by non-homologous recombination. Preferred methods for testing the rate of nucleic acid fragment incorporation is provided in the examples.

In yet another aspect, the invention relates to a method for mobilizing a nucleic acid sequence in a cell comprising the steps of: introducing the protein of this invention into a cell housing DNA containing the nucleic acid fragment of this invention, wherein the protein mobilizes the nucleic acid fragment from a first position within the DNA of a cell to a second position within the DNA of the cell. In one embodiment, the DNA of a cell is genomic DNA. In another, the first position within the DNA of a cell is extrachromosomal DNA and in yet another, the second position within the DNA of a cell is extrachromosomal DNA. In a preferred embodiment, the protein is introduced into the cell as RNA.

The invention also relates to a method for identifying a gene in a genome of a cell comprising the steps of: introducing a nucleic acid fragment and an SB protein into a cell, wherein the nucleic acid fragment comprises a nucleic acid sequence positioned between at least two inverted repeats into a cell wherein the inverted repeats can bind to the SB protein and wherein the nucleic acid fragment is capable of integrating into DNA in a cell in the presence of the SB protein; digesting the DNA of the cell with a restriction endonuclease capable of cleaving the nucleic acid sequence; identifying the inverted repeat sequences; sequencing the nucleic acid close to the inverted repeat sequences to obtain DNA sequence from an open reading frame; and comparing the DNA sequence with sequence information in a computer database. In one embodiment, the restriction endonuclease recognizes a 6-base recognition sequence. In another embodiment, the digesting step further comprises cloning the digested fragments or PCR amplifying the digested fragments.

The invention also relates to a stable transgenic vertebrate line comprising a gene operably linked to a promoter, wherein the gene and promoter are flanked by inverted repeats, wherein the inverted repeats can bind to an SB protein. In one embodiment, the SB protein comprises SEQ ID NO:1 or an amino acid sequence with at least 80% homology to SEQ ID NO:1. In one embodiment, the vertebrate is a fish, including a zebrafish and in another the vertebrate is a mouse.

In addition, the invention also relates to a protein with transposase activity that can bind to one or more of the following sequences: SEQ ID NO: 4, SEQ ID NO:5, SEQ ID NO:6, SEQ ID NO:7, SEQ ID NO:8, SEQ ID NO:9, and SEQ ID NO:10.

BRIEF DESCRIPTION OF THE FIGURES

FIG. 1 illustrates the molecular reconstruction of a salmonid Tc1-like transposase gene. FIG. 1(A) is a schematic map of a salmonid TcE with the conserved domains in the transposase and IR/DR (inverted repeat/direct repeat) flanking sequences. FIG. 1(B) provides an exemplary strategy for constructing an open reading frame for a salmonid transposase (SB1–SB3) and then systematically introducing amino acid replacements into this gene (SB4–SB10). Amino acid residues are shown using single letter code at positions within the transposase polypeptide that were modified by site-specific mutagenesis, which are indicated with arrows. Translational termination codons appear as asterisks, frameshift mutations are shown as #. Residues changed to the consensus are check-marked and typed in italics. In the right margin, the various functional tests that were done at various stages of the reconstruction are indicated.

FIG. 2(A) is a nucleic acid sequence (SEQ ID NO:3) encoding the SB protein. FIG. 2(B) is the amino acid sequence (SEQ ID NO:1) of an SB transposase. The major functional domains are highlighted.

FIG. 3 illustrates the DNA-binding activities of an N-terminal derivative of the SB transposase.

FIG. 4 provides the DNase I footprinting of deoxyribonucleoprotein complexes formed by N123. FIG. 4(A) is a photograph of a DNase I footprinting gel containing a 500-fold dilution of the N123 preparation shown in lane 4 of FIG. 3A using the same transposon inverted repeat DNA probe as in FIG. 3B. Reactions were run in the absence (bottom lane) or presence (middle lane) of N123. Maxam-Gilbert sequencing of purine bases in the same DNA was used as a marker (lane 1). Reactions were run in the presence (lane 2) or absence (lane 3) of N123. FIG. 4(B) provides a sequence comparison (SEQ ID NOS:37–40) of the salmonid transposase-binding sites illustrated in Panel A with the corresponding sequences in the zebrafish Tdr1 elements. FIG. 4(C) is a sequence comparison (SEQ ID NOS:41–42) between the outer and internal transposase-binding sites in the SB transposons.

FIG. 5 illustrates the integration activity of SB in human HeLa cells.

FIG. 7 illustrates the integration of neomycin resistance-marked transposons into the chromosomes of HeLa cells.

FIG. 9 illustrates two preferred methods for using the gene transfer system of this invention. Depending on the integration site of the nucleic acid fragment of this invention the effect can be either a loss-of-function or a gain-of-function mutation. Both types of activity can be exploited, for example, for gene discovery and/or functional genomics.

FIG. 10 illustrates a preferred screening strategy using IRS-PCR (interspersed repetitive sequence polymerase chain reaction). FIG. 10A illustrates a chromosomal region in the zebrafish genome containing the retroposon DANA (D) 5'-GGCGACRCAGTGGCGCAGTRGG (SEQ ID NO:13) and 5'-GAAYRTGCAAACTCCACACAGA (SEQ ID NO:14); Tdr1 transposons (T) 5'-TCCATCAGACCA-CAGGACAT (SEQ ID NO:15) and 5'-TGTCAGGAG-GAATGGGCCAAAATTC (SEQ ID NO:16); and Angel (A) (a highly reiterated miniature inverted-repeat transposable element) 5'-TTTCAGTTTTGGGTGAACTATCC (SEQ ID NO:12) sequences. The arrows above the elements represent specific PCR primers.

The X superimposed on the central DANA element is meant to represent a missing element or a mutated primer binding site in the genome of another zebrafish strain. The various amplified sequence tagged sites (STSs) are identified by lowercase letter, beginning with the longest detectable PCR product. The products marked with an X are not produced in the PCR reaction if genomes with defective "X-DNA" are amplified. Elements separated by more than 3000 base pairs (bp) and elements having the wrong orientation relative to each other are not amplified efficiently. FIG. 10B is a schematic of the two sets of DNA amplification products from both genomes with (lane 1) and without (lane 2) the X'ed DANA element. Note that bands "a" and "d" are missing when the marked DANA sequence is not present.

DETAILED DESCRIPTION OF THE PREFERRED EMBODIMENTS

Figure 3A:
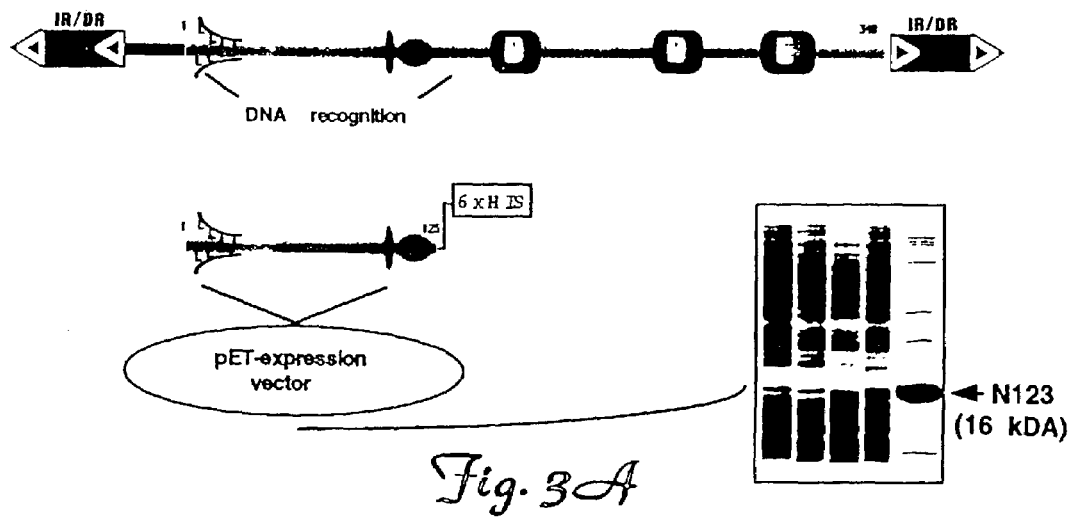
FIG. 3(A) provides the SDS-PAGE analysis illustrating the steps in the expression and purification of N123. Lanes: 1) extract of cells containing expression vector pET21a; 2) extract of cells containing expression vector pET21a/N123 before induction with IPTG; 3) extract of cells containing expression vector pET21a/N123 after 2.5 h of induction with IPTG; 4) partially purified N123 using Ni$^{2+}$-NTA resin. Molecular weights in kDa are indicated on the right.

The present invention relates to novel transposases and the transposons that are used to introduce nucleic acid sequences into the DNA of a cell. A transposase is an enzyme that is capable of binding to DNA at regions of DNA termed inverted repeats. Transposons typically contain at least one, and preferably two, inverted repeats that flank an intervening nucleic acid sequence. The transposase binds to recognition sites in the inverted repeats and catalyzes the incorporation of the transposon into DNA. Inverted repeats of an SB transposon can include two direct repeats and include at least one direct repeat.

Transposons are mobile, in that they can move from one position on DNA to a second position on DNA in the presence of a transposase. There are two fundamental components of any mobile cut-and-paste type transposon system, a source of an active transposase and the DNA sequences that are recognized and mobilized by the transposase. Mobilization of the DNA sequences permits the intervening nucleic acid between the recognized DNA sequences to also be mobilized.

DNA-transposons, including members of the Tc1/mariner superfamily, are ancient residents of vertebrate genomes (Radice et al., 1994; Smit and Riggs, 1996 Proc. Natl. Acad. Sci. USA 93, 1443–1448). However, neither autonomous copies of this class of transposon nor a single case of a spontaneous mutation caused by a TcE insertion have been proven in vertebrate animals. This is in contrast to retroposons whose phylogenetic histories of mutating genes in vertebrates is documented (Izsvak et al., 1997). Failure to isolate active DNA-transposons from vertebrates has greatly hindered ambitions to develop these elements as vectors for germline transformation and insertional mutagenesis. However, the apparent capability of salmonid TcEs for horizontal transmission between two teleost orders (Ivics et al., 1996) suggested that this particular subfamily of fish transposons might be transferred through even larger evolutionary distances.

Reconstructions of ancestral archetypal genes using parsimony analysis have been reported (Jermann et al., 1995. Nature 374, 57–59; Unnikrishnan et al., 1996, Stewart, 1995 Nature 374, 12–13). However, such a strategy requires vertical transmission of a gene through evolution for phylogenetically backtracking to the root sequence. Because parsimony analysis could not resolve the phylogenetic relationships between salmonid TcEs, we took the approach of reconstructing a consensus sequence from inactive elements belonging to the same subfamily of transposons. The resurrection of a functional promoter of the L1 retrotransposon in mouse (Adey et al., 1994 Proc. Natl. Acad. Sci. USA 91, 1569–1573) has previously been reported.

A strategy for obtaining an active gene is not without risks. The consensus sequence of transposase pseudogenes from a single organism may simply reflect the mutations that had occurred during vertical inactivation that have subsequently been fixed in the genome as a result of amplification of the mutated element. For instance, most Tdr1 elements isolated from zebrafish contain a conserved, 350-bp deletion in the transposase gene (Izsvak et al., 1995). Therefore, their consensus is expected to encode an inactive element. In contrast, because independent fixation of the same mutation in different species is unlikely, we derived a consensus from inactive elements of the same subfamily of transposons from several organisms to provide a sequence for an active transposon.

Both the transposase coding regions and the inverted repeats (IRs) of salmonid-type TcEs accumulated several mutations, including point mutations, deletions and insertions, and show about 5% average pairwise divergence (Ivics et al., 1996, supra). Example 1 describes the methods that were used to reconstruct a transposase gene of the salmonid subfamily of fish elements using the accumulated phylogenetic data. This analysis is provided in the EMBL database as DS30090 from FTP.EBI.AC.AK in directory/pub/databases/embl/align and the product of this analysis was a consensus sequence for an inactive SB protein. All the elements that were examined were inactive due to deletions and other mutations. A salmonid transposase gene of the SB transposase family was created using PCR-mutagenesis through the creation of 10 constructs as provided in FIG. 1 and described in Example 1.

This sequence can then be modified further, as described here, to produce active members of the SB protein family.

The SB protein recognizes inverted repeats on a nucleic acid fragment and each inverted repeat includes at least one direct repeat. The gene transfer system of this invention, therefore, comprises two components: a transposase and a cloned, nonautonomous (i.e., non-self inserting) salmonid-type element or transposon (referred to herein as a nucleic acid fragment having at least two inverted repeats) that carries the inverted repeats of the transposon substrate DNA. When put together these two components provide active transposon activity. In use, the transposase binds to the direct repeats in the inverted repeats and promotes integration of the intervening nucleic acid sequence into DNA of a cell a including chromosomes and extra chromosomal DNA of fish as well as mammalian cells. This transposon system does not appear to exist in nature.

The transposase that was reconstructed using the methods of Example 1 represents one member of a family of proteins that can bind to the inverted repeat region of a transposon to effect integration of the intervening nucleic acid sequence into DNA, preferably DNA in a cell. One example of the family of proteins of this invention is provided as SEQ ID NO:1 (see FIG. 2). This family of proteins is referred to herein as SB proteins. The proteins of this invention are provided as a schematic in FIG. 1. The proteins include, from the amino-terminus moving to the carboxy-terminus, a paired-like domain with leucine zipper, one or more nuclear localizing domains (NLS) domains and a catalytic domain including a DD(34)E box and a glycine-rich box as detailed in one example in FIG. 2. The SB family of proteins includes the protein having the amino acid sequence of SEQ ID NO: 1 and also includes proteins with an amino acid sequence that shares at least an 80% amino acid identity to SEQ ID NO:1. That is, when the proteins of the SB family are aligned, at least 80% of the amino acid sequence is identical. Proteins of the SB family are transposases, that is, they are able to catalyze the integration of nucleic acid into DNA of a cell. In addition, the proteins of this invention are able to bind to the inverted repeat sequences of SEQ ID NOS:4–5 and direct repeat sequences (SEQ ID NOS:6–9) from a transposon as well as a consensus direct repeat sequence (SEQ ID NO:10). The SB proteins preferably have a molecular weight range of about 35 kD to about 40 kD on about a 10% SDS-polyacrylamide gel.

To create an active SB protein, suitable for further modification, a number of chromosomal fragments were sequenced and identified by their homology to the zebrafish transposon-like sequence Tdr1, from eleven species of fish (Ivics et al., 1996). Next these and other homologous sequences were compiled and aligned. The sequences were identified in either GenBank or the EMBL database. Others have suggested using parsimony analysis to arrive at a consensus sequence but in this case parsimony analysis could not resolve the phylogenetic relationships among the salmonid-type TcEs that had been compiled. A consensus transposon was then engineered by changing selected nucleotides in codons to restore the amino acids that were likely to be in that position. This strategy assumes that the most common amino acid in a given position is probably the original (active) amino acid for that locus. The consensus sequence was examined for sites at which it appeared that C->T mutations had been fixed where deamination of $^{5m}C$ residues may have occurred (which leads to C being converted to T which in turn can lead to the "repair" of the mismatched G residue to an A). In these instances, the "majority-rule" consensus sequence was not always used. Next various expected activities of the resurrected transposase were tested to ensure the accuracy of the engineering.

The amino acid residues described herein employ either the single letter amino acid designator or the three-letter abbreviation. Abbreviations used herein are in keeping with the standard polypeptide nomenclature, *J. Biol. Chem.*, (1969), 243, 3552–3559. All amino acid residue sequences are represented herein by formulae with left and right orientation in the conventional direction of amino-terminus to carboxy-terminus.

Although particular amino acid sequences encoding the transposases of this invention have been described, there are a variety of conservative changes that can be made to the amino acid sequence of the SB protein without altering SB activity. These changes are termed conservative mutations, that is, an amino acid belonging to a grouping of amino acids having a particular size or characteristic can be substituted for another amino acid, particularly in regions of the protein that are not associated with catalytic activity or DNA binding activity, for example. Other amino acid sequences of the SB protein include amino acid sequences containing conservative changes that do not significantly alter the activity or binding characteristics of the resulting protein. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Particularly preferred conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$.

The SB protein has catalytic activity in a cell but the protein can be introduced into a cell as protein or as nucleic acid. The SB protein can be introduced into the cell as ribonucleic acid, including mRNA; as DNA present in the cell as extrachromosomal DNA including, but not limited to, episomal DNA, as plasmid DNA, or as viral nucleic acid. Further, DNA encoding the SB protein can be stably integrated into the genome of the cell for constitutive or inducible expression. Where the SB protein is introduced into the cell as nucleic acid, the SB encoding sequence is preferably operably linked to a promoter. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product.

One nucleic acid sequence encoding the SB protein is provided as SEQ ID NO:3. In addition to the conservative changes discussed above that would necessarily alter the SB-encoding nucleic acid sequence, there are other DNA or RNA sequences encoding SB protein that have the same amino acid sequence as an SB protein, but which take advantage of the degeneracy of the three letter codons used to specify a particular amino acid. For example, it is well known in the art that the following RNA codons (and therefore, the corresponding DNA codons, with a T substituted for a U) can be used interchangeably to code for each specific amino acid:

| | |
|---|---|
| Phenylalanine (Phe or F) | UUU or UUC |
| Leucine (Leu or L) | UUA, UUG, CUU, CUC, CUA or CUG |
| Isoleucine (Ile or I) | AUU, AUC or AUA |
| Methionine (Met or M) | AUG |
| Valine (Val or V) | GUU, GUC, GUA, GUG |
| Serine (Ser or S) | UCU, UCC, UCA, UCG, AGU, AGC |
| Proline (Pro or P) | CCU, CCC, CCA, CCG |
| Threonine (Thr or T) | ACU, ACC, ACA, ACG |
| Alanine (Ala or A) | GCU, GCG, GCA, GCC |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU, CGC, CGA, CGG, AGA, AGC |
| Glycine (Gly or G) | GGU or GGC or GGA or GGG |
| Termination codon | UAA, UAG or UGA |

Further, a particular DNA sequence can be modified to employ the codons preferred for a particular cell type. For example, the preferred codon usage for *E. coli* is known, as are preferred codon usages for animals and humans. These changes are known to those of ordinary skill in the art and are therefore considered part of this invention.

Also contemplated in this invention are antibodies directed to an SB protein of this invention. An "antibody" for purposes of this invention is any immunoglobulin, including antibodies and fragments thereof that specifically binds to an SB protein. The antibodies can be polyclonal, monoclonal and chimeric antibodies. Various methods are known in the art that can be used for the production of polyclonal or monoclonal antibodies to SB protein. See, for example, *Antibodies: A Laboratory Manual*, Harlow and Lane, eds., Cold Spring Harbor Laboratory Press: Cold Spring Harbor, N.Y., 1988).

The nucleic acid encoding the SB protein can be introduced into a cell as a nucleic acid vector such as a plasmid, or as a gene expression vector, including a viral vector. The nucleic acid can be circular or linear. Methods for manipulating DNA and protein are known in the art and are explained in detail in the literature such as Sambrook et al, (1989) *Molecular Cloning: A Laboratory Manual.*, Cold Spring Harbor Laboratory Press or Ausubel, R. M., ed. (1994). *Current Protocols in Molecular Biology*. A vector, as used herein, refers to a plasmid, a viral vector or a cosmid that can incorporate nucleic acid encoding the SB protein or the nucleic acid fragment of this invention. The term "coding sequence" or "open reading frame" refers to a region of nucleic acid that can be transcribed and/or translated into a polypeptide in vivo when placed under the control of the appropriate regulatory sequences.

Another aspect of this invention relates to a nucleic acid fragment, sometimes referred to as a transposon or transposon element that includes a nucleic acid sequence positioned between at least two inverted repeats. Each inverted repeat preferably includes at least one direct repeat (hence, the name IR/DR). The transposon element is a linear nucleic acid fragment (extending from the 5' end to the 3' end, by convention) that can be used as a linear fragment or circularized, for example in a plasmid. In a preferred embodiment there are two direct repeats in each inverted repeat sequence. Preferred direct repeat sequences that bind to SB include:

(SEQ ID NO:6)
The 5' outer repeat:
5'-GTTGAAGTCGGAAGTTTACATACACTTAAG-3'

(SEQ ID NO:7)
The 5' inner repeat:
5'-CAGTGGGTCAGAAGTTTACATACACTAAGG-3'

(SEQ ID NO:8)
The 3' inner repeat
5'-CAGTGGGTCAGAAGTTAACATACACTCAATT-3'

(SEQ ID NO:9)
The 3' outer repeat
5'-AGTTGAAGTCGGAAGTTTACATACACCTTAG-3'.

(SEQ ID NO:10)
A preferred consensus direct repeat is
5'-CA(GT)TG(AG)GTC(AG)GAAGTTTACATACACTTAAG-3'

In one embodiment the direct repeat sequence includes at least the following sequence:
ACATACAC (SEQ ID NO:11)

A preferred inverted repeat sequence of this invention is SEQ ID NO:4

5'-AGTTGAAGTC GGAAGTTTAC ATACACTTAA GTTGGAGTCA

TTAAAACTCG TTTTTCAACT ACACCACAAA TTTCTTGTTA

ACAAACAATA GTTTTGGCAA GTCAGTTAGG ACATCTACTT

TGTGCATGAC ACAAGTCATT TTTCCAACAA TTGTTTACAG

ACAGATTATT TCACTTATAA TTCACTGTAT CACAATTCCA

GTGGGTCAGA AGTTTACATA CACTAA-3' and a second inverted repeat sequence of this invention is SEQ ID NO:5

5'-TTGAGTGTAT GTTAACTTCT GACCCACTGG GAATGTGATG

AAAGAAATAA AGCTGAAAT GAATCATTCT CTCTACTATT

ATTCTGATAT TTCACATTCT TAAAATAAAG TGGTGATCCT

AACTGACCTT AAGACAGGGA ATCTTTACTC GGATTAAATG

TCAGGAATTG TGAAAAAGTG AGTTTAAATG TATTTGGCTA

AGGTGTATGT AAACTTCCGA CTTCAACTG-3'.

Preferably the direct repeats are the portion of the inverted repeat that bind to the SB protein to permit insertion and integration of the nucleic acid fragment into the cell. The site of DNA integration for the SB proteins occurs at TA base pairs (see FIG. 7B).

The inverted repeats flank a nucleic acid sequence which is inserted into the DNA in a cell. The nucleic acid sequence can include all or part of an open reading from of a gene (i.e., that part of a gene encoding protein), one or more expression control sequences (i.e., regulatory regions in nucleic acid) alone or together with all or part of an open reading frame. Preferred expression control sequences include, but are not limited to promoters, enhancers, border control elements, locus-control regions or silencers. In a preferred embodiment, the nucleic acid sequence comprises a promoter operably linked to at least a portion of an open reading frame.

As illustrated in the examples, the combination of the nucleic acid fragment of this invention comprising a nucleic acid sequence positioned between at least two inverted repeats wherein the inverted repeats can bind to an SB protein and wherein the nucleic acid fragment is capable of integrating into DNA in a cell, in combination with an SB protein (or nucleic acid encoding the SB protein to deliver SB protein to a cell) results in the integration of the nucleic acid sequence into the cell. Alternatively, it is possible for the nucleic acid fragment of this invention to be incorporated into DNA in a cell through non-homologous recombination through a variety of as yet undefined, but reproducible mechanisms. In either event the nucleic acid fragment can be used for gene transfer.

As described in the examples, the SB family of proteins, mediates integration in a variety of cell types and a variety of species. The SB protein facilitates integration of the nucleic acid fragment of this invention with inverted repeats into both pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). It is likely that the gene transfer system of this invention can be used in a variety of cells including animal cells, bacteria, fungi (e.g., yeast) or plants. Animal cells can be vertebrate or invertebrate. Cells such as oocytes, eggs, and one or more cells of an embryo are also considered in this invention. Mature cells from a variety of organs or tissues can receive the nucleic acid fragment of this invention separately, alone, or together with the SB protein or nucleic acid encoding the SB protein. Cells receiving the nucleic acid fragment or the SB protein and capable of receiving the nucleic acid fragment into the DNA of that cell include, but are not limited to, lymphocytes, hepatocytes, neural cells, muscle cells, a variety of blood cells, and a variety of cells of an organism. Example 4 provides methods for determining whether a particular cell is amenable to gene transfer using this invention. The cells can be obtained from vertebrates or invertebrates. Preferred invertebrates include crustaceans or mollusks including, but not limited to shrimp, scallops, lobster, claims, or oysters.

Vertebrate cells also incorporate the nucleic acid fragment of this invention in the presence of the SB protein. Cells from fish, birds and other animals can be used, as can cells from mammals including, but not limited to, rodents, such as rats or mice, ungulates, such as cows or goats, sheep, swine or cells from a human.

The DNA of a cell that acts as a recipient of the nucleic acid fragment of this invention includes any DNA in contact with the nucleic acid fragment of this invention in the presence of an SB protein. For example, the DNA can be part of the cell genome or it can be extrachromosomal, such as an episome, a plasmid, a circular or linear DNA fragment. Targets for integration are double-stranded DNA.

The combination of the nucleic acid fragment of this invention including a nucleic acid sequence positioned between at least two inverted repeats wherein the inverted repeats can bind to an SB protein and wherein the nucleic acid fragment is capable of integrating into DNA of a cell in combination with a transposase or nucleic acid encoding a transposase, wherein the transposase is an SB protein, including SB proteins that include an amino acid sequence that is 80% identical to SEQ ID NO:1 is useful as a gene transfer system to introduce DNA into the DNA of a cell. In a preferred embodiment, the SB protein comprises the amino acid sequence of SEQ ID NO:1 and in another preferred embodiment the DNA encoding the transposase can hybridize to the DNA of SEQ ID NO:3 under the following hybridization conditions: in 30% (v/v) formamide in 0.5×SSC, 0.1% (w/v) SDS at 42° C. for 7 hours.

Gene transfer vectors for gene therapy can be broadly classified as viral vectors or non-viral vectors. The use of the nucleic acid fragment of this invention as a transposon in combination with an SB protein is a refinement of non-viral DNA-mediated gene transfer. Up to the present time, viral vectors have been found to be more efficient at introducing and expressing genes in cells. There are several reasons why non-viral gene transfer is superior to virus-mediated gene transfer for the development of new gene therapies. For example, adapting viruses as agents for gene therapy restricts genetic design to the constraints of that virus genome in terms of size, structure and regulation of expression. Non-viral vectors are generated largely from synthetic starting materials and are therefore more easily manufactured than viral vectors. Non-viral reagents are less likely to be immunogenic than viral agents making repeat administration possible. Non-viral vectors are more stable than viral vectors and therefore better suited for pharmaceutical formulation and application than are viral vectors.

Current non-viral gene transfer systems are not equipped to promote integration of nucleic acid into the DNA of a cell, including host chromosomes. As a result, stable gene transfer frequencies using non-viral systems have been very low; 0.1% at best in tissue culture cells and much less in primary cells and tissues. The present system is a non-viral gene transfer system that facilitates integration and markedly improves the frequency of stable gene transfer.

In the gene transfer system of this invention the SB protein can be introduced into the cell as a protein or as nucleic acid encoding the protein. In one embodiment the nucleic acid encoding the protein is RNA and in another, the nucleic acid is DNA. Further, nucleic acid encoding the SB protein can be incorporated into a cell through a viral vector, cationic lipid, or other standard transfection mechanisms including electroporation or particle bombardment used for eukaryotic cells. Following introduction of nucleic acid encoding SB, the nucleic acid fragment of this invention can be introduced into the same cell.

Similarly, the nucleic acid fragment can be introduced into the cell as a linear fragment or as a circularized fragment, preferably as a plasmid or as recombinant viral DNA. Preferably the nucleic acid sequence comprises at least a portion of an open reading frame to produce an amino-acid containing product. In a preferred embodiment the nucleic acid sequence encodes at least one protein and includes at least one promoter selected to direct expression of the open reading frame or coding region of the nucleic acid sequence. The protein encoded by the nucleic acid sequence can be any of a variety of recombinant proteins new or known in the art. In one embodiment the protein encoded by the nucleic acid sequence is a marker protein such as green fluorescent protein (GFP), chloramphenicol acetyltransferase (CAT), growth hormones, for example to promote growth in a transgenic animal, β-galactosidase (lacZ), luciferase (LUC), and insulin-like growth factors (IGFs).

In one embodiment of a transgenic animal, the protein is a product for isolation from a cell. Transgenic animals as bioreactors are known. Protein can be produced in quantity in milk, urine, blood or eggs. Promoters are known that promote expression in milk, urine, blood or eggs and these include, but are not limited to, casein promoter, the mouse urinary protein promoter, β-globin promoter and the ovalbumin promoter respectively. Recombinant growth hormone, recombinant insulin, and a variety of other recombinant proteins have been produced using other methods for producing protein in a cell. Nucleic acid encoding these or other proteins can be incorporated into the nucleic acid fragment of this invention and introduced into a cell. Efficient incorporation of the nucleic acid fragment into the DNA of a cell occurs when an SB protein is present. Where the cell is part of a tissue or part of a transgenic animal, large amounts of recombinant protein can be obtained. There are a variety of methods for producing transgenic animals for research or for protein production including, but not limited to (Hackett et al. (1993). The molecular biology of transgenic fish. In *Biochemistry and Molecular Biology of Fishes* (Hochachka & Mommsen, eds) Vol. 2, pp. 207–240. Other methods for producing transgenic animals include the teachings of M. Markkula et al., *Rev. Reprod.*, 1, 97–106 (1996); R. T. Wall et al., *J. Dairy Sci.*, 80, 2213–2224 (1997); J. C. Dalton, et al., *Adv. Exp. Med. Biol.*, 411, 419–428 (1997); and H. Lubon et al., *Transfus. Med Rev.*, 10, 131–143 (1996). Transgenic zebrafish were made, as described in Example 6. The system has also been tested through the introduction of the nucleic acid with a marker protein into mouse embryonic stem cells (ES) and it is known that these cells can be used to produce transgenic mice (A. Bradley et al., *Nature*, 309, 255–256 (1984).

In general, there are two methods to achieve improved stocks of commercially important animals. The first is classical breeding, which has worked well for land animals, but it takes decades to make major changes. A review by Hackett et al. (1997) points out that by controlled breeding, growth rates in coho salmon (*Oncorhynchus kisutch*) increased 60% over four generations and body weights of two strains of channel catfish (*Ictalurus punctatus*) were increased 21 to 29% over three generations. The second method is genetic engineering, a selective process by which genes are introduced into the chromosomes of animals or plants to give these organisms a new trait or characteristic, like improved growth or greater resistance to disease. The results of genetic engineering have exceeded those of breeding in some cases. In a single generation, increases in body weight of 58% in common carp (*Cyprinus carpio*) with extra rainbow trout growth hormone I genes, more than 1000% in salmon with extra salmon growth hormone genes, and less in trout were obtained. The advantage of genetic engineering in fish, for example, is that an organism can be altered directly in a very short periods of time if the appropriate gene has been identified (see Hackett, 1997). The disadvantage of genetic engineering in fish is that few of the many genes that are involved in growth and development have been identified and the interactions of their protein products is poorly understood. Procedures for genetic manipulation are lacking many economically important animals. The present invention provides an efficient system for performing insertional mutagenesis (gene tagging) and efficient procedures for producing transgenic animals. Prior to this invention, transgenic DNA is not efficiently incorporated into chromosomes. Only about one in a million of the foreign DNA molecules integrates into the cellular genome, generally several cleavage cycles into development. Consequently, most transgenic animals are mosaic (Hackett, 1993). As a result, animals raised from embryos into which transgenic DNA has been delivered must be cultured until gametes can be assayed for the presence of integrated foreign DNA. Many transgenic animals fail to express the transgene due to position effects. A simple, reliable procedure that directs early integration of exogenous DNA into the chromosomes of animals at the one-cell stage is needed. The present system helps to fill this need.

The transposon system of this invention has applications to many areas of biotechnology. Development of transposable elements for vectors in animals permits the following: 1) efficient insertion of genetic material into animal chromosomes using the methods given in this application. 2) identification, isolation, and characterization of genes involved with growth and development through the use of transposons as insertional mutagens (e.g., see Kaiser et al., 1995, "Eukaryotic transposable elements as tools to study gene structure and function." In *Mobile Genetic Elements*, IRL Press, pp. 69–100). 3) identification, isolation and characterization of transcriptional regulatory sequences controlling growth and development. 4) use of marker constructs for quantitative trait loci (QTL) analysis. 5) identification of genetic loci of economically important traits, besides those for growth and development, i.e., disease resistance (e.g., Anderson et al., 1996, *Mol. Mar. Biol. Biotech.*, 5, 105–113). In one example, the system of this invention can be used to produce sterile transgenic fish. Broodstock with inactivated genes could be mated to produce sterile offspring for either biological containment or for maximizing growth rates in aquacultured fish.

In yet another use of the gene transfer system of this invention, the nucleic acid fragment is modified to incorporate a gene to provide a gene therapy to a cell. The gene is placed under the control of a tissue specific promoter or of a ubiquitous promoter or one or more other expression control regions for the expression of a gene in a cell in need of that gene. A variety of genes are being tested for a variety of gene therapies including, but not limited to, the CFTR gene for cystic fibrosis, adenosine deaminase (ADA) for immune system disorders, factor IX and interleukin-2 (IL-2) for blood cell diseases, alpha-1-antitrypsin for lung disease, and tumor necrosis factors (TNFs) and multiple drug resistance (MDR) proteins for cancer therapies.

These and a variety of human or animal specific gene sequences including gene sequences to encode marker proteins and a variety of recombinant proteins are available in the known gene databases such as GenBank, and the like.

Further, the gene transfer system of this invention can be used as part of a process for working with or for screening a library of recombinant sequences, for example, to assess the function of the sequences or to screen for protein expression, or to assess the effect of a particular protein or a particular expression control region on a particular cell type. In this example, a library of recombinant sequences, such as the product of a combinatorial library or the product of gene shuffling, both techniques now known in the art and not the focus of this invention, can be incorporated into the nucleic acid fragment of this invention to produce a library of nucleic acid fragments with varying nucleic acid sequences positioned between constant inverted repeat sequences. The library is then introduced into cells together with the SB protein as discussed above.

An advantage of this system is that it is not limited to a great extent by the size of the intervening nucleic acid sequence positioned between the inverted repeats. The SB protein has been used to incorporate transposons ranging from 1.3 kilobases (kb) to about 5.0 kb and the mariner transposase has mobilized transposons up to about 13 kb. There is no known limit on the size of the nucleic acid sequence that can be incorporated into DNA of a cell using the SB protein.

Rather, what is limiting can be the method by which the gene transfer system of this invention is introduced into cells. For example, where microinjection is used, there is very little restraint on the size of the intervening sequence of the nucleic acid fragment of this invention. Similarly, lipid-mediated strategies do not have substantial size limitations. However, other strategies for introducing the gene transfer system into a cell, such as viral-mediated strategies could limit the length of the nucleic acid sequence positioned between the inverted repeats, according to this invention.

The two part SB transposon system can be delivered to cells via viruses, including retroviruses (including lentiviruses), adenoviruses, adeno-associated viruses, herpesviruses, and others. There are several potential combinations of delivery mechanisms for the transposon portion containing the transgene of interest flanked by the inverted terminal repeats (IRs) and the gene encoding the transposase. For example, both the transposon and the transposase gene can be contained together on the same recombinant viral genome; a single infection delivers both parts of the SB system such that expression of the transposase then directs cleavage of the transposon from the recombinant viral genome for subsequent integration into a cellular chromosome. In another example, the transposase and the transposon can be delivered separately by a combination of viruses and/or non-viral systems such as lipid-containing reagents. In these cases either the transposon and/or the transposase gene can be delivered by a recombinant virus. In every case, the expressed transposase gene directs liberation of the transposon from its carrier DNA (viral genome) for integration into chromosomal DNA.

This invention also relates to methods for using the gene transfer system of this invention. In one method, the invention relates to the introduction of a nucleic acid fragment comprising a nucleic acid sequence positioned between at least two inverted repeats into a cell. In a preferred embodiment, efficient incorporation of the nucleic acid fragment into the DNA of a cell occurs when the cell also contains an SB protein. As discussed above, the SB protein can be provided to the cell as SB protein or as nucleic acid encoding the SB protein. Nucleic acid encoding the SB protein can take the form of RNA or DNA. The protein can be introduced into the cell alone or in a vector, such as a plasmid or a viral vector. Further, the nucleic acid encoding the SB protein can be stably or transiently incorporated into the genome of the cell to facilitate temporary or prolonged expression of the SB protein in the cell. Further, promoters or other expression control regions can be operably linked with the nucleic acid encoding the SB protein to regulate expression of the protein in a quantitative or in a tissue-specific manner. As discussed above, the SB protein is a member of a family of SB proteins preferably having at least an 80% amino acid sequence identity to SEQ ID NO:1 and more preferably at least a 90% amino acid sequence identity to SEQ ID NO:1. Further, the SB protein contains a DNA-binding domain, a catalytic domain (having transposase activity) and an NLS signal.

The nucleic acid fragment of this invention is introduced into one or more cells using any of a variety of techniques known in the art such as, but not limited to, microinjection, combining the nucleic acid fragment with lipid vesicles, such as cationic lipid vesicles, particle bombardment, electroporation, DNA condensing reagents (e.g., calcium phosphate, polylysine or polyethyleneimine) or incorporating the nucleic acid fragment into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

The gene transfer system of this invention can readily be used to produce transgenic animals that carry a particular marker or express a particular protein in one or more cells of the animal. Methods for producing transgenic animals are known in the art and the incorporation of the gene transfer system of this invention into these techniques does not require undue experimentation. The examples provided below teach methods for creating transgenic fish by micro-injecting the gene transfer system into a cell of an embryo of the fish. Further, the examples also describe a method for introducing the gene transfer system into mouse embryonic stem cells. Methods for producing transgenic mice from embryonic stem cells are well known in the art. Further a review of the production of biopharmaceutical proteins in the milk of transgenic dairy animals (see Young et al., *BIO PHARM* (1997), 10, 34–38) and the references provided therein detail methods and strategies for producing recombinant proteins in milk. The methods and the gene transfer system of this invention can be readily incorporated into these transgenic techniques without undue experimentation in view of what is known in the art and particularly in view of this disclosure.

The nucleic acid fragments of this invention in combination with the SB protein or nucleic acid encoding the SB protein is a powerful tool for germline transformation, for the production of transgenic animals, as methods for introducing nucleic acid into DNA in a cell, for insertional mutagenesis, and for gene tagging in a variety of species. Two strategies are diagrammed in FIG. 9.

Due to their inherent ability to move from one chromosomal location to another within and between genomes, transposable elements have been exploited as genetic vectors for genetic manipulations in several organisms. Transposon tagging is a technique in which transposons are mobilized to "hop" into genes, thereby inactivating them by insertional mutagenesis. These methods are discussed by Evans et al., *TIG* 1997 13, 370–374. In the process, the inactivated genes are "tagged" by the transposable element which then can be used to recover the mutated allele. The ability of the human and other genome projects to acquire gene sequence data has outpaced the ability of scientists to ascribe biological function to the new genes. Therefore, the present invention provides an efficient method for introducing a tag into the genome of a cell. Where the tag is inserted into a location in the cell that disrupts expression of a protein that is associated with a particular phenotype, expression of an altered phenotype in a cell containing the nucleic acid of this invention permits the association of a particular phenotype with a particular gene that has been disrupted by the nucleic acid fragment of this invention. Here the nucleic acid fragment functions as a tag. Primers designed to sequence the genomic DNA flanking the nucleic acid fragment of this invention can be used to obtain sequence information about the disrupted gene.

The nucleic acid fragment can also be used for gene discovery. In one example, the nucleic acid fragment in combination with the SB protein or nucleic acid encoding the SB protein is introduced into a cell. The nucleic acid fragment preferably comprises a nucleic acid sequence positioned between at least two inverted repeats, wherein the inverted repeats bind to the SB protein and wherein the nucleic acid fragment integrates into the DNA of the cell in the presence of the SB protein. In a preferred embodiment, the nucleic acid sequence includes a marker protein, such as GFP and a restriction endonuclease recognition site, preferably a 6-base recognition sequence. Following integration, the cell DNA is isolated and digested with the restriction endonculease. Where a restriction endonuclease is used that employs a 6-base recognition sequence, the cell DNA is cut into about 4000-bp fragments on average. These fragments can be either cloned or linkers can be added to the ends of the digested fragments to provide complementary sequence for PCR primers. Where linkers are added, PCR reactions are used to amplify fragments using primers from the linkers and primers binding to the direct repeats of the inverted repeats in the nucleic acid fragment. The amplified fragments are then sequenced and the DNA flanking the direct repeats is used to search computer databases such as GenBank.

In another application of this invention, the invention provides a method for mobilizing a nucleic acid sequence in a cell. In this method the nucleic acid fragment of this invention is incorporated into DNA in a cell, as provided in the discussion above. Additional SB protein or nucleic acid encoding the SB protein is introduced into the cell and the protein is able to mobilize (i.e. move) the nucleic acid fragment from a first position within the DNA of the cell to a second position within the DNA of the cell. The DNA of the cell can be genomic DNA or extrachromosomal DNA. The method permits the movement of the nucleic acid fragment from one location in the genome to another location in the genome, or for example, from a plasmid in a cell to the genome of that cell.

All references, patents and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully practice the intended invention.

EXAMPLE 1

Reconstruction of an SB Transposase

Recombinant DNA

Gene reconstruction-Phase 1: Reconstruction of a transposase open reading frame. The Tss1.1 element from Atlantic salmon (GenBank accession number L12206) was PCR-amplified using a primer pair flanking the defective transposase gene, FTC-Start and FTC-Stop to yield product SB1. Next, a segment of the defective transposase gene of the Tss1.2 element (L12207) was PCR-amplified using PCR primers FTC-3 and FTC-4, then further amplified with FTC-3 and FTC-5. The PCR product was digested with restriction enzymes NcoI and BlpI, underlined in the primer sequences, and cloned to replace the corresponding fragment in SB1 to yield SB2. Then, an approximately 250 bp HindIII fragment of the defective transposase gene of the Tsg1 element from rainbow trout (L12209) was isolated and cloned into the respective sites in SB2 to result in SB3. The Tss1 and Tsg1 elements were described in (Radice et al., 1994) and were kind gifts from S. W. Emmons.

```
FTC-Start:
5'-CCTCTAGGATCCGACATCATG            (SEQ ID NO:17)

FTC-Stop:
5'-TCTAGAATTCTAGTATTTGGTAGCATTG     (SEQ ID NO:18)

FTC-3:
5'-AACACCATGGGACCACGCAGCCGTCA       (SEQ ID NO:19)
```

-continued
```
FTC-4:
5'-CAGGTTATGTCGATATAGGACTCGTTTTAC   (SEQ ID NO:20)

FTC-5:
5'-CCTTGCTGAGCGGCCTTTCAGGTTATGTCG   (SEQ ID NO:21)
```

Gene reconstruction-Phase 2: Site-specific PCR mutagenesis of the SB3 open reading frame to introduce consensus amino acids. For PCR mutagenesis, two methods have been used: megaprimer PCR (Sarkar and Sommer, 1990 *BioTechniques* 8, 404–407) from SB4 through SB6, and Ligase Chain Reaction (Michael, 1994 *BioTechniques* 16, 410–412) for steps SB7 to SB10.

Oligonucleotide primers for product SB4 were the following:

```
FTC-7:                              (SEQ ID NO:22)
5'-TTGCACTTTTCGCACCAA
for Gln→Arg(74) and Asn→Lys(75);

FTC-13:                             (SEQ ID NO:23)
5'-GTACCTGTTTCCTCCAGCATC
for Ala→Glu(93);

FTC-8:                              (SEQ ID NO:24)
5'-GAGCAGTGGCTTCTTCCT
for Leu→Pro(121);

FTC-9:                              (SEQ ID NO:25)
5'-CCACAACATGATGCTGCC
for Leu→Met(193);

FTC-10:                             (SEQ ID NO:26)
5'-TGGCCACTCCAATACCTTGAC
for Ala→Val(265) and Cys→Trp(268);

FTC-11:                             (SEQ ID NO:27)
5'-ACACTCTAGACTAGTATTTGGTAGCATTGCC
for Ser→Ala(337) and Asn→Lys(339).
```

Oligonucleotide primers for product SB5:

```
B5-PTV:                             (SEQ ID NO:28)
5'-GTGCTTCACGGTTGGGATGGTG
for Leu→Pro(183), Asn→Thr(184) and Met→Val(185).
```

Oligonucleotide primers for product SB6:

```
FTC-DDE:                            (SEQ ID NO:29)
5'-ATTTTCTATAGGATTGAGGTCAGGGC
for Asp→Glu(279).
```

Oligonucleotide primers for products SB7 and SB8, in two steps:

```
PR-GAIS:                            (SEQ ID NO:30)
5'-GTCTGGTTCATCCTTGGGAGCAATTTCCAAACGCC
for Asn→Ile(28), His→Arg(31) and Phe→Ser(21).
```

Oligonucleotide primers for product SB9:

```
KARL:                               (SEQ ID NO:31)
5'-CAAAACCGACATAAGAAAGCCAGACTACGG
for Pro→Arg(126);

RA:                                 (SEQ ID NO:32)
5'-ACCATCGTTATGTTTGGAGGAAGAAGGGGGAGGCTTGCAAGCCG
for Cys→Arg(166) and Thr→Ala(175);

EY:                                 (SEQ ID NO:33)
5'-GGCATCATGAGGAAGGAAAATTATGTGGATATATTG
for Lys→Glu(216) and Asp→Tyr(218);
```

-continued

KRV: (SEQ ID NO:34)
5'-CTGAAAAAGCGTGTGCGAGCAAGGAGGCC
for Cys→Arg(288);

VEGYP: (SEQ ID NO:35)
5'-GTGGAAGGCTACCCGAAACGTTTGACC
for Leu→Pro(324).

Oligonucleotide primers for product SB10:

FATAH: (SEQ ID NO:36)
5'-GACAAAGATCGTACTTFTTGGAGAAATGTC
for Cys→Arg(143).

Plasmids. For pSB10, the SB10 transposase gene was cut with EcoRI and BamHI, whose recognition sequences are incorporated and underlined above in the primers FTC-Start and FTC-Stop, filled in with Klenow and cloned into the Klenow-filled NotI sites of CMV-βgal (Clonetech), replacing the LacZ gene originally present in this plasmid. Because of the blunt-end cloning, both orientations of the gene insert were possible to obtain and the antisense direction was used as a control for transposase. For pSB10-ΔDDE, plasmid pSB10 was cut with MscI, which removes 322 bp of the transposase coding region, and recircularized. Removal of the MscI fragment from the transposase gene deleted much of the catalytic DDE domain and disrupted the reading frame by introducing a premature translational termination codon.

Sequence alignment of 12 partial salmonid-type TcE sequences found in 8 fish species (available under DS30090 from FTP.EBI.AC.AK in directory/pub/databases/embl/align from the EMBL database) allowed us to derive a majority-rule, salmonid-type consensus sequence, and identify conserved protein and DNA sequence motifs that likely have functional importance (FIG. 1A).

Conceptual translation of the mutated transposase open reading frames and comparison with functional motifs in other proteins allowed us to identify five regions that are highly conserved in the SB transposase family (FIG. 1A): I) a paired box/leucine zipper motif at the N-terminus; ii) a DNA-binding domain; iii) a bipartite nuclear localization signal (NLS); iv) a glycine-rich motif close to the center of the transposase without any known function at present; and v) a catalytic domain consisting of three segments in the C-terminal half comprising the DDE domain that catalyzes the transposition. DDE domains were identified by Doak et al. in Tc1 mariner sequences (Doak et al., 1994 Proc. Natl. Acad. Sci. USA 91, 942–946). Multiple sequence alignment also revealed a fairly random distribution of mutations in transposase coding sequences; 72% had occurred at non-synonymous positions in codons. The highest mutation frequencies were observed at CpG dinucleotide sites which are highly mutable (Adey et al., 1994, supra). Although amino acid substitutions were distributed throughout the transposases, fewer mutations were detected at the conserved motifs (0.07 non-synonymous mutations per codon), as compared to protein regions between the conserved domains (0.1 non-synonymous mutations per codon). This observation indicated to us that some selection mechanism had maintained the functional domains before inactivation of transposons took place in host genomes. The identification of these putative functional domains was of key importance during the reactivation procedure.

The first step of reactivating the transposase gene, was to restore an open reading frame (SB1 through SB3 in FIG. 1B) from bits and pieces of two inactive TcEs from Atlantic salmon (Salmo salar) and a single element from rainbow trout (Oncorhynchus mykiss) (Radice et al., 1994, supra). SB3, which has a complete open reading frame after removal of stop codons and frameshifts, was tested in an excision assay similar to that described by Handler et al. (1993) but no detectable activity was observed. Due to non-synonymous nucleotide substitutions, the SB3 polypeptide differs from the consensus transposase sequence in 24 positions (FIG. 1B) which can be sorted into two groups; nine residues that are probably essential for transposase activity because they are in the presumed functional domains and/or conserved in the entire Tc1 family, and another fifteen residues whose relative importance could not be predicted. Consequently, we undertook a dual gene reconstruction strategy. First, the putative functional protein domains of the transposase were systematically rebuilt one at a time by correcting the former group of mutations. Each domain for a biochemical activity was tested independently when possible. Second, in parallel with the first approach, a full-length, putative transposase gene was synthesized by extending the reconstruction procedure to all of the 24 mutant amino acids in the putative transposase.

Accordingly, a series of constructs was made to bring the coding sequence closer, step-by-step, to the consensus using PCR mutagenesis (SB4 through SB10 in FIG. 1B). As a general approach the sequence information predicted by the majority-rule consensus was followed. However, at some codons deamination of $^{5m}C$ residues of CpG sites occurred, and C->T mutations had been fixed in many elements. At R(288), where TpG's and CpG's were represented in equal numbers in the alignment, the CpG sequence was chosen because the CpG->TpG transition is more common in vertebrates than the TpG->CpG. The result of this extensive genetic engineering is a synthetic transposase gene encoding 340 amino acids (SB10 in FIGS. 1B and 2).

The reconstituted functional transposase domains were tested for activity. First, a short segment of the SB4 transposase gene (FIG. 1B) encoding an NLS-like protein motif was fused to the lacZ gene. The transposase NLS was able to mediate the transfer of the cytoplasmic marker-protein, β-galactosidase, into the nuclei of cultured mouse cells (Ivics et al., 1996, supra), supporting our predictions that a bipartite NLS was a functional motif in SB and that our approach to resurrect a full-length, multifunctional enzyme was viable.

EXAMPLE 2

Preparation of a Nucleic Acid Fragment with Inverted Repeat Sequences

In contrast to the prototypic Tc1 transposon from Caenorhabditis elegans which has short, 54-bp indirect repeat sequences (IRs) flanking its transposase gene, most TcEs in fish belong to the IR/DR subgroup of TcEs (Ivics et al., 1996; Izsvak et al., 1995, both supra) which have long, 210–250 bp IRs at their termini and directly repeated DNA sequence motifs (DRs) at the ends of each IR (FIG. 1A). However, the consensus IR sequences are not perfect repeats (i.e., similar, but not identical) indicating that, in contrast to most TcEs, these fish elements naturally possess imperfect inverted repeats. The match is less than 80% at the center of the IRs, but is perfect at the DRs, suggesting that this nonrandom distribution of dissimilarity could be the result of positive selection that has maintained functionally important sequence motifs in the IRs (FIG. 3). Therefore, we suspected that DNA sequences at and around the DRs might carry cis-acting information for transposition and mutations within the IRs, but outside the DRs, would probably not impair the ability of the element to transpose. As a model substrate, we chose a single salmonid-type TcE substrate sequence from *Tanichthys albonubes* (hereafter referred to as T) which has intact DR motifs whose sequences are only 3.8% divergent from the salmonid consensus. The variation in the DNase-protected regions of the four DR sequences varied from about 83% to about 95%, see SEQ ID NOS:6–9.

A TcE from *Tanichthys albonubes* (L48685) was cloned into the SmaI site of pUC19 to result in pT. The donor construct for the integration assays, pT/neo, was made by cloning, after Klenow fill-in, an EcoRI/BamHI fragment of the plasmid pRc-CMV (Invitrogen, San Diego, Calif.) containing the SV40 promoter/enhancer, the neomycin resistance gene and an SV40 poly(A) signal into the StuI/MscI sites of pT. The StuI/MscI double digest of T leaves 352 bp on the left side and 372 bp on the right side of the transposon and thus contains the terminal inverted repeats. An EcoRI digest of pT/neo removed a 350 bp fragment including the left inverted repeat of the transposon, and this plasmid, designated pT/neo-ΔIR, was used as a control for the substrate-dependence of transposase-mediated transgene integration (see Example 4)

EXAMPLE 3

DNA Specificity of an SB Transposase

There are at least two distinct subfamilies of TcEs in the genomes of Atlantic salmon and zebrafish, Tss1/Tdr1 and Tss2/Tdr2, respectively. Elements from the same subfamily are more alike, having about 70% nucleic acid identity, even when they are from two different species (e.g., Tss1 and Tdr1) than members of two different subfamilies in the same species. For example, Tdr1 and Tdr2 are characteristically different in their encoded transposases and their inverted repeat sequences, and share only about 30% nucleic acid identity. It may be that certain subfamilies of transposons must be significantly different from each other in order to avoid cross-mobilization. A major question is whether substrate recognition of transposases is sufficiently specific to prevent activation of transposons of closely related subfamilies.

We have shown that the 12-bp DRs of salmonid-type elements, identical to the DRs of zebrafish-type TcEs, are part of the binding sites for SB. However, these binding-sites are 30 bp long. Thus, specific DNA-binding also involves DNA sequences around the DRs that are variable between TcE subfamilies in fish. Such a difference in the sequences of transposase binding sites might explain the inability of N123 to bind efficiently to zebrafish Tdr1 IRs, and may enable the transposase to distinguish even between closely related TcE subfamilies. Indeed, mutations of four base pairs in the 20-bp Tc1 binding site can abolish binding of transposase (Vos and Plasterk, 1994 *EMBO J.* 13, 6125–6132). The DR core motifs are likely involved primarily in transposase-binding while sequences around the DR motifs likely provide the specificity for this binding.

SB has four binding-sites in its transposon substrate DNA that are located at the ends of the IRs. These sites share about a 83% to about a 95% identity (by comparison of SEQ ID NOS:6–9). However, a zebrafish Tdr1 element lacking an internal transposase-binding site was apparently able to transpose. This observation agrees with the finding that removal of internal transposase-binding sites from engineered Tc3 elements did not lessen their ability to transpose (Colloms et al., 1994 *Nucl. Acids Res.* 22, 5548–5554), suggesting that the presence of internal transposase-binding sites is not essential for transposition. Multiple binding-sites for proteins, including transposases, are frequently associated with regulatory functions (Gierl et al., 1988 *EMBO J.* 7, 4045–4053). Consequently, the internal binding-sites for transposases in the IR/DR group of TcEs serve one or more regulatory purposes affecting transposition and/or gene expression.

Once in the nucleus, a transposase must bind specifically to its recognition sequences in the transposon. The specific DNA-binding domains of both the Tc1 and Tc3 transposases have been mapped to their N-terminal regions (Colloms et al., 1994, supra; Vos and Plasterk, 1994, supra). However, there is very little sequence conservation between the N-terminal regions of TcE transposases, suggesting that these sequences are likely to encode specific DNA-binding functions in these proteins. On the other band, the N-terminal region of SB has significant structural and sequence similarities to the paired DNA-binding domain, found in the Pax family of transcription factors, in a novel combination with a leucine zipper-like motif (Ivics et al., 1996, supra). A gene segment encoding the first 123 amino acids of SB (N 123), which presumably contains all the necessary information for specific DNA-binding and includes the NLS, was reconstructed (SB8 in FIG. 1B), and expressed in *E. coli*. N123 was purified via a C-terminal histidine tag as a 16 KDa polypeptide (FIG. 3A).

Induction of N123 was in *E coli* strain BL21(DE3) (Novagen) by the addition of 0.4 mM IPTG at 0.5 O.D. at 600 nm and continued for 2.5 h at 30° C. Cells were sonicated in 25 mM HEPES, pH 7.5, 1 M NaCl, 15% glycerol, 0.25% Tween 20, 2 mM β-mercaptoethanol, 1 mM PMSF) and 10 mM imidazole (pH 8.0) was added to the soluble fraction before it was mixed with $Ni^{2+}$-NTA resin (Qiagen) according to the recommendations of the manufacturer. The resin was washed with 25 mM HEPES (pH 7.5), 1 M NaCl, 30% glycerol, 0.25% Tween 20, 2 mM β-mercaptoethanol, 1 mM PMSF and 50 mM imidazole (pH 8.0) and bound proteins were eluted with sonication buffer containing 300 mM imidazole, and dialyzed overnight at 4° C. against sonication buffer without imidazole.

Figure 3B:
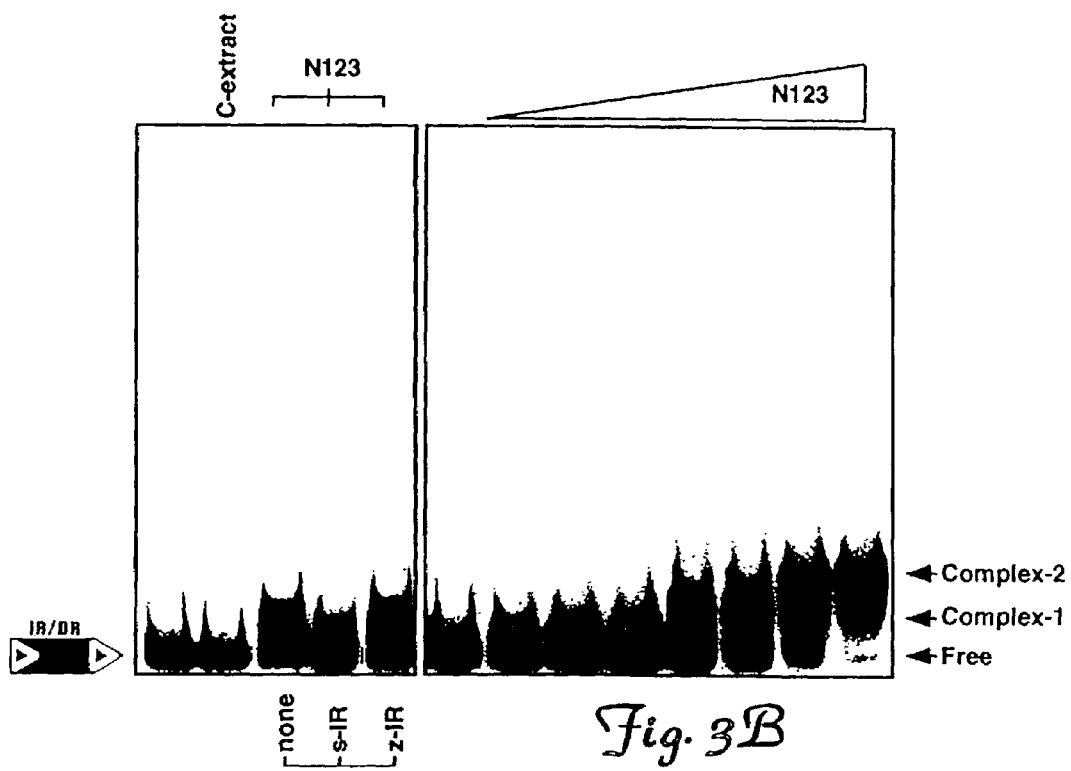
FIG. 3(B) illustrates the results of mobility-shift analysis studies to determine whether N123 bound to the inverted repeats of fish transposons. Lanes: 1) probe only; 2) extract of cells containing expression vector pET21a; 3) 10,000-fold dilution of the N123 preparation shown in lane 4 of Panel A; 4) same as lane 3 plus a 1000-fold molar excess of unlabelled probe as competitor DNA; 5) same as lane 3 plus a 1000-fold molar excess of an inverted repeat fragment of a zebrafish Tdr1 element as competitor DNA; 6–13) 200,000-, 100,000-, 50,000-, 20,000-, 10,000-, 5,000-, 2,500-, and 1,000-fold dilutions of the N123 preparation shown in lane 4 of Panel A.

In addition to the NLS function, N123 also contains the specific DNA-binding domain of SB, as tested in a mobility-shift assay (FIG. 3B). A 300 bp EcoRI/HindIII fragment of pT comprising the left inverted repeat of the element was end-labeled using $[\alpha^{32}P]dCTP$ and Klenow. Nucleoprotein complexes were formed in 20 mM HEPES (pH 7.5), 0.1 mM EDTA, 0.1 mg/ml BSA, 150 mM NaCl, 1 mM DTT in a total volume of 10 µl. Reactions contained 100 pg labeled probe, 2 µg poly[dI][dC] and 1.5 µl N123. After 15 min incubation on ice, 5 µl of loading dye containing 50% glycerol and bromophenol blue was added and the samples loaded onto a 5% polyacrylamide gel (Ausubel). DNaseI footprinting was done using a kit from BRL according to the recommendations of the manufacturer. Upon incubation of a radiolabeled 300-bp DNA fragment comprising the left IR of T, deoxyribonucleoprotein complexes were observed (FIG. 3B, left panel-lane 3), as compared to samples containing extracts of bacteria transformed with the expression vector only (lane 2) or probe without any protein (lane 1). Unlabelled IR sequences of T, added in excess to the reaction as competitor DNA, inhibited binding of the probe (lane 4), whereas the analogous region of a cloned Tdr1 element from zebrafish did not appreciably compete with binding (lane 5). Thus, N123 is able to distinguish between salmonid-type and zebrafish-type TcE substrates.

The number of the deoxyribonucleoprotein complexes detected by the mobility-shift assay at increasingly higher N123 concentrations indicated two protein molecules bound per IR (FIG. 3B, right panel), consistent with either two binding sites for transposase within the IR or a transposase dimer bound to a single site. Transposase-binding sites were further analyzed and mapped in a DNaseI footprinting experiment. Using the same fragment of T as above, two protected regions close to the ends of the IR probe were observed (FIG. 4). The two 30-bp footprints cover the subterminal DR motifs within the IRs. Thus, the DRs are the core sequences for DNA-binding by N123. The DR motifs are almost identical between salmonid- and zebrafish-type TcEs (Ivics et al., 1997). However, the 30-bp transposase binding-sites are longer than the DR motifs and contain 8 base pairs and 7 base pairs in the outer and internal binding sites, respectively, that are different between the zebrafish- and the salmonid-type IRs (FIG. 4B).

Although there are two binding-sites for transposase near the ends of each IR, apparently only the outer sites are utilized for DNA cleavage and thus excision of the transposon. Sequence comparison shows that there is a 3-bp difference in composition and a 2-bp difference in length between the outer and internal transposase-binding sites (FIG. 4C). In summary, our synthetic transposase protein has DNA-binding activity and this binding appears to be specific for salmonid-type IR/DR sequences.

For the expression of an N-terminal derivative of SB transposase, a gene segment of SB8 was PCR-amplified using primers FTC-Start and FTC-8,5'-phosphorylated with T4 polynucleotide kinase, digested with BamHI, filled in with Klenow, and cloned into the NdeI/EcoRI digested expression vector pET21a (Novagen) after Klenow fill-in. This plasmid, pET21a/N123 expresses the first 123 amino acids of the transposase (N123) with a C-terminal histidine tag.

EXAMPLE 4

Transposition of DNA by an SB Transposase

The following experiments demonstrate that the synthetic, salmonid-type SB transposase performed all of the complex steps of transposition, i.e., recognized a DNA molecule, excised the substrate DNA and inserted it into the DNA of a cell, such as a cell chromosome. This is in contrast to control samples that did not include the SB transposase and therefore measured integration through non-homologous recombination.

Figure 7A:
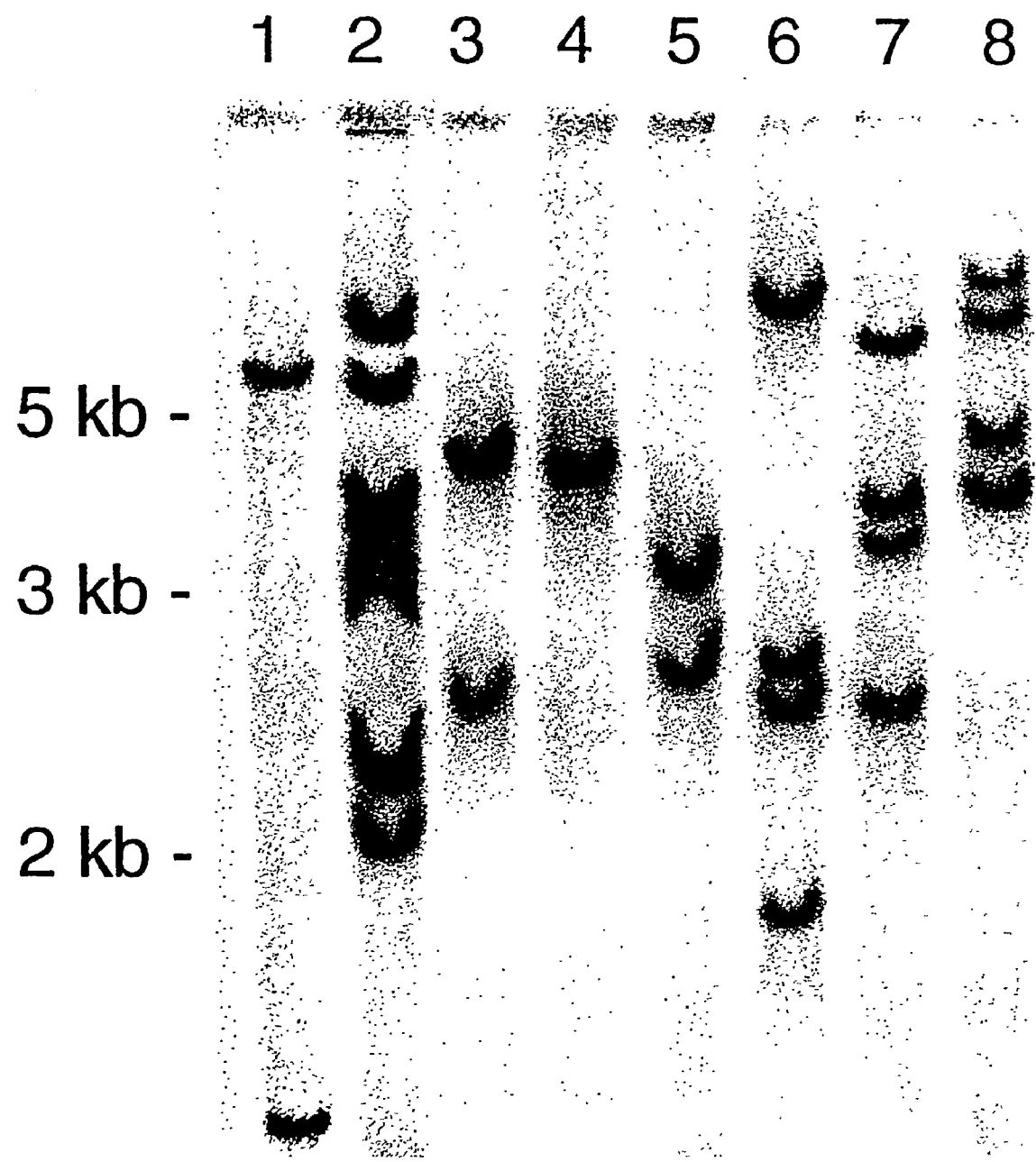
FIG. 7(A) illustrates the results of a southern hybridization of HeLa cell genomic DNA with neomycin-specific radiolabeled probe from 8 individual HeLa cell clones that had been cotransfected with pT/neo and pSB10 and survived G-418 selection. Genomic DNA was digested with the restriction enzymes NheI, XhoI, BglII, SpeI and XbaI, enzymes that do not cut within the neo-marked transposon, prior to agarose gel electrophoresis and blotting.

Upon cotransfection of the two-component SB transposon system into cultured vertebrate cells, transposase activity manifested as enhanced integration of the transgene serving as the DNA substrate for transposase. The binding of transposase to a donor construct and subsequent active transport of these nucleoprotein complexes into the nuclei of transfected cells could have resulted in elevated integration rates, as observed for transgenic zebrafish embryos using an SV40 NLS peptide (Collas et al., 1996 *Transgenic Res.* 5, 451–458). However, DNA-binding and nuclear targeting activities alone did not increase transformation frequency, which occurred only in the presence of full-length transposase. Although not sufficient, these functions are probably necessary for transposase activity. Indeed, a single amino acid replacement in the NLS of mariner is detrimental to overall transposase function (Lohe et al., 1997 *Proc. Nail.* *Acad. Sci. USA* 94, 1293–1297). The inability of SB6, a mutated version of the transposase gene, to catalyze transposition demonstrates the importance of the sequences of the conserved motifs. Notably, three of the 11 amino acid substitutions that SB6 contains, F(21), N(28) and H(31) are within the specific DNA-binding domain (FIGS. 1 and 2). Sequence analysis of the paired-like DNA-binding domain of fish TcE transposases indicates that an isoleucine at position 28 is conserved between the transposases and the corresponding positions in the Pax proteins (Ivics et al., 1996, supra). Thus, we predict that this motif is crucial for DNA-binding activity. SB exhibits substrate-dependence for specific recognition and integration; only those engineered transposons that have both of the terminal inverted repeats can be transposed by SB. Similarly, in P element transformation in *Drosophila*, the transposase-producing helper construct is often a "wings-clipped" transposase gene which lacks one of the inverted repeats of P which prevents the element from jumping (Cooley et al., 1988 *Science* 239, 1121–1128). In our transient assay, transposition can only occur if both components of the SB system are present in the same cell. Once that happens, multiple integrations can take place as demonstrated by our finding of up to 11 integrated transgenes in neomycin-resistant cell clones (FIG. 7A). In contrast to spontaneous integration of plasmid DNA in cultured mammalian cells that often occurs in the form of concatemeric multimers into a single genomic site (Perucho et al., 1980 *Cell* 22, 309–317), these multiple insertions appear to have occurred in distinct chromosomal locations.

Integration of our synthetic, salmonid transposons was observed in fish as well as in mouse and human cells. In addition, recombination of genetic markers in a plasmid-to-plasmid transposition assay (Lampe et al., 1996, supra) was significantly enhanced in microinjected zebrafish embryos in the presence of transposase. Consequently, SB apparently does not need any obvious, species-specific factor that would restrict its activity to its original host. Importantly, the most significant enhancement, about 20-fold, of transgene integration was observed in human cells as well as fish embryonic cells.

Integration Activity of SB

In addition to the abilities to enter nuclei and specifically bind to its sites of action within the inverted repeats, a fully active transposase is expected to excise and integrate transposons. In the C-terminal half of the SB transposase, three protein motifs make up the DD(34)E catalytic domain; the two invariable aspartic acid residues, D(153) and D(244), and a glutamic acid residue, E(279), the latter two being separated by 34 amino acids (FIG. 2). An intact DD(34)E box is essential for catalytic functions of Tc1 and Tc3 transposases (van Luenen et al., 1994 *Cell* 79, 293–301; Vos and Plasterk, 1994, supra).

Figure 5A:
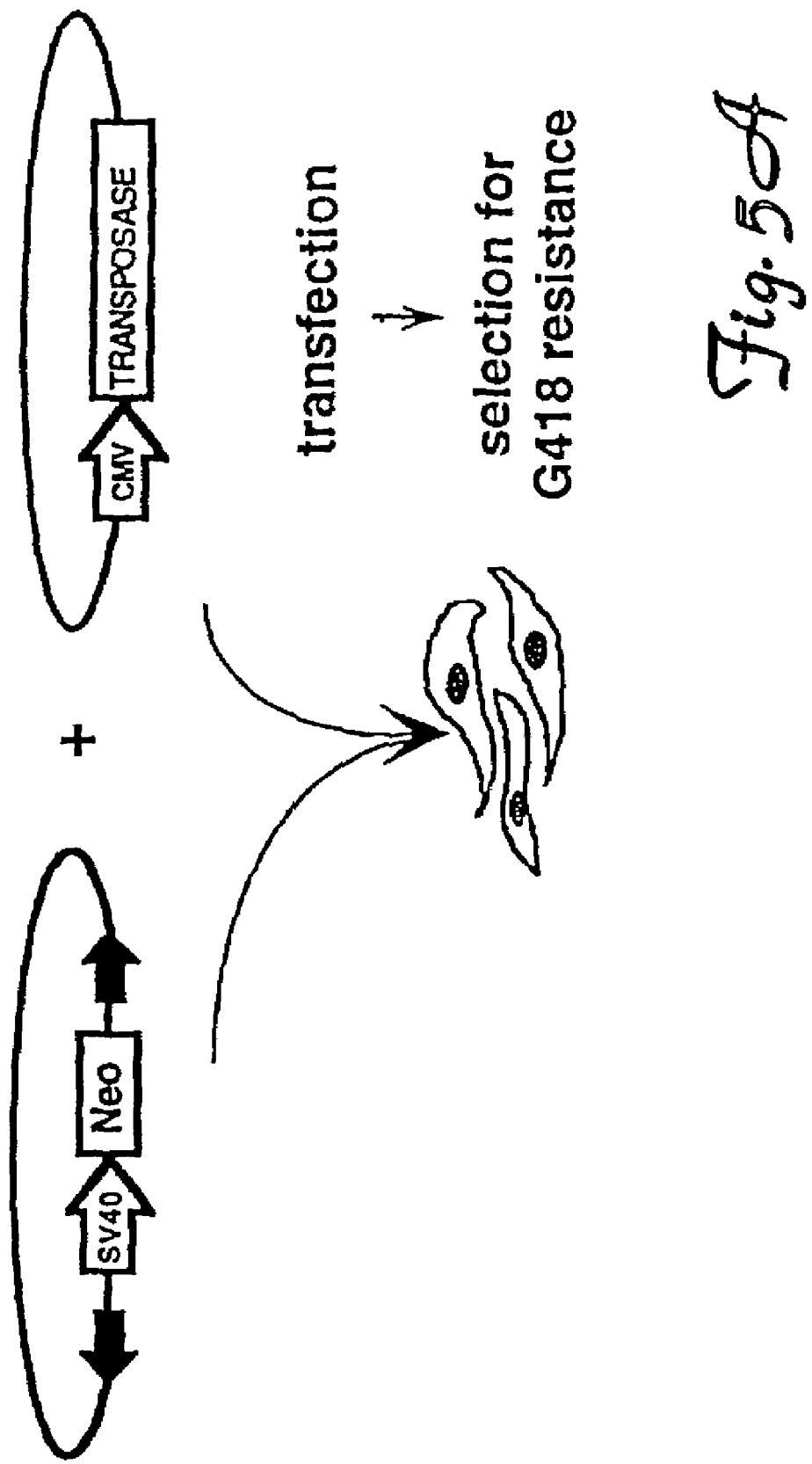
FIG. 5(A) is a schematic illustrating the genetic assay strategy for SB-mediated transgene integration in cultured cells.
Figure 5B:
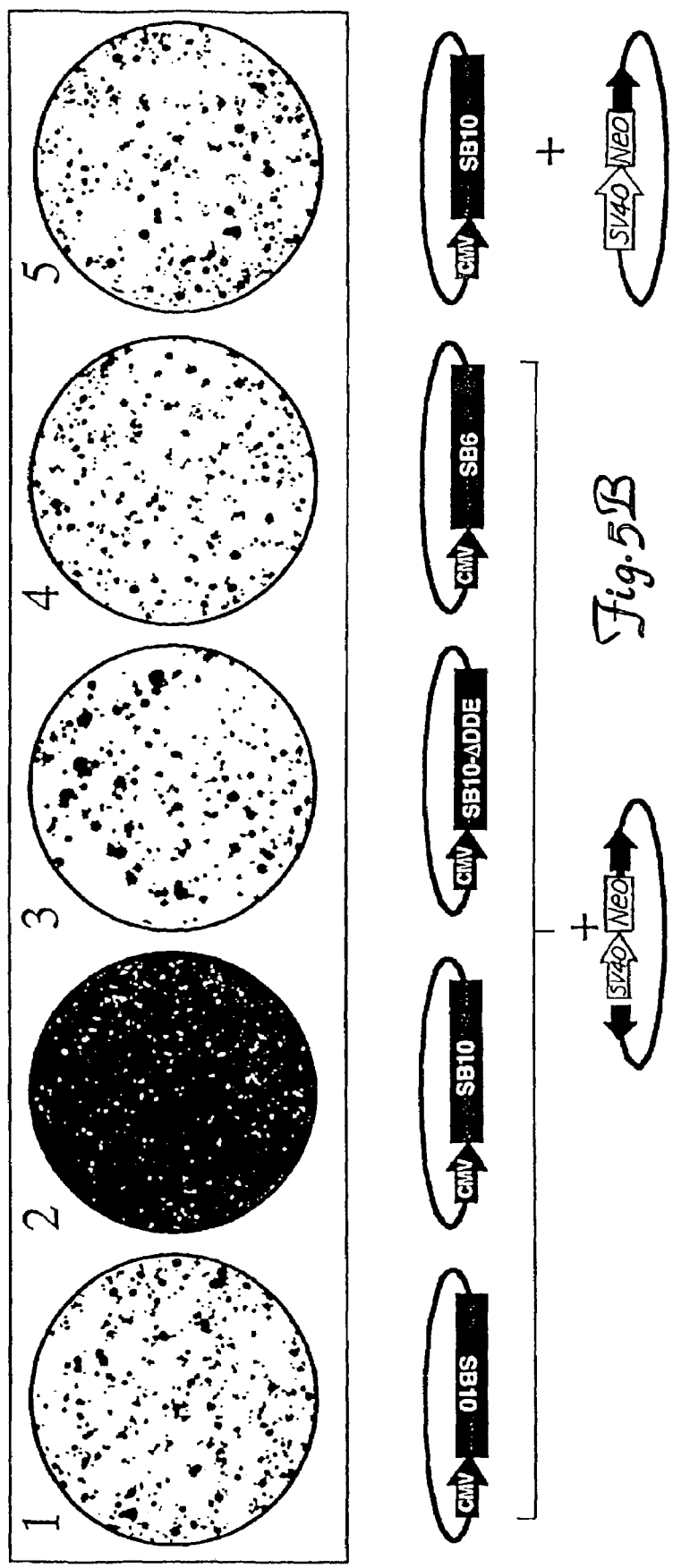
FIG. 5(B) demonstrates HeLa cell integration using Petri dishes of HeLa cells with stained colonies of G-418-resistant HeLa cells that were transfected with different combinations of donor and helper plasmids. Plate: 1) pT/neo plus pSB10-AS; 2) pT/neo plus pSB10; 3) pT/neo plus pSB10-ΔDDE; 4) pT/neo plus pSB6; 5) pT/neo-ΔIR plus pSB10.
Figure 6:
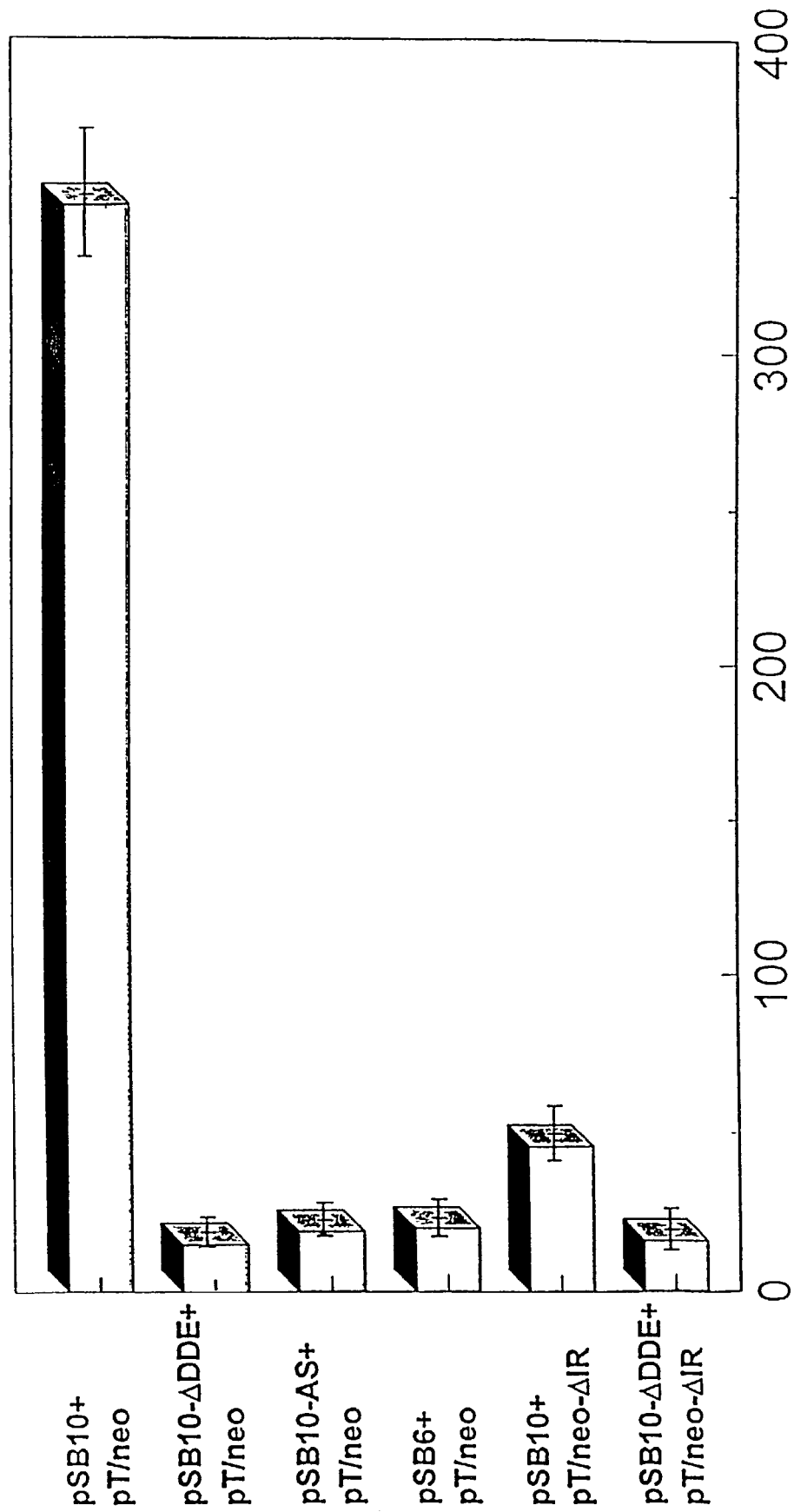
FIG. 6 summarizes the results of transgene integration in human HeLa cells. Integration was dependent on the presence of an active SB transposase and a transgene flanked by transposon inverted repeats. Different combinations of the indicated donor and helper plasmids were cotransfected into cultured HeLa cells and one tenth of the cells, as compared to the experiments shown in FIG. 5, were plated under selection to count transformants. The efficiency of transgene integration was scored as the number of transformants surviving antibiotic selection. Numbers of transformants at right represent the numbers of G-418-resistant cell colonies per dish. Each number represents the average obtained from three transfection experiments.

Two different integration assays were used. A first assay was designed to detect chromosomal integration events into the chromosomes of cultured cells. The assay is based on trans-complementation of two nonautonomous transposable elements, one containing a selectable marker gene (donor) and another that expresses the transposase (helper) (FIG. 5A). The donor, pT/neo, is an engineered, T-based element which contains an SV40 promoter-driven neo gene flanked by the terminal IRs of the transposon containing binding sites for the transposase. The helper construct expresses the full-length SB10 transposase gene driven by a human cytomegalovirus (CMV) enhancer/promoter. In the assay, the donor plasmid is cotransfected with the helper or control constructs into cultured vertebrate cells, and the number of cell clones that are resistant to the neomycin analog drug G-418 due to chromosomal integration and expression of the neo transgene serves as an indicator of the efficiency of gene transfer. If SB is not strictly host-specific, transposition should also occur in phylogenetically distant vertebrate species. Using the assay system shown in FIG. 5A, enhanced levels of transgene integration were observed in the presence of the helper plasmid; more than 5-fold in mouse LMTK cells and more than 20-fold in human HeLa cells (FIGS. 5B and 6). Consequently, SB appears to be able to increase the efficiency of transgene integration, and this activity is not restricted to fish cells.

To analyze the requirements for enhanced transgene integration, further experiments were conducted. FIG. 5B shows five plates of transfected HeLa cells that were placed under G-418 selection, and were stained with methylene blue two weeks post-transfection. The staining patterns clearly demonstrate a significant increase in integration of neo-marked transposons into the chromosomes of HeLa cells when the SB transposase-expressing helper construct was cotransfected (plate 2), as compared to a control cotransfection of the donor plasmid plus the SB transposase gene cloned in an antisense orientation (pSB10-AS; plate 1). This result indicates that the production of transposase protein was essential for enhanced chromosomal integration of the transgene and demonstrates that the transposase is precise even in human cells.

Figure 8:
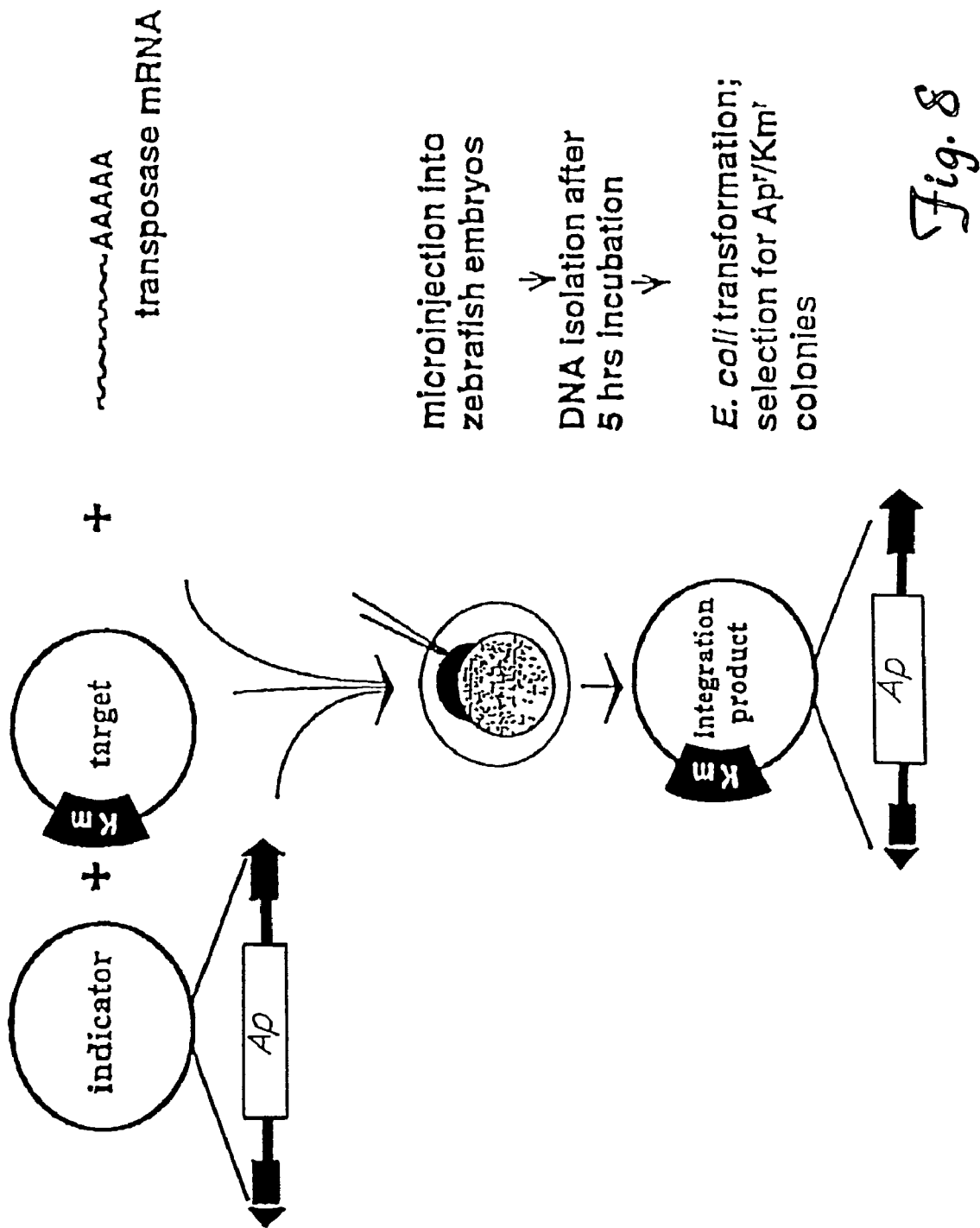
FIG. 8 is a schematic demonstrating an interplasmid assay for excision and integration of a transposon. The assay was used to evaluate transposase activity in zebrafish embryos. Two plasmids plus an RNA encoding an SB transposase protein were coinjected into the one-cell zebrafish embryo. One of the plasmids had an ampicillin resistance gene (Ap) flanked by IR/DR sequences recognizable by the SB transposase. Five hours after fertilization and injection, low molecular weight DNA was isolated from the embryos and used to transform *E. coli*. The bacteria were grown on media containing ampicillin and kanamycin (Km) to select for bacteria harboring single plasmids containing both the Km and Ap antibiotic-resistance markers. The plasmids from doubly resistant cells were examined to confirm that the Ap-transposon was excised and reintegrated into the Km target plasmid. Ap-transposons that moved into either another indicator Ap-plasmid or into the zebrafish genome were not scored. Because the amount of DNA in injected plasmid was almost equal to that of the genome, the number of integrations of Ap-transposons into target plasmids approximated the number of integrations into the genome.

In a second assay, an indicator plasmid containing the transposase recognition sequence and a marker gene (Ampicillin resistance) was co-injected with a target plasmid containing a kanamycin gene and SB transposase. Resulting plasmids were isolated and used to transform *E. coli*. Colonies were selected for ampicillin and kanamycin resistance (see FIG. 8). While SB transposase was co-microinjected in these assays, mRNA encoding the SB transposase could also be co-microinjected in place of or in addition to, the SB transposase protein.

Cell Transfections

Cells were cultured in DMEM supplemented with 10% fetal bovine serum, seeded onto 6 cm plates one day prior to transfection and transfected with 5 μg Elutip (Schleicher and Schuell)-purified plasmid DNA using Lipofectin from BRL. After 5 hrs of incubation with the DNA-lipid complexes, the cells were "glycerol-shocked" for 30 sec with 15% glycerol in phosphate buffered saline (PBS), washed once with PBS and then refed with serum-containing medium. Two days post-transfection, the transfected cells were trypsinized, resuspended in 2 ml of serum-containing DMEM and either 1 ml or 0.1 ml aliquots of this cell suspension were seeded onto several 10 cm plates in medium containing 600 μg/ml G-418 (BRL). After two weeks of selection, cell clones were either picked and expanded into individual cultures or fixed with 10% formaldehyde in PBS for 15 min, stained with methylene blue in PBS for 30 min, washed extensively with deionized water, air dried and photographed.

These assays can also be used to map transposase domains necessary for chromosomal integration. For this assay, a frameshift mutation was introduced into the SB transposase gene which put a translational stop codon behind G(161). This construct, pSB10-ΔDDE, expresses a truncated transposase polypeptide that contains specific DNA-binding and NLS domains, but lacks the catalytic domain. The transformation rates obtained using this construct (plate 3 in FIG. 5B) were similar to those obtained with the antisense control (FIG. 6). This result suggests that the presence of a full-length transposase protein is necessary and that DNA-binding and nuclear transport activities themselves are not sufficient for the observed enhancement of transgene integration.

As a further control of transposase requirement, the integration activity of an earlier version of the SB transposase gene was tested, SB6 which differs from SB10 at 11 residues, FIG. 1B), using the same assay. The number of transformants observed using SB6 (plate 4 in FIG. 5B) was about the same as with the antisense control experiment (FIG. 6), indicating that the amino acid replacements that we introduced into the transposase gene were critical for transposase function. In summary, the three controls shown in plates 1, 3, and 4 of FIG. 5B establish the trans-requirements of enhanced, SB-mediated transgene integration.

True transposition requires a transposon with intact IR sequences. One of the IRs of the neo-marked transposon substrate was removed, and the performance of this construct, pT/neo-ΔIR, was tested for integration. The transformation rates observed with this plasmid (plate 5 in FIG. 5B) were more than 7-fold lower than those with the full-length donor (FIG. 6). These results indicated that both of the IRs flanking the transposon are required for efficient transposition and thereby establish some of the cis-requirements of the two-component SB transposon system.

To examine the structures of integrated transgenes, eleven colonies of cells growing under G-418 selection from an experiment similar to that shown in plate 2 in FIG. 5B were picked and their DNAs analyzed using Southern hybridization. Genomic DNA samples of the cell clones were digested with a combination of five restriction enzymes that do not cut within the 2233 bp T/neo marker transposon, and hybridized with a neo-specific probe (FIG. 7). The hybridization patterns indicated that all of the analyzed clones contained integrated transgenes in the range of 1 (lane 4) to 11 (lane 2) copies per transformant. Moreover, many of the multiple insertions appear to have occurred in different locations in the human genome.

Figure 7B:
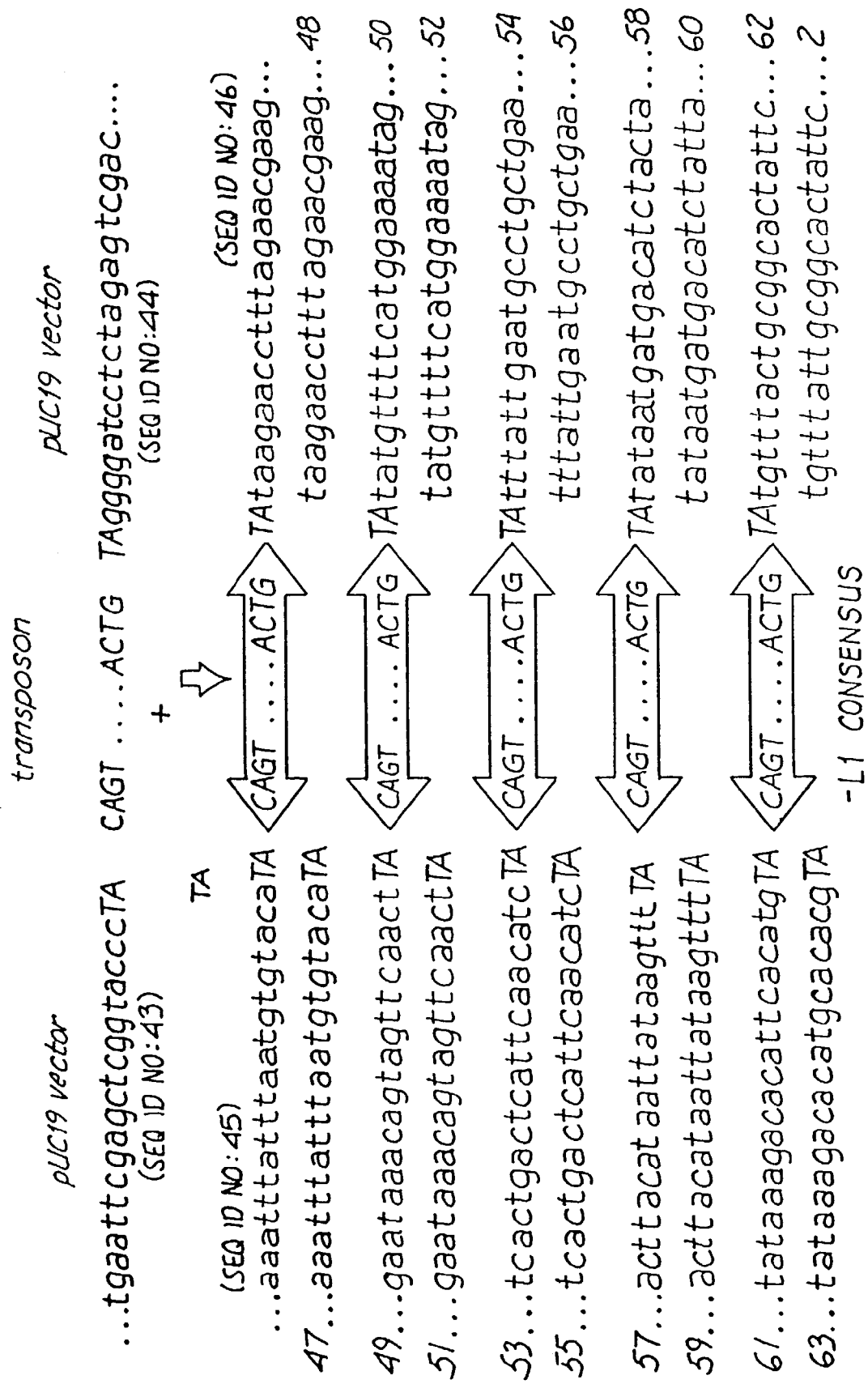
FIG. 7(B) is a diagram of the junction sequences (SEQ ID NOS:43–63 and SEQ ID NO:2) of T/neo transposons integrated into human genomic DNA. The donor site is illustrated on top with plasmid vector sequences that originally flanked the transposon in pT/neo (arrows). IR sequences are boxed in the arrows.

The presence of duplicated TA sequences flanking an integrated transposon is a hallmark of TcE transposition. To reveal such sequences, junction fragments of integrated transposons and human genomic DNA were isolated using a ligation-mediated PCR assay (Devon et al., *Nucl. Acids. Res.*, 23, 1644–1645 (1995)). We have cloned and sequenced junction fragments of five integrated transposons, all of them showing the predicted sequences of the IRs which continue with TA dinucleotides and sequences that are different in all of the junctions and different from the plasmid vector sequences originally flanking the transposon in pT/neo (FIG. 7B). The same results were obtained from nine additional junctions containing either the left or the right IR of the transposon (data not shown). These results indicated that the marker transposons had been precisely excised from the donor plasmids and subsequently spliced into various locations in human chromosomes. Next, the junction sequences were compared to the corresponding "empty" chromosomal regions cloned from wild-type HeLa DNA. As shown in FIG. 7B, all of these insertions had occurred into TA target sites, which were subsequently duplicated to result in TA's flanking the integrated transposons. These data demonstrate that SB uses the same, cut-and-paste-type mechanism of transposition as other members of the Tc1/mariner superfamily and that fidelity of the reaction is maintained in heterologous cells. These data also suggest that the frequency of SB-mediated transposition is at least 15-fold higher than random recombination. Since none of the sequenced recombination events were mediated by SB-transposase, the real rate of transposition over random recombination could be many fold higher. If the integration is the result of random integration that was not mediated by the SB protein, the ends of the inserted neo construct would not correspond to the ends of the plasmids; there would have been either missing IR sequences and/or additional plasmid sequences that flank the transposon. Moreover, there would not have been duplicated TA basepairs at the sites of integration.

Taken together, the dependence of excision and integration, from extrachromosomal plasmids to the chromosomes of vertebrate cells, of a complete transposon with inverted repeats at both ends by a full-length transposase enzyme demonstrates that the gene transfer system is fully functional.

EXAMPLE 5

Transposition of DNA in Cells from Different Species

Host-requirements of transposase activity were assessed using three different vertebrate cells, LMTK from mouse and HeLa from human and embryonic cells from the zebrafish.

An assay was designed to demonstrate that the transposase worked in a functioning set of cells (i.e., embryonic cells that were differentiating and growing in a natural environment). The assay involved inter-plasmid transfer where the transposon in one plasmid is removed and inserted into a target plasmid and the transposase construct was injected into 1-cell stage zebra fish embryos. In these experiments the Indicator (donor) plasmids for monitoring transposon excision and/or integration included: 1) a marker gene that when recovered in *E. coli* or in fish cells, could be screened by virtue of either the loss or the gain of a function, and 2) transposase-recognition sequences in the IRs flanking the marker gene. The total size of the marked transposons was kept to about 1.6 kb, the natural size of the TcEs found in teleost genomes. However, the rate of gene transfer using transposons of about 5 kb is not significantly different from that for the 1.6 kb transposon, suggesting that transposition can occur with large transposons. The transposition activity of Ts1 transposase was evaluated by co-microinjecting 200 ng/μl of Ts1 mRNA, made in vitro by T7 RNA polymerase from a Bluescript expression vector, plus about 250 ng/μl each of target and donor plasmids into 1-cell stage zebrafish embryos. Low molecular weight DNA was prepared from the embryos at about 5 hrs post-injection, transformed into *E. coli* cells, and colonies selected by replica plating on agar containing 50 μg/ml kanamycin and/or ampicillin. In these studies there was a transposition frequency into the target plasmid was about 0.041% in experimental cells as compared to 0.002% in control cells. This level did not include transpositions that occurred in the zebrafish genome. In these experiments we found that about 40% to 50% of the embryos did not survive beyond 4 days. Insertional mutagenesis studies in the mouse have suggested that the rate of recessive lethality is about 0.05 (i.e., an average of about 20 insertions will be lethal). Assuming that this rate is applicable to zebrafish, the approximate level of mortality suggests that with the microinjection conditions used in these experiments, about 20 insertions per genome, the mortality can be accounted for.

EXAMPLE 6

Stable Gene Expression from SB Transposons

A transposon system will be functional for gene transfer, for such purposes as gene therapy and gene delivery to animal chromosomes for bioreactor systems, only if the delivered genes are reliably expressed. To determine the fidelity of gene expression following Sleeping Beauty transposase-mediated delivery, we co-microinjected a transposon containing the Green Fluorescent Protein (GFP) gene under the direction of an SV40 promoter plus in vitro-synthesized mRNA encoding Sleeping Beauty transposase into 1-cell zebrafish embryos. 34 of the injected embryos, that showed some expression of GFP during embryogenesis, were allowed to grow to maturity and were mated with wild-type zebrafish. From these matings we found that 4 of the 34 fish could transfer a GFP gene to their progeny (Table 1). The expression of GFP in the offspring of these four F0 fish, identified as A, B, C, and D, was evaluated and the fish were grown up. From the original four founders, the rate of transmission of the GFP gene ranged from about 2% to 12% (Table 1), with an average of about 7%. The expression of GFP in these fish was nearly the same in all individuals in the same tissue types, suggesting that expression of the GFP gene could be revived following transmission through eggs and sperm. These data suggest that the germ-lines were mosaic for expressing GFP genes and that the expression of the genes was stable. The F1 offspring of Fish D were mated with each other. In this case we would expect about 75% transmission and we found that indeed 69/90 (77%) F2 fish expressed the GFP protein at comparable levels in the same tissues; further testimony of the ability of the SB transposon system to deliver genes that can be reliably expressed through at least two generations of animal.

TABLE 1

Stability of gene expression in zebrafish following injection of a SB transposon containing the GFP gene.

| | Expression of GFP | | |
|---|---|---|---|
| Transgenic Line | F0 | F1 | F2 |
| 34 founders | 34 (of which 4 progeny, A–D, passed on the transgene) | | |
| A | | 25/200 (12%) | |
| B | | 76/863 (9%) | |
| C | | 12/701 (2%) | |
| D | | 86/946 (10%) | 69/90 (77%) |

The numbers in the columns for fish A–D show the numbers of GFP expressing fish followed by the total number of offspring examined. The percentages of GFP-expressing offspring are given in parentheses.

EXAMPLE 7

SB Transposons for Insertional Mutagenesis and Gene Discovery

Due to their inherent ability to move from one chromosomal location to another within and between genomes, transposable elements have revolutionized genetic manipulation of certain organisms including bacteria (Gonzales et al., 1996 *Vet. Microbiol.* 48, 283–291; Lee and Henk, 1996. *Vet. Microbiol.* 50, 143–148), *Drosophila* (Ballinger and Benzer, 1989 *Proc. Natl. Acad. Sci. USA* 86, 9402–9406; Bellen et al., 1989 *Genes Dev.* 3, 1288–1300; Spradling et al., 1995 *Proc. Natl. Acad. Sci. U.S. Pat. No.* 92, 10824–10830), *C. elegans* (Plasterk, 1995. *Meth. Cell. Biol.*, Academic Press, Inc. pp. 59–80) and a variety of plant species (Osborne and Baker, *Curr. Opin. Cell Biol*, 7, 406–413 (1995)). Transposons have been harnessed as useful vectors for transposon-tagging, enhancer trapping and transgenesis. However, the majority, if not all, animals of economic importance lack such a tool. For its simplicity and apparent ability to function in diverse organisms, SB should prove useful as an efficient vector for species in which DNA transposon technology is currently not available.

An SB-type transposable element can integrate into either of two types of chromatin, functional DNA sequences where it may have a deleterious effect due to insertional mutagenesis or non-functional chromatin where it may not have much of a consequence (FIG. 9). This power of "transposon tagging" has been exploited in simpler model systems for nearly two decades (Bingham et al., *Cell*, 25, 693–704 (1981); Bellen et al., 1989, supra). Transposon tagging is an old technique in which transgenic DNA is delivered to cells so that it will integrate into genes, thereby inactivating them by insertional mutagenesis. In the process, the inactivated genes are tagged by the transposable element which then can be used to recover the mutated allele. Insertion of a transposable element may disrupt the function of a gene which can lead to a characteristic phenotype. As illustrated in FIG. 10, because insertion is approximately random, the same procedures that generate insertional, loss-of-function mutants can often be used to deliver genes that will confer new phenotypes to cells. Gain-of-function mutants can be used to understand the roles that gene products play in growth and development as well as the importance of their regulation.

There are several ways of isolating the tagged gene. In all cases genomic DNA is isolated from cells from one or more tissues of the mutated animal by conventional techniques (which vary for different tissues and animals). The DNA is cleaved by a restriction endonuclease that may or may not cut in the transposon tag (more often than not it does cleave at a known site). The resulting fragments can then either be directly cloned into plasmids or phage vectors for identification using probes to the transposon DNA (see Kim et al., 1995 for references in *Mobile Genetic Elements*, IRL Press, D. L. Sheratt eds.). Alternatively, the DNA can be PCR amplified in any of many ways; we have used the LM-PCR procedure of Izsvak and Ivics (1993, supra) and a modification by Devon et al. (1995, supra) and identified by its hybridization to the transposon probe. An alternative method is inverse-PCR (e.g., Allende et al., *Genes Dev.*, 10, 3141–3155 (1996)). Regardless of method for cloning, the identified clone is then sequenced. The sequences that flank the transposon (or other inserted DNA) can be identified by their non-identity to the insertional element. The sequences can be combined and then used to search the nucleic acid databases for either homology with other previously characterized gene(s), or partial homology to a gene or sequence motif that encodes some function. In some cases the gene has no homology to any known protein. It becomes a new sequence to which others will be compared. The encoded protein will be the center of further investigation of its role in causing the phenotype that induced its recovery.

EXAMPLE 8

SB Transposons as Markers for Gene Mapping

Repetitive elements for mapping transgenes and other genetic loci have also been identified. DANA is a retroposon with an unusual substructure of distinct cassettes that appears to have been assembled by insertions of short sequences into a progenitor SINE element. DANA has been amplified in the Danio lineage to about $4 \times 10^5$ copies/genome. Angel elements, which are nearly as abundant as DANA, are inverted-repeat sequences that are found in the vicinity of fish genes. Both DANA and Angel elements appear to be randomly distributed in the genome, and segregate in a Medelian fashion. PCR amplifications using primers specific to DANA and Angel elements can be used as genetic markers for screening polymorphisms between fish stocks and localization of transgenic sequences. Interspersed repetitive sequence-PCR (IRS-PCR) can be used to detect polymorphic DNA. IRS-PCR amplifies genomic DNA flanked by repetitive elements, using repeat-specific primers to produce polymorphic fragments that are inherited in a Medelian fashion (FIG. 10A). Polymorphic DNA fragments can be generated by DANA or Angel specific primers in IRS-PCR and the number of detectable polymorphic bands can be significantly increased by the combination of various primers to repetitive sequences in the zebrafish genome, including SB-like transposons.

Polymorphic fragments can be recovered from gels and cloned to provide sequence tagged sites (STSs) for mapping mutations. FIG. 10B illustrates the general principles and constraints for using IRS-PCR to generate STSs. We estimate that about 0.1% of the zebrafish genome can be directly analyzed by IRS-PCR using only 4 primers. The four conserved (C1–4) regions of DANA seem to have different degrees of conservation and representation in the zebrafish genome and this is taken into account when designing PCR primers.

The same method has a potential application in fingerprinting fish stocks and other animal populations. The method can facilitate obtaining subclones of large DNAs cloned in yeast, bacterial and bacteriophage P1-derived artificial chromosomes (YACs, BACs and PACs respectively) and can be used for the detection of integrated transgenic sequences.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A nucleic acid fragment comprising:
a nucleic acid sequence positioned between at least two inverted repeats that bind to an SB protein, the inverted repeats comprising at least one direct repeat, wherein each direct repeat comprises a nucleic acid sequence that has at least 80% nucleic acid sequence identity to SEQ ID NO:10 and wherein each direct repeat binds to the SB protein;
wherein the SB protein comprises an amino acid sequence having at least 80% identity to SEQ ID NO:1 and binds to at least one of SEQ ID NO:4 and SEQ ID NO:5.

2. The fragment of claim 1 wherein the nucleic acid fragment is part of a plasmid.

3. The fragment of claim 1 wherein the nucleic acid sequence comprises at least a portion of an open reading frame.

4. The fragment of claim 1 wherein the nucleic acid sequence comprises at least one expression control region.

5. The fragment of claim 4 wherein the expression control region is selected from the group consisting of a promoter, an enhancer and a silencer.

6. The fragment of claim 1 wherein the nucleic acid sequence comprises a promoter operably linked to at least a portion of an open reading frame.

7. The nucleic acid fragment of claim 1 wherein at least one of the inverted repeats comprises SEQ ID NO:4 or SEQ ID NO:5.

8. A nucleic acid fragment comprising:
a nucleic acid sequence positioned between at least two inverted repeats that bind to an SB protein, the inverted repeats comprising at least one direct repeat, wherein each direct repeat comprises a nucleic acid sequence that has at least 80% nucleic acid sequence identity to SEQ ID NO:10 and wherein each direct repeat binds to the SB protein;
wherein the SB protein comprises SEQ ID NO:1.

9. A nucleic acid fragment having at least 80% nucleic acid sequence identity to SEQ ID NO:10, wherein the nucleic acid fragment binds to an SB protein;
wherein the SB protein comprises an amino acid sequence having at least 80% identity to SEQ ID NO:1 and binds to at least one of SEQ ID NO:4 and SEQ ID NO:5.

10. The nucleic acid fragment of claim 9 wherein the SB protein comprises SEQ ID NO:1.

11. A gene transfer system comprising:
a transposase or a nucleic acid encoding a transposase, wherein the transposase is an SB protein; and
a nucleic acid fragment comprising a nucleic acid sequence positioned between at least two inverted repeats that bind to an SB protein, the inverted repeats comprising at least one direct repeat, wherein each direct repeat comprises a nucleic acid sequence that has at least 80% nucleic acid sequence identity to SEQ ID NO:10 and wherein each direct repeat binds to the SB protein;
wherein the SB protein comprises an amino acid sequence having at least 80% identity to SEQ ID NO:1 and binds to at least one of SEQ ID NO:4 and SEQ ID NO:5.

12. The gene transfer system of claim 11 wherein the SB protein comprises SEQ ID NO:1.

13. The gene transfer system of claim 11 wherein the nucleic acid encoding a transposase is RNA.

14. The gene transfer system of claim 11 wherein the nucleic acid encoding the transposase is integrated into the genome of a cell.

15. The gene transfer system of claim 11 wherein the nucleic acid fragment is part of a plasmid or a recombinant viral vector.

16. The gene transfer system of claim 11 wherein the nucleic acid sequence comprises at least a portion of an open reading frame.

17. The gene transfer system of claim 11 wherein the nucleic acid sequence comprises at least a regulatory region of a gene.

18. The gene transfer system of claim 17 wherein the regulatory region is a transcriptional regulatory region.

19. The gene transfer system of claim 17 wherein the regulatory region is selected from the group consisting of a promoter, an enhancer, a silencer, a locus-control region, and a border element.

20. The gene transfer system of claim 11 wherein the nucleic acid sequence comprises a promoter operably linked to at least a portion of an open reading frame.

21. The gene transfer system of claim 11 wherein at least one of the inverted repeats comprises SEQ ID NO:4 or SEQ ID NO:5.

22. The gene transfer system of claim 11 wherein the nucleic acid sequence is obtained from a library of recombinant sequences.

23. The gene transfer system of claim 11 wherein the nucleic acid sequence is introduced into a cell using a method selected from the group consisting of particle bombardment, electroporation, microinjection, combining the nucleic acid fragment with lipid-containing vesicles or DNA condensing reagents, and incorporating the nucleic acid fragment into a viral vector and contacting the viral vector with the cell.

24. A method for introducing nucleic acid into DNA in an isolated or cultured vertebrate cell comprising the step of:
  introducing into the cell a nucleic acid fragment comprising a nucleic acid sequence positioned between at least two inverted repeats that bind to an SB protein, the inverted repeats comprising at least one direct repeat, wherein each direct repeat comprises a nucleic acid sequence that has at least 80% nucleic acid sequence identity to SEQ ID NO:10 and wherein each direct repeat binds to the SB protein;
  wherein the SB protein comprises an amino acid sequence having at least 80% identity to SEQ ID NO:1 and binds to at least one of SEQ ID NO:4 and SEQ ID NO:5.

25. The method of claim 24 further comprising introducing the SB protein into the cell.

26. The method of claim 25 wherein the SB protein is introduced to the cell as RNA.

27. The method of claim 24 wherein the cell comprises nucleic acid encoding the SB protein.

28. The method of claim 27 wherein the nucleic acid encoding the SB protein is integrated into the cell genome.

29. The method of claim 27 wherein the SB protein is stably expressed in the cell.

30. The method of claim 27 wherein the SB protein is under the control of an inducible promoter.

31. The method of claim 24 wherein introducing the nucleic acid fragment into the cell comprises using a method selected from the group consisting of microinjection, electroporation, combining the nucleic acid fragment with cationic lipid vesicles or DNA condensing reagents, and incorporating the nucleic acid fragment into a viral vector and contacting the viral vector with the cell.

32. The method of claim 31 wherein the viral vector is selected from the group consisting of a retroviral vector, an adenovirus vector and an adeno-associated viral vector.

33. The method of claim 24 further comprising introducing a DNA or an RNA encoding the SB protein into the cell.

34. The method of claim 24 wherein the nucleic acid sequence encodes a protein.

35. The method of claim 34 wherein the protein is a marker protein.

36. An isolated or cultured vertebrate cell producing the protein of claim 34.

37. The method of claim 24 wherein the SB protein comprises SEQ ID NO:1.

* * * * *

UNITED STATES PATENT AND TRADEMARK OFFICE
CERTIFICATE OF CORRECTION

PATENT NO. : 7,148,203 B2 Page 1 of 1
APPLICATION NO. : 10/263159
DATED : December 12, 2006
INVENTOR(S) : Hackett et al.

It is certified that error appears in the above-identified patent and that said Letters Patent is hereby corrected as shown below:

Column 1, Line 21
Delete "R01-RR0625" and insert --R01-RR06625--
Delete "USDOC/"

Column 1, Line 22
Delete "NA46RG O101-04" and insert --NA46RG 0101-04--

Signed and Sealed this

Twenty-third Day of September, 2008

JON W. DUDAS
*Director of the United States Patent and Trademark Office*

SEQUENCE LISTING (1) GENERAL INFORMATION:

(iii) NUMBER OF SEQUENCES: 63

(2) INFORMATION FOR SEQ ID NO: 1:

(i) SEQUENCE CHARACTERISTICS:
        (A) LENGTH: 340 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
                35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
            130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
                180                 185                 190

Met Leu Trp Gly Cys Phe Ala Ala Gly Gly Thr Gly Ala Leu His Lys
            195                 200                 205

Ile Asp Gly Ile Met Arg Lys Glu Asn Tyr Val Asp Ile Leu Lys Gln
            210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
            275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
TGTTTATTGC GGCACTATTC                                              20
```

(2) INFORMATION FOR SEQ ID NO: 3:

(i) SEQUENCE CHARACTERISTICS:
        (A) LENGTH: 1023 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
ATGGGAAAAT CAAAAGAAAT CAGCCAAGAC CTCAGAAAAA AAATTGTAGA CCTCCACAAG    60

TCTGGTTCAT CCTTGGGAGC AATTTCCAAA CGCCTGAAAG TACCACGTTC ATCTGTACAA   120

ACAATAGTAC GCAAGTATAA ACACCATGGG ACCACGCAGC CGTCATACCG CTCAGGAAGG   180

AGACGCGTTC TGTCTCCTAG AGATGAACGT ACTTTGGTGC GAAAAGTGCA AATCAATCCC   240

AGAACAACAG CAAAGGACCT TGTGAAGATG CTGGAGGAAA CAGGTACAAA AGTATCTATA   300

TCCACAGTAA AACGAGTCCT ATATCGACAT AACCTGAAAG GCCGCTCAGC AAGGAAGAAG   360

CCACTGCTCC AAAACCGACA TAAGAAAGCC AGACTACGGT TTGCAACTGC ACATGGGGAC   420

AAAGATCGTA CTTTTTGGAG AAATGTCCTC TGGTCTGATG AAACAAAAAT AGAACTGTTT   480

GGCCATAATG ACCATCGTTA TGTTTGGAGG AAGAAGGGGG AGGCTTGCAA GCCGAAGAAC   540

ACCATCCCAA CCGTGAAGCA CGGGGGTGGC AGCATCATGT TGTGGGGGTG CTTTGCTGCA   600

GGAGGGACTG GTGCACTTCA CAAAATAGAT GGCATCATGA GGAAGGAAAA TTATGTGGAT   660

ATATTGAAGC AACATCTCAA GACATCAGTC AGGAAGTTAA AGCTTGGTCG CAAATGGGTC   720

TTCCAAATGG ACAATGACCC CAAGCATACT TCCAAAGTTG TGGCAAAATG GCTTAAGGAC   780

AACAAAGTCA AGGTATTGGA GTGGCCATCA CAAAGCCCTG ACCTCAATCC TATAGAAAAT   840

TTGTGGGCAG AACTGAAAAA GCGTGTGCGA GCAAGGAGGC CTACAAACCT GACTCAGTTA   900

CACCAGCTCT GTCAGGAGGA ATGGGCCAAA ATTCACCCAA CTTATTGTGG GAAGCTTGTG   960

GAAGGCTACC CGAAACGTTT GACCCAAGTT AAACAATTTA AAGGCAATGC TACCAAATAC  1020

TAG                                                              1023
```

(2) INFORMATION FOR SEQ ID NO: 4:

(i) SEQUENCE CHARACTERISTICS:
        (A) LENGTH: 226 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
AGTTGAAGTC GGAAGTTTAC ATACACTTAA GTTGGAGTCA TTAAAACTCG TTTTTCAACT    60
```

```
ACACCACAAA TTTCTTGTTA ACAAACAATA GTTTTGGCAA GTCAGTTAGG ACATCTACTT        120

TGTGCATGAC ACAAGTCATT TTTCCAACAA TTGTTTACAG ACAGATTATT TCACTTATAA        180

TTCACTGTAT CACAATTCCA GTGGGTCAGA AGTTTACATA CACTAA                      226
```

(2) INFORMATION FOR SEQ ID NO: 5:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
TTGAGTGTAT GTTAACTTCT GACCCACTGG GAATGTGATG AAAGAAATAA AAGCTGAAAT         60

GAATCATTCT CTCTACTATT ATTCTGATAT TTCACATTCT TAAAATAAAG TGGTGATCCT        120

AACTGACCTT AAGACAGGGA ATCTTTACTC GGATTAAATG TCAGGAATTG TGAAAAAGTG        180

AGTTTAAATG TATTTGGCTA AGGTGTATGT AAACTTCCGA CTTCAACTG                   229
```

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
GTTCAAGTCG GAAGTTTACA TACACTTAG                                          29
```

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
CAGTGGGTCA GAAGTTTACA TACACTAAGG                                         30
```

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
CAGTGGGTCA GAAGTTAACA TACACTCAAT T                                       31
```

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 9:

AGTTGAATCG GAAGTTTACA TACACCTTAG                                                30

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CAKTGRGTCR GAAGTTTACA TACACTTAAG                                                30

(2) INFORMATION FOR SEQ ID NO: 11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

ACATACAC                                                                         8

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

TTTCAGTTTT GGGTGAACTA TCC                                                       23

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GGCGACRCAG TGGCGCAGTR GG                                                        22

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

```
    (xi) SEQUENCE DESCRIPTION: SEQ ID NO: 14:

GAAYRTGCAA ACTCCACACA GA                                          22

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

TCCATCAGAC CACAGGACAT                                             20

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

TGTCAGGAGG AATGGGCCAA AATTC                                       25

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

CCTCTAGGAT CCGACATCAT G                                           21

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

TCTAGAATTC TAGTATTTGG TAGCATTG                                    28

(2) INFORMATION FOR SEQ ID NO: 19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

AACACCATGG GACCACGCAG CCGTCA                                      26
```

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CAGGTTATGT CGATATAGGA CTCGTTTTAC          30

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

CCTTGCTGAG CGGCCTTTCA GGTTATGTCG          30

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

TTGCACTTTT CGCACCAA          18

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

GTACCTGTTT CCTCCAGCAT C          21

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GAGCAGTGGC TTCTTCCT          18

(2) INFORMATION FOR SEQ ID NO: 25:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

CCACAACATG ATGCTGCC                                                     18

(2) INFORMATION FOR SEQ ID NO: 26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

TGGCCACTCC AATACCTTGA C                                                 21

(2) INFORMATION FOR SEQ ID NO: 27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

ACACTCTAGA CTAGTATTTG GTAGCATTGC C                                      31

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

GTGCTTCACG GTTGGGATGG TG                                                22

(2) INFORMATION FOR SEQ ID NO: 29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

ATTTTCTATA GGATTGAGGT CAGGGC                                            26

(2) INFORMATION FOR SEQ ID NO: 30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

GTCTGGTTCA TCCTTGGGAG CAATTTCCAA ACGCC                                    35

(2) INFORMATION FOR SEQ ID NO: 31:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 31:

CAAAACCGAC ATAAGAAAGC CAGACTACGG                                          30

(2) INFORMATION FOR SEQ ID NO: 32:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 32:

ACCATCGTTA TGTTTGGAGG AAGAAGGGGG AGGCTTGCAA GCCG                          44

(2) INFORMATION FOR SEQ ID NO: 33:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 33:

GGCATCATGA GGAAGGAAAA TTATGTGGAT ATATTG                                   36

(2) INFORMATION FOR SEQ ID NO: 34:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 34:

CTGAAAAAGC GTGTGCGAGC AAGGAGGCC                                           29

(2) INFORMATION FOR SEQ ID NO: 35:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 35:

```
GTGGAAGGCT ACCCGAAACG TTTGACC                                    27
```

(2) INFORMATION FOR SEQ ID NO: 36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
GACAAAGATC GTACTTTTTG GAGAAATGTC                                 30
```

(2) INFORMATION FOR SEQ ID NO: 37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

```
GTTGAAGTCG GAAGTTTACA TACACTTAGG                                 30
```

(2) INFORMATION FOR SEQ ID NO: 38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

```
GTTTAAACCA GAAGTTTACA CACACTGTAT                                 30
```

(2) INFORMATION FOR SEQ ID NO: 39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

```
CCAGTGGGTC AGAAGTTTAC ATACACTAAG                                 30
```

(2) INFORMATION FOR SEQ ID NO: 40:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

```
CTTGAAAGTC AAGTTTACAT ACAATAAG                                   28
```

(2) INFORMATION FOR SEQ ID NO: 41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

TCCAGTGGGT CAGAAGTTTA CATACACTAA GT                        32

(2) INFORMATION FOR SEQ ID NO: 42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

TCCAGTGGGT CAGAAGTTTA CATACACTAA GT                        32

(2) INFORMATION FOR SEQ ID NO: 43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

TGAATTCGAG CTCGGTACCC TACAGT                              26

(2) INFORMATION FOR SEQ ID NO: 44:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

ACTGTAGGGG ATCCTCTAGA GTCGAC                              26

(2) INFORMATION FOR SEQ ID NO: 45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

AAATTTATTT AATGTGTACA TACAGT                              26

(2) INFORMATION FOR SEQ ID NO: 46:

(i) SEQUENCE CHARACTERISTICS:
        (A) LENGTH: 26 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

ACTGTATAAG AACCTTTAGA ACGAAG                                              26

(2) INFORMATION FOR SEQ ID NO: 47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

AAATTTATTT AATGTGTACA TA                                                  22

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

TAAGAACCTT TAGAACGAAG                                                     20

(2) INFORMATION FOR SEQ ID NO: 49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

GAATAAACAG TAGTTCAACT TACAGT                                              26

(2) INFORMATION FOR SEQ ID NO: 50:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

ACTGTATATG TTTTCATGGA AAATAG                                              26

(2) INFORMATION FOR SEQ ID NO: 51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 51:

GAATAAACAG TAGTTCAACT TA                                           22

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

TATGTTTTCA TGGAAAATAG                                              20

(2) INFORMATION FOR SEQ ID NO: 53:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

TCACTGACTC ATTCAACATC TACAGT                                       26

(2) INFORMATION FOR SEQ ID NO: 54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

ACTGTATTTA TTGAATGCCT GCTGAA                                       26

(2) INFORMATION FOR SEQ ID NO: 55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

TCACTGACTC ATTCAACATC TA                                           22

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

```
TTTATTGAAT GCCTGCTGAA                                              20

(2) INFORMATION FOR SEQ ID NO: 57:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

ACTTACATAA TTATAAGTTT TACAGT                                       26

(2) INFORMATION FOR SEQ ID NO: 58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

ACTGTATATA ATGATGACAT CTATTA                                       26

(2) INFORMATION FOR SEQ ID NO: 59:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

ACTTACATAA TTATAAGTTT TA                                           22

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

TATAATGATG ACATCTATTA                                              20

(2) INFORMATION FOR SEQ ID NO: 61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

TATAAAGACA CATTCACATG TACAGT                                       26

(2) INFORMATION FOR SEQ ID NO: 62:
```

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

ACTGTATGTT TACTGCGGCA CTATTC                                          26

(2) INFORMATION FOR SEQ ID NO: 63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

TATAAAGACA CATGCACACG TA                                              22
```